(12) United States Patent
Takahashi et al.

(10) Patent No.: US 11,780,812 B2
(45) Date of Patent: Oct. 10, 2023

(54) OXOPYRIDINE DERIVATIVES USEFUL AS AMINOCARBOXYMUCONATE SEMIALDEHYDE DECARBOXYLASE (ACMSD) INHIBITORS

(71) Applicant: OrsoBio, Inc., Palo Alto, CA (US)

(72) Inventors: Taisuke Takahashi, Tsukuba (JP); Nan Ji, Arlington, MA (US)

(73) Assignee: OrsoBio, Inc., Palo Alto, CA (US)

( * ) Notice: Subject to any disclaimer, the term of this patent is extended or adjusted under 35 U.S.C. 154(b) by 0 days.

(21) Appl. No.: 17/119,343

(22) Filed: Dec. 11, 2020

(65) Prior Publication Data

US 2021/0094916 A1 Apr. 1, 2021

Related U.S. Application Data

(63) Continuation of application No. 16/473,474, filed as application No. PCT/US2017/068673 on Dec. 28, 2017, now abandoned.

(60) Provisional application No. 62/440,601, filed on Dec. 30, 2016.

(51) Int. Cl.
*C07D 213/85* (2006.01)
*C07D 401/04* (2006.01)
*C07D 401/12* (2006.01)

(52) U.S. Cl.
CPC ......... *C07D 213/85* (2013.01); *C07D 401/04* (2013.01); *C07D 401/12* (2013.01)

(58) Field of Classification Search
CPC .................................................. C07D 213/85
See application file for complete search history.

(56) References Cited

U.S. PATENT DOCUMENTS

| 8,642,660 B2 | 2/2014 | Goldfarb |
| 9,050,346 B2 | 6/2015 | Hasvold et al. |
| 9,181,276 B2 | 11/2015 | Tachdjian et al. |
| 9,220,695 B2 | 12/2015 | Golub et al. |
| 2019/0367457 A1 | 12/2019 | Takahashi et al. |
| 2021/0094916 A1 | 4/2021 | Takahashi et al. |

FOREIGN PATENT DOCUMENTS

| CN | 103724207 A | 4/2014 |
| EP | 2773625 A1 | 9/2014 |
| EP | 2844649 A1 | 3/2015 |
| WO | 2002/024650 A2 | 3/2002 |
| WO | 2003/022840 A1 | 3/2003 |
| WO | 2010/132815 A1 | 11/2010 |
| WO | 2011/133920 A1 | 10/2011 |
| WO | 2012/123745 A1 | 9/2012 |
| WO | 2013/013815 A1 | 1/2013 |
| WO | 2013/184755 A2 | 12/2013 |
| WO | 2014/043252 A2 | 3/2014 |
| WO | 2014/093988 A2 | 6/2014 |
| WO | 2014/141110 A2 | 9/2014 |
| WO | 2014/153208 A1 | 9/2014 |
| WO | 2014/177982 A1 | 11/2014 |
| WO | 2015/040408 A2 | 3/2015 |
| WO | WO-2016/030534 A1 | 3/2016 |

OTHER PUBLICATIONS

STN Chemical Database entry for 2-[[3-Cyano-5-(ethoxycarbonyl)-6-oxo-1,6-dihydropyridin-2-yl]sulfanyl]acetic acid, RN 851175-99-0, Entered STN: May 26, 2005.*
Henry R. Henze and Charles M. Blair "The Number of Structurally Isomeric Alcohols of the Methanol Series" Journal of the American Chemical Society 1931, 3042.*
Mahgoub et al., Synthesis of new pyrido[3',2':4,5]thieno[3,2-d]pyrimidines and pyrazolylpyridines. Bulletin of the Faculty of Science, Assiut University. 1991;20(2):43-53.
Bartlett et al., Exploiting Chemical Diversity for Drug Discovery. RSC Biomolecular Sciences. The Royal Society of Chemistry, Chapter 5, pp. 113-118, (2006).
Dyachenko et al., Cyclization Reactions of Nitriles. XXXIX. Synthesis and Reactions of 3-cyano-6-hydorxy-2(1H)-Pyridinechalcogenones. Journal of General Chemistry of the USSR. (Zhurnal Obshchei Khimii). Sep. 1990;60(9):1729-1832.
Enamine, Screening Compounds. http://www.enamine.net/index.php?option=com_content&task=view&id=22&menuid=51&PHPSESSID. 2 pages, (2006).
EnamineStore, EN300-11684, 2-[(3-cyano-4-methyl-6-oxo-1,6-dihydropyridin-2-yl)sulfanyl]acetic acid. Enamine, https://www.enaminestore.com/catalog/EN300-11684. 2 pages, Apr. 15, 2020.
PubChem Substance Record EN300-11684, Enamine, 7 pages, Dec. 16, 2011.
PubChem Substance Record EN300-12688, Enamine, 8 pages, Dec. 16, 2011.
STN Accession No. 1991:558996, Cyclization reactions of nitriles. XXXIX. Synthesis and transformations fo 6-hydroxy-3-cyano-2(1H)-pyridinechalcogenones. 1 page.

(Continued)

*Primary Examiner* — David K O'Dell
(74) *Attorney, Agent, or Firm* — Young Basile Hanlon & MacFarlane, P.C.

(57) ABSTRACT

The present invention is related to a compound represented by the following structural formula: The present invention is also related a method of treating a subject with a disease which can be ameliorated by inhibition of aminocarboxymuconate semialdehyde decarboxylase (ACMSD).

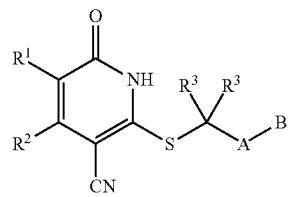

18 Claims, No Drawings

(56) References Cited

OTHER PUBLICATIONS

STN Accession No. 1992-407883, Synthesis of new pyrido [3',2':4,5]thieno[3.2-d]pyrimidines and pyrazolylpyridines. 1 page.
STN RN 2026582-81-8, Propanoic acid, 3-[(3-cyano-1,6-dihydro-4-methyl]-6-oxo-2-pyridinyl)thio], 1 page, Nov. 7, 2016.
Uorsy, Screening Compounds. Ukrorgsynthsis Ltd. 4 pages, (2008).
International Search Report and Written Opinion for Application No. PCT/US2017/068673, dated Mar. 20, 2018, 14 pages.

* cited by examiner

OXOPYRIDINE DERIVATIVES USEFUL AS AMINOCARBOXYMUCONATE SEMIALDEHYDE DECARBOXYLASE (ACMSD) INHIBITORS

CROSS-REFERENCES TO RELATED APPLICATIONS

This application is a continuation application of U.S. application Ser. No. 16/473,474, filed on Jun. 25, 2019, which is the U.S. national stage filing, under 35 U.S.C. § 371(c), of International Application No. PCT/US2017/068673, filed on Dec. 28, 2017, which claims the benefit of U.S. Provisional Application No. 62/440,601, filed on Dec. 30, 2016. The entire teachings of the aforementioned applications are incorporated herein by reference in their entirety.

FIELD OF THE INVENTION

This application is directed to inhibitors of aminocarboxymuconate semialdehyde decarboxylase (ACMSD), and methods for their use, such as to treat or prevent one or more ACMSD-related diseases.

BACKGROUND OF THE INVENTION

ACMSD is a critical enzyme for tryptophan metabolism, and regulates $NAD^+$ biosynthesis from tryptophan. ACMSD is a zinc-dependent amidohydrolase that participates in picolinic acid (PA), quinolinic acid (QA) and $NAD^+$ homeostasis. ACMSD stands at a branch point of the $NAD^+$ biosynthetic pathway from tryptophan and determines the final fate of the amino acid, i.e., transformation into PA, complete oxidation through the citric acid cycle, or conversion into $NAD^+$ through QA synthesis.

ACMSD has been purified from liver, kidney, and brain human tissues. There are two isoforms ACMSD1 and ACMSD2 derived from a differential splicing of ACMSD gene transcription but only ACMSD1 is endowed with enzymatic activity. ACMSD1 directs ACMS (α-amino-ω-carboxymuconic acid semialdehyde) to the acetyl-CoA pathway, and when ACMSD1 is inhibited, ACMS is non-enzymatically converted to quinolinic acid (QA) leading to the formation of $NAD^+$ and an increase in the intracellular level of $NAD^+$.

Increased levels of $NAD^+$ have been shown to protect against neuronal degeneration, improve muscle function and oxidative metabolism in mice, and enhance lifespan in worms. Whilst reduced levels of $NAD^+$ have been associated with a range of pathophysiological states including type 2 diabetes (T2D), hyperlipidemia (elevated cholesterol and TAGs), mitochondrial diseases, neutropenia, cancers, and kidney disorders.

The inhibition of ACMSD thus represents a novel approach to increase $NAD^+$ levels and modify disease pathophysiologies associated with defects in $NAD^+$ biosynthesis.

As such, there is a need for new and improved ACMSD inhibitors.

SUMMARY OF THE INVENTION

Applicant has now discovered novel compounds which are effective inhibitors of ACMSD-1 (see Example 57).

The present invention provides a compound represented by the following structural formula:

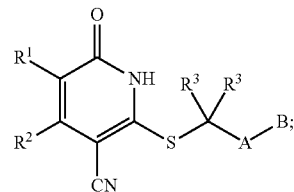

or a pharmaceutically acceptable salt thereof. The definition of each variable is provided below.

The present invention also provides a pharmaceutical composition comprising a compound as described above and a pharmaceutically acceptable carrier or diluent.

The present invention further provides a method of treating a subject with a disease which can be ameliorated by inhibition of ACMSD, comprising administering to the subject an effective amount of one or more disclosed compounds, or a pharmaceutically acceptable salt thereof, or the pharmaceutical compositions disclosed herein.

Also provided herein is the use of one or more of the disclosed compounds, or a pharmaceutically acceptable salt thereof, or the pharmaceutical compositions disclosed herein, for the preparation of a medicament for the treatment of a disease which can be ameliorated by inhibition of ACMSD.

In another embodiment provided herein, the disclosed compounds, or a pharmaceutically acceptable salt thereof, or the pharmaceutical compositions disclosed herein are for use in treating a disease which can be ameliorated by inhibition of ACMSD.

In one embodiment, the present invention provides a method of treating a subject with acute kidney injury, comprising administering to the subject an effective amount of one or more disclosed compounds, or a pharmaceutically acceptable salt thereof, or the pharmaceutical compositions disclosed herein.

Also provided herein is the use of one or more of the disclosed compounds, or a pharmaceutically acceptable salt thereof, or the pharmaceutical compositions disclosed herein, for the preparation of a medicament for the treatment of acute kidney injury.

In another embodiment provided herein, the disclosed compounds, or a pharmaceutically acceptable salt thereof, or the pharmaceutical compositions disclosed herein are for use in treating acute kidney injury.

In another embodiment, the present invention provides a method of treating a subject with cancer, comprising administering to the subject an effective amount of one or more disclosed compounds, or a pharmaceutically acceptable salt thereof, or the pharmaceutical compositions disclosed herein.

Also provided herein is the use of one or more of the disclosed compounds, or a pharmaceutically acceptable salt thereof, or the pharmaceutical compositions disclosed herein, for the preparation of a medicament for the treatment of cancer.

In another embodiment, provided herein the disclosed compounds, or a pharmaceutically acceptable salt thereof, or the pharmaceutical compositions disclosed herein are for use in treating cancer.

DETAILED DESCRIPTION

In a first embodiment, the invention provides a compound represented by the following structural formula:

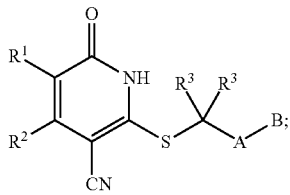

or a pharmaceutically acceptable salt thereof, wherein:

$R^1$ is —H, —CH$_3$, —OCH$_3$, halomethyl, halomethoxy, halo, or —CN;

$R^2$ is -halo, (C$_1$-C$_5$)alkyl, halo(C$_1$-C$_5$)alkyl, (C$_3$-C$_6$)cycloalkyl, phenyl, monocyclic heteroaryl, —CN, —NO$_2$, —OR$^c$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=O)OR$^b$, —O(C=S)NR$^a$R$^b$, —NR$^a$(C=O)NR$^a$R$^b$, —NR$^a$(C=S)NR$^a$R$^b$, —C(=S)R$^a$, or —C(=O)R$^b$, wherein:

the (C$_1$-C$_5$)alkyl group represented by $R^2$ is optionally substituted with —CN, —NO$_2$, —OR$^c$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, —C(=O)R$^a$, (C$_3$-C$_6$) cycloalkyl, monocyclic heteroaryl and phenyl, wherein the (C$_3$-C$_6$)cycloalkyl, monocyclic heteroaryl and phenyl substituents on the (C$_1$-C$_5$)alkyl group represented by $R^2$ are optionally and independently substituted with —CH$_3$, halomethyl, halo, methoxy or halomethoxy;

the (C$_3$-C$_6$)cycloalkyl, phenyl and monocyclic heteroaryl groups represented by $R^2$ are optionally and independently substituted with (C$_1$-C$_5$)alkyl, halo(C$_1$-C$_5$)alkyl, halo, —CN, —NO$_2$, —OR$^c$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, or —C(=O)R$^a$;

each $R^a$ and each $R^b$ are independently selected from —H and (C$_1$-C$_5$)alkyl, wherein the (C$_1$-C$_5$)alkyl group represented by $R^a$ or $R^b$ is optionally substituted with hydroxyl or (C$_1$-C$_3$)alkoxy;

$R^c$ is —H, halo(C$_1$-C$_5$)alkyl or (C$_1$-C$_5$)alkyl, wherein the (C$_1$-C$_5$)alkyl group represented by $R^c$ is optionally substituted with hydroxyl or (C$_1$-C$_3$)alkoxy;

i is 0, 1, or 2;

each $R^3$ is independently —H, —CH$_3$, or F;

A is absent, —CH$_2$—, a phenylene group or a pyridylene group, wherein the phenylene group and the pyridylene group represented by A are optionally and independently substituted with 1 or 2 groups represented by $R^4$;

each $R^4$ is independently —CH$_3$, —OCH$_3$, halomethyl, halomethoxy, halo, or —CN; and B is —COOH or tetrazolyl.

In a second embodiment, the invention provides a compound according to the previous embodiment, wherein the compound is represented by the following structural formula:

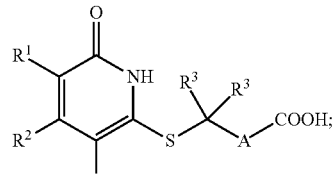

or a pharmaceutically acceptable salt thereof, wherein the definitions of the variables are as defined in the first embodiment.

In a third embodiment, the invention provides a compound according to the first embodiment, wherein the compound is represented by the following structural formula:

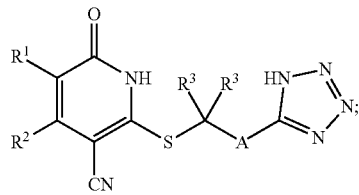

or a pharmaceutically acceptable salt thereof, wherein the definitions of the variables are as defined in the first embodiment.

In a fourth embodiment, the invention provides a compound according to the first embodiment, wherein the compound is represented by the following structural formula:

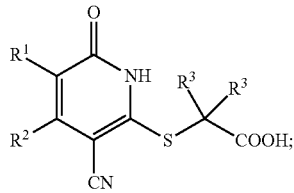

or a pharmaceutically acceptable salt thereof, wherein the definitions of the variables are as defined in the first embodiment.

In a fifth embodiment, the invention provides a compound according to the first embodiment, wherein the compound is represented by the following structural formula:

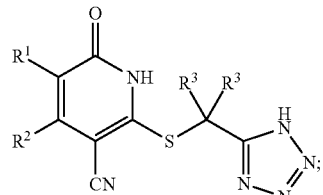

or a pharmaceutically acceptable salt thereof, wherein the definitions of the variables are as defined in the first embodiment.

In a sixth embodiment, the invention provides a compound according to the first embodiment, wherein the compound is represented by the following structural formula:

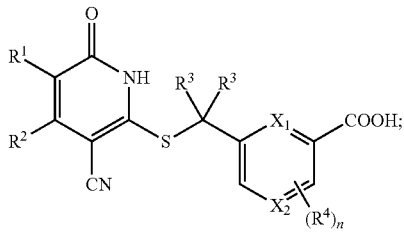

or a pharmaceutically acceptable salt thereof, wherein n is 0 or 1, $X_1$ and $X_2$ are each independently CH or N, and at least one of $X_1$ and $X_2$ is CH, the remainder of the variables are as described in the first embodiment.

In a seventh embodiment, the invention provides a compound according to the first embodiment, wherein the compound is represented by the following structural formula:

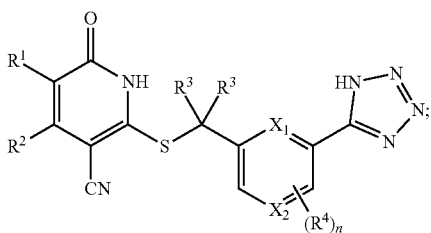

or a pharmaceutically acceptable salt thereof, wherein n is 0 or 1, $X_1$ and $X_2$ are each independently CH or N, and at least one of $X_1$ and $X_2$ is CH, the remainder of the variables are as described in the first embodiment.

In an eighth embodiment, the invention provides a compound according to the first embodiment, wherein the compound is represented by the following structural formula:

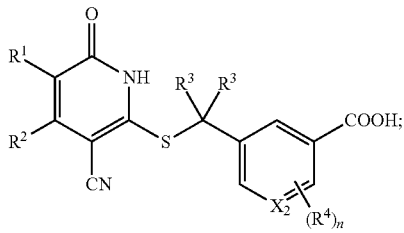

or a pharmaceutically acceptable salt thereof, wherein n is 0 or 1, $X_2$ is CH or N, the remainder of the variables are as described in the first embodiment.

In a ninth embodiment, the invention provides a compound according to the first embodiment, wherein the compound is represented by the following structural formula:

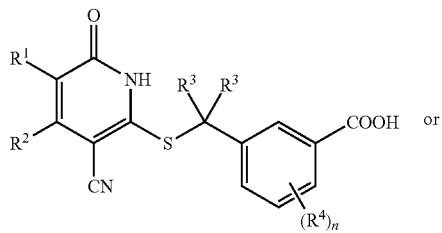

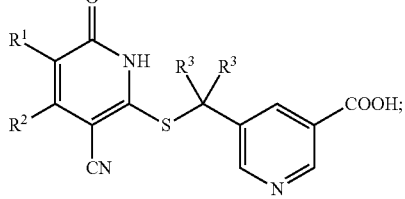

or a pharmaceutically acceptable salt thereof, wherein n is 0 or 1, the remainder of the variables are as described in the first embodiment.

In a tenth embodiment, the invention provides a compound according to the first embodiment, wherein the compound is represented by the following structural formula:

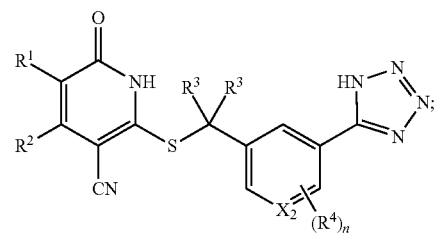

or a pharmaceutically acceptable salt thereof, wherein n is 0 or 1, $X_2$ is CH or N, the remainder of the variables are as described in the first embodiment.

In an eleventh embodiment, the invention provides a compound according to the first embodiment, wherein the compound is represented by the following structural formula:

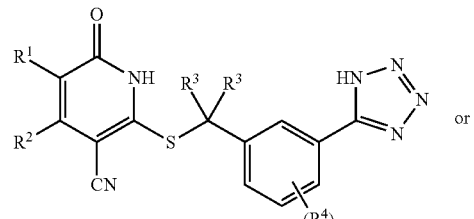

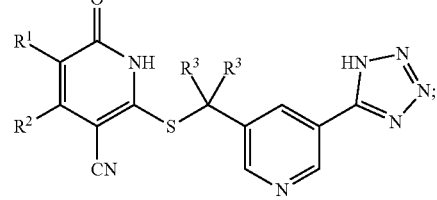

or a pharmaceutically acceptable salt thereof, wherein n is 0 or 1, the remainder of the variables are as described in the first embodiment.

In a twelfth embodiment, the invention provides a compound according to the first, second, third, fourth, fifth, sixth, seventh, eighth, ninth, tenth, or eleventh embodiment, or a pharmaceutically acceptable salt thereof, wherein $R^2$ is $(C_1-C_5)$alkyl, $(C_3-C_6)$cycloalkyl, phenyl, thienyl, furanyl, pyrimidyl, pyridyl, benzyl, thienyl-$CH_2$—, furanyl-$CH_2$—, pyrimidyl-$CH_2$— or pyrimidyl-$CH_2$—, wherein i) the $(C_1-C_5)$alkyl represented by $R_2$ is optionally substituted with halo, $(C_1-C_5)$alkoxy or $(C_3-C_6)$cycloalkyl; ii) the phenyl or benzyl group represented by $R_2$ is optionally and independently substituted with —$CH_3$, halomethyl, —$OCH_3$, halomethoxy and —CN; and iii) the thienyl, furanyl, pyridyl, pyrimidyl, thienyl-$CH_2$—, furanyl-$CH_2$—, pyridyl-$CH_2$— or pyrimidyl-$CH_2$— group represented by $R^2$ is optionally and independently substituted with —$CH_3$, the remainder of the variables are as described in the first, sixth, seventh, eighth, ninth, tenth, or eleventh embodiment.

In a thirteenth embodiment, the invention provides a compound according to the first, second, third, fourth, fifth, sixth, seventh, eighth, ninth, tenth, eleventh, or twelfth embodiment, or a pharmaceutically acceptable salt thereof, wherein $R^2$ is $(C_1-C_5)$alkyl, $(C_3-C_6)$cycloalkyl, phenyl, benzyl, thienyl or pyridyl, wherein i) the $(C_1-C_5)$alkyl represented by $R_2$ is optionally substituted with halo, $(C_1-C_5)$ alkoxy or $(C_3-C_6)$cycloalkyl; ii) the phenyl or benzyl group represented by $R^2$ is optionally and independently substituted with —$CH_3$, halomethyl, —$OCH_3$, halomethoxy, or —CN; and iii) the thienyl or pyridyl group represented by $R^2$ is optionally and independently substituted with —$CH_3$, the remainder of the variables are as described in the first, sixth, seventh, eighth, ninth, tenth, eleventh or twelfth embodiment.

In a fourteenth embodiment, the invention provides a compound according to the first, second, third, fourth, fifth, sixth, seventh, eighth, ninth, tenth, eleventh, twelfth, or thirteenth embodiment, or a pharmaceutically acceptable salt thereof, wherein $R^1$ is —H, —$CH_3$, —$OCH_3$, F, Cl, or —CN;

$R^2$ is $(C_1-C_5)$alkyl, $(C_3-C_6)$cycloalkyl, phenyl, thienyl, pyridyl or benzyl, wherein the $(C_1-C_5)$alkyl represented by $R_2$ is optionally substituted with halo, $(C_1-C_5)$alkoxy or $(C_3-C_6)$cycloalkyl; the phenyl or benzyl group represented by $R_2$ is optionally and independently substituted with —$CH_3$;

$R^3$ is —H, F, or —$CH_3$;

$R^4$ is F, Cl, —$CH_3$, or methoxy, the remainder of the variables are as described in the first, sixth, seventh, eighth, ninth, tenth, eleventh, twelfth, or thirteenth embodiment;

n is 0 or 1.

In a fifteenth embodiment, the invention provides a compound according to the first, second, third, fourth, fifth, sixth, seventh, eighth, ninth, tenth, eleventh, twelfth, thirteenth, or fourteenth embodiment, or a pharmaceutically acceptable salt thereof, wherein $R^1$ is —H, —$CH_3$, —$OCH_3$, F, or Cl;

$R^2$ is —$CF_3$, phenyl, toluenyl, thienyl, pyridyl, or benzyl;

$R^3$ is —H or F;

$R^4$ is F or Cl;

n is 0 or 1 and the remainder of the variables are as described in the first, sixth, seventh, eighth, ninth, tenth, eleventh, twelfth, thirteenth, or fourteenth embodiment.

In a sixteen embodiment, the invention provides a compound as described in any one of embodiments one through fifteen, provided that the compound is other than

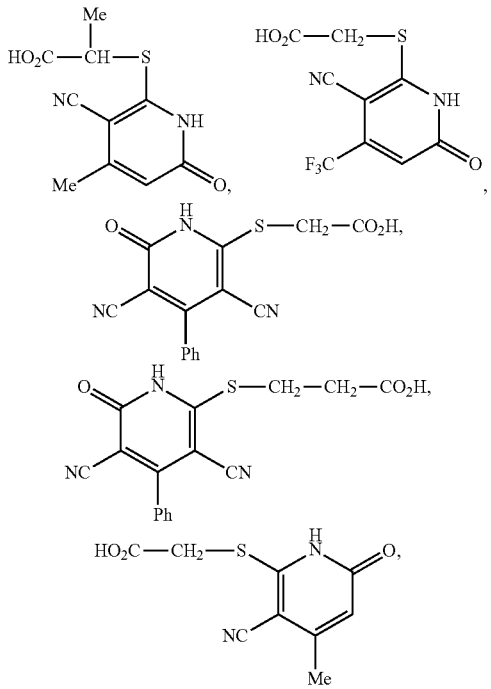

or a pharmaceutically acceptable salt of any of the foregoing.

In a seventeenth embodiment, the invention also includes any one of the compounds disclosed in the Exemplification or the Table in Example 57. Both pharmaceutically acceptable salts of these compounds and the corresponding neutral form of the compounds are included.

In another embodiment, the invention provides a pharmaceutical composition comprising (i) a pharmaceutically acceptable carrier or diluent and (ii) a compound according to the first, second, third, fourth, fifth, sixth, seventh, eighth, ninth, tenth, eleventh, twelfth, thirteenth, fourteenth, fifteenth, sixteenth or seventeenth embodiment.

The term "pharmaceutically-acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically-acceptable salts are well known in the art. For example, S. M. Berge et al. describes pharmacologically acceptable salts in *J. Pharm. Sci.*, 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric acid, hydrobromic, phosphoric, metaphosphoric, nitric, and sulfuric acids) and of organic acids (such as acetic acid, benzenesulfonic, benzoic, ethanesulfonic, methanesulfonic, succinic, and trifluoroacetic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Definitions

The term "halo" as used herein means halogen and includes chloro, fluoro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-5 carbon atoms, i.e. ($C_1$-$C_5$)alkyl. As used herein, a "($C_1$-$C_5$)alkyl" group means a radical having from 1 to 5 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "($C_1$-$C_4$)alkoxy" includes methoxy, ethoxy, propoxy, and butoxy.

The terms "haloalkyl" and "haloalkoxy" means alkyl or alkoxy, as the case may be, substituted with one or more halogen atoms.

The term "cycloalkyl" refers to a monocyclic saturated hydrocarbon ring system. For example, a $C_{3-6}$ cycloalkyl includes cyclopropyl, cyclobutyl, cyclopentyl and cyclohexyl. Unless otherwise described, a "cycloalkyl" has from three to six carbon atoms.

The term "heteroaryl", "heteroaromatic", "heteroaryl ring", "heteroaryl group", "heteroaromatic ring", and "heteroaromatic group", used alone or as part of a larger moiety as in "heteroaralkyl" or "heteroarylalkoxy", refers to monocyclic aromatic ring groups having five or six ring atoms (i.e., "5-6 membered") selected from carbon and at least one (typically 1 to 4, more typically 1 or 2) heteroatoms (e.g., oxygen, nitrogen or sulfur).

Examples of monocyclic heteroaryl groups include furanyl (e.g., 2-furanyl, 3-furanyl), imidazolyl (e.g., N-imidazolyl, 2-imidazolyl, 4-imidazolyl, 5-imidazolyl), isoxazolyl (e.g., 3-isoxazolyl, 4-isoxazolyl, 5-isoxazolyl), oxadiazolyl (e.g., 2-oxadiazolyl, 5-oxadiazolyl), oxazolyl (e.g., 2-oxazolyl, 4-oxazolyl, 5-oxazolyl), pyrazolyl (e.g., 3-pyrazolyl, 4-pyrazolyl), pyrrolyl (e.g., 1-pyrrolyl, 2-pyrrolyl, 3-pyrrolyl), pyridyl (e.g., 2-pyridyl, 3-pyridyl, 4-pyridyl), pyrimidinyl (e.g., 2-pyrimidinyl, 4-pyrimidinyl, 5-pyrimidinyl), pyridazinyl (e.g., 3-pyridazinyl), thiazolyl (e.g., 2-thiazolyl, 4-thiazolyl, 5-thiazolyl), triazolyl (e.g., 2-triazolyl, 5-triazolyl), tetrazolyl (e.g., tetrazolyl), thienyl (e.g., 2-thienyl, 3-thienyl), pyrimidinyl, pyridinyl and pyridazinyl.

The term "phenylene" refers to a group ($C_6H_4$) based on a di-substituted benzene ring.

The term "pyridylene" refers to a group ($C_6H_3N$) based on a di-substituted pyridine ring.

As used herein, many moieties (e.g., alkyl, alkylene, cycloalkyl, cycloalkylene, aryl, arylene, heteroaryl, heteroarylene, heterocyclyl or heterocyclylene) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant disclosure. The optional substituents can be any substituents that are suitable to attach to the moiety.

Suitable substituents are those which do not have a significant adverse effect on the ability of the compound to inhibit ACMSD. Where suitable substituents are not specifically enumerated, exemplary substituents include, but are not limited to: —$CH_3$, —$OCH_3$, halomethyl, halomethoxy, ($C_1$-$C_5$)alkyl, halo($C_1$-$C_5$)alkyl, ($C_1$-$C_5$)alkoxy, halo, —CN, —$NO_2$, —$OR^c$, —$NR^aR^b$, —$S(O)_iR^a$, —$NR^aS(O)_iR^b$, —$S(O)_iNR^aR^b$, —C(=O)$OR^a$, —OC(=O)$OR^a$, —C(=S)$OR^a$, —O(C=S)$R^a$, —C(=O)$NR^aR^b$, —$NR^aC$(=O)$R^b$, —C(=S)$NR^aR^b$, —$NR^aC$(=S)$R^b$, —$NR^a$(C=O)$OR^b$, —O(C=O)$NR^aR^b$, —$NR^a$(C=S)$OR^b$, —O(C=S)$NR^aR^b$, —$NR^a$(C=O)$NR^aR^b$, —$NR^a$(C=S)$NR^aR^b$, —C(=S)$R^a$, —C(=O)$R^a$, ($C_3$-$C_6$)cycloalkyl, monocyclic heteroaryl and phenyl, wherein the ($C_3$-$C_6$)cycloalkyl, monocyclic heteroaryl and phenyl substituents are optionally and independently substituted with —$CH_3$, halomethyl, halo, methoxy or halomethoxy. Each $R^a$ and each $R^b$ are independently selected from —H and ($C_1$-$C_5$)alkyl, wherein the ($C_1$-$C_5$) alkyl group represented by $R^a$ or $R^b$ is optionally substituted with hydroxyl or ($C_1$-$C_3$)alkoxy; $R^c$ is —H, halo($C_1$-$C_5$) alkyl or ($C_1$-$C_5$)alkyl, wherein the ($C_1$-$C_5$)alkyl group represented by $R^c$ is optionally substituted with hydroxyl or ($C_1$-$C_3$)alkoxy; and i is 0, 1, or 2.

In certain instances tautomeric forms of the disclosed compounds exist, such as the tautomeric structures shown below:

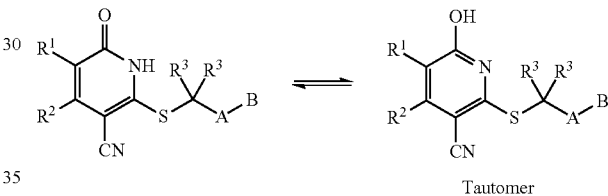

Tautomer

It is to be understood that when a compound herein is represented by a structural formula or designated by a chemical name herein, all other tautomeric forms which may exist for the compound are encompassed by the structural formula.

Pharmaceutical Compositions

The compounds disclosed therein are ACMSD inhibitors. The pharmaceutical composition of the present invention comprises one or more ACMSD inhibitors, or a pharmaceutically acceptable salt thereof, and a pharmaceutically acceptable carrier or diluent.

"Pharmaceutically acceptable carrier" and "pharmaceutically acceptable diluent" refer to a substance that aids the formulation and/or administration of an active agent to and/or absorption by a subject and can be included in the compositions of the present disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds.

The pharmaceutical compositions of the present teachings optionally include one or more pharmaceutically acceptable carriers and/or diluents therefor, such as lactose, starch, cellulose and dextrose. Other excipients, such as flavoring agents; sweeteners; and preservatives, such as methyl, ethyl, propyl and butyl parabens, can also be included. More complete listings of suitable excipients can be found in the Handbook of Pharmaceutical Excipients ($5^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003-20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

The present invention provides a method of treating a subject with a disease which can be ameliorated by inhibition of ACMSD, by administering to the subject an effective amount of one or more disclosed compounds, or a pharmaceutically acceptable salt thereof, or the corresponding pharmaceutical composition.

A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

In one embodiment, the diseases which can be ameliorated by inhibition of ACMSD are a muscle structure disorder, a neuronal activation disorder, a muscle fatigue disorder, a muscle mass disorder, a beta oxidation disease, a metabolic disease, a cancer, a vascular disease, an ocular vascular disease, a muscular eye disease, or a renal disease.

In one aspect of this embodiment, the muscle structure disorder is selected from Bethlem myopathy, central core disease, congenital fiber type disproportion, distal muscular dystrophy (MD), Duchenne & Becker MD, Emery-Dreifuss MD, facioscapulohumeral MD, hyaline body myopathy, limb-girdle MD, a muscle sodium channel disorders, myotonic chondrodystrophy, myotonic dystrophy, myotubular myopathy, nemaline body disease, oculopharyngeal MD, and stress urinary incontinence.

In another aspect of the embodiment, the neuronal activation disorder is selected from amyotrophic lateral sclerosis, Charcot-Marie-Tooth disease, Guillain-Barre syndrome, Lambert-Eaton syndrome, multiple sclerosis, myasthenia gravis, nerve lesion, peripheral neuropathy, spinal muscular atrophy, tardy ulnar nerve palsy, and toxic myoneural disorder.

In another aspect of this embodiment, the muscle fatigue disorder is selected from chronic fatigue syndrome, diabetes (type I or II), glycogen storage disease, fibromyalgia, Friedreich's ataxia, intermittent claudication, lipid storage myopathy, MELAS, mucopolysaccharidosis, Pompe disease, and thyrotoxic myopathy;

In another aspect of this embodiment, the muscle mass disorder is cachexia, cartilage degeneration, cerebral palsy, compartment syndrome, critical illness myopathy, inclusion body myositis, muscular atrophy (disuse), sarcopenia, steroid myopathy, and systemic lupus erythematosus.

In another aspect of this embodiment, the beta oxidation disease is selected from systemic carnitine transporter, carnitine palmitoyltransferase (CPT) II deficiency, very long-chain acyl-CoA dehydrogenase (LCHAD or VLCAD) deficiency, trifunctional enzyme deficiency, medium-chain acyl-CoA dehydrogenase (MCAD) deficiency, short-chain acyl-CoA dehydrogenase (SCAD) deficiency, and riboflavin-responsive disorders of β-oxidation (RR-MADD).

In yet another aspect of this embodiment, the metabolic disease is selected from hyperlipidemia, dyslipidemia, hypercholesterolemia, hypertriglyceridemia, HDL hypocholesterolemia, LDL hypercholesterolemia and/or HLD non-cholesterolemia, VLDL hyperproteinemia, dyslipoproteinemia, apolipoprotein A-I hypoproteinemia, atherosclerosis, disease of arterial sclerosis, disease of cardiovascular systems, cerebrovascular disease, peripheral circulatory disease, metabolic syndrome, syndrome X, obesity, diabetes (type I or II), hyperglycemia, insulin resistance, impaired glucose tolerance, hyperinsulinism, diabetic complication, cardiac insufficiency, cardiac infarction, cardiomyopathy, hypertension, Non-alcoholic fatty liver disease (NAFLD), Nonalcoholic steatohepatitis (NASH), thrombus, Alzheimer disease, neurodegenerative disease, demyelinating disease, multiple sclerosis, adrenal leukodystrophy, dermatitis, psoriasis, acne, skin aging, trichosis, inflammation, arthritis, asthma, hypersensitive intestine syndrome, ulcerative colitis, Crohn's disease, and pancreatitis.

In another aspect of this embodiment, the vascular disease is selected from peripheral vascular insufficiency, peripheral vascular disease, intermittent claudication, peripheral vascular disease (PVD), peripheral artery disease (PAD), peripheral artery occlusive disease (PAOD), and peripheral obliterative arteriopathy.

In another aspect of this embodiment, the ocular vascular disease is selected from age-related macular degeneration (AMD), stargardt disease, hypertensive retinopathy, diabetic retinopathy, retinopathy, macular degeneration, retinal haemorrhage, and glaucoma.

In a further aspect of this embodiment, the muscular eye disease is selected from strabismus, progressive external ophthalmoplegia, esotropia, exotropia, a disorder of refraction and accommodation, hypermetropia, myopia, astigmatism, anisometropia, presbyopia, a disorder of accommodation, and internal ophthalmoplegia.

In a final aspect of this embodiment, the renal disease is selected from glomerulonephritis, glomerulosclerosis, nephrotic syndrome, hypertensive nephrosclerosis, acute nephritis, recurrent hematuria, persistent hematuria, chronic nephritis, rapidly progressive nephritis, acute renal failure (also known as acute kidney injury), chronic renal failure, diabetic nephropathy, and Bartter's syndrome. In one embodiment, the renal disease is autosomal dominant polycystic kidney disease.

In another embodiment, the disease which can be ameliorated by inhibition of ACMSD includes genetic lipodystrophy, non-alcoholic fatty liver disease (NAFLD), non-alcoholic steatohepatitis (NASH), renal ischemia/reperfusion injury (IRI), Duchenne & Becker muscular dystrophy, diabetes (type I or type II), obesity, and sarcopenia.

In another embodiment, the disease which can be ameliorated by inhibition of ACMSD includes Alpers Disease, CPEO-Chronic progressive external ophthalmoplegia, Kearns-Sayra Syndrome (KSS), Leber Hereditary Optic Neuropathy (LHON), MELAS-Mitochondrial myopathy, encephalomyopathy, lactic acidosis, and stroke-like episodes, MERRF-Myoclonic epilepsy and ragged-red fiber disease, NARP-neurogenic muscle weakness, ataxia, and retinitis pigmentosa, Pearson Syndrome, platinum-based chemotherapy induced ototoxicity, Cockayne syndrome, xeroderma pigmentosum A, Wallerian degeneration, and HIV-induced lipodystrophy. In yet another embodiment, the disease which can be ameliorated by inhibition of ACMSD is acute kidney injury.

In certain embodiments, the invention provides methods for using the compounds of the invention and pharmaceutical compositions thereof. The compounds of the invention and pharmaceutical compositions thereof may be useful for a variety of therapeutic applications including, for example, treating and/or reducing a wide variety of diseases and disorders including, for example, diseases or disorders related to aging or stress, diabetes, obesity, neurodegenerative diseases, cardiovascular disease, blood clotting disorders, inflammation, cancer, and/or flushing, etc. The methods comprise administering to a subject in need thereof a pharmaceutically effective amount of one or more compounds of the invention and/or pharmaceutical compositions thereof.

In another embodiment, the compounds of the invention and pharmaceutical compositions thereof may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated using the compounds of the invention and pharmaceutical compositions thereof prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with the nicotinamide riboside chloride preparations or pharmaceutical compositions of the invention, or may have a subset of cells/tissue treated locally with the compounds of the invention and pharmaceutical compositions thereof. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, the compounds of the invention and/or a pharmaceutical composition thereof can be used to treat skin conditions. Exemplary skin conditions that may be treated in accordance with the methods described herein include disorders or diseases associated with or caused by inflammation, sun damage or natural aging. For example, the compositions find utility in the treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, the compounds of the invention and pharmaceutical compositions thereof may be used for the treatment of wounds and/or burns to promote healing, including, for example, first-, second- or third-degree burns and/or thermal, chemical or electrical burns.

The compounds of the invention and pharmaceutical compositions thereof can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

The compounds of the invention and pharmaceutical compositions thereof can also be administered to a subject suffering from an acute disease, e.g., damage to an organ or tissue, e.g., a subject suffering from stroke or myocardial infarction or a subject suffering from a spinal cord injury. The compounds of the invention and pharmaceutical compositions thereof may also be used to repair an alcoholic's liver.

In another embodiment, the invention provides a method for treating a cardiovascular disease by administering to a subject in need thereof one or more of the compounds of the invention and/or a pharmaceutical composition thereof. Cardiovascular diseases that can be treated using the compounds of the invention and pharmaceutical compositions thereof include cardiomyopathy or myocarditis; such as idiopathic cardiomyopathy, metabolic cardiomyopathy, alcoholic cardiomyopathy, drug-induced cardiomyopathy, ischemic cardiomyopathy, and hypertensive cardiomyopathy. Also treatable using compositions and methods described herein are atheromatous disorders of the major blood vessels (macrovascular disease) such as the aorta, the coronary arteries, the carotid arteries, the cerebrovascular arteries, the renal arteries, the iliac arteries, the femoral arteries, and the popliteal arteries. Other vascular diseases that can be treated include those related to platelet aggregation, the retinal arterioles, the glomerular arterioles, the vasa nervorum, cardiac arterioles, and associated capillary beds of the eye, the kidney, the heart, and the central and peripheral nervous systems. The compounds of the invention and pharmaceutical compositions thereof may also be used for increasing HDL levels in plasma of an individual.

Methods of Administration and Dosage Forms

The precise amount of compound administered to provide an "effective amount" to the subject will depend on the mode of administration, the type, and severity of the cancer, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used by following, for example, dosages reported in the literature and recommended in the Physician's Desk Reference (57th ed., 2003).

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, the disclosed ACMSD inhibitors can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds described herein will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a ACMSD mediated disease using the disclosed ACMSD inhibitors for guidance.

The compounds or the corresponding pharmaceutical compositions taught herein can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the present teachings may be incorporated with excipient and used in the form of ingestible tablets, buccal tablets, troches, capsules, elixirs, suspensions, syrups, wafers, and the like.

Typically for parenteral administration, solutions of a compound of the present teachings can generally be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound described herein for the extemporaneous preparation of sterile injectable solutions or dispersions are appropriate.

General Synthesis

Compounds of the present invention can be synthesized using the methodology shown in Schemes 1-3.

General synthesis scheme 1

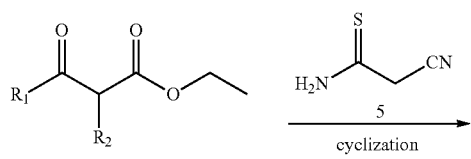

1
R1 = variant substituted groups
R2 = H or variant substituted groups

-continued

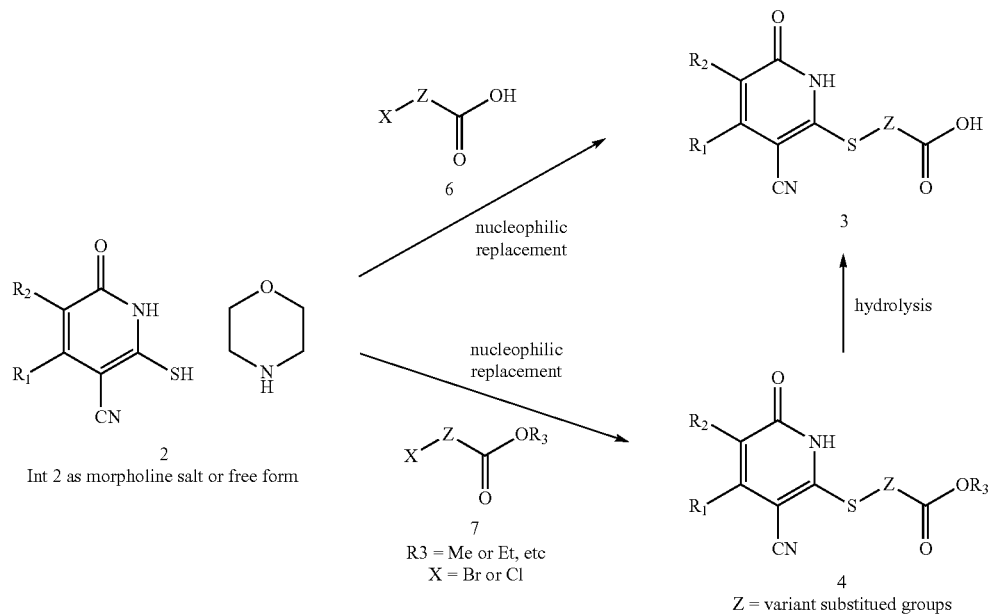

The 3-oxobutanoate 1 may be reacted with 2-cyanoethanethioamide 5, preferably in the presence of morpholine, to form cyclization product 2, either as a morpholine salt or a free base. Intermediate 2 then reacts with a carboxylic acid 6 (e.g., 2-bromoacetic acid) to form final product 3. Alternatively, intermediate 2 may react with an ester 7 to form compound 4, which is further hydrolyzed to yield final product 3.

General synthesis scheme 2

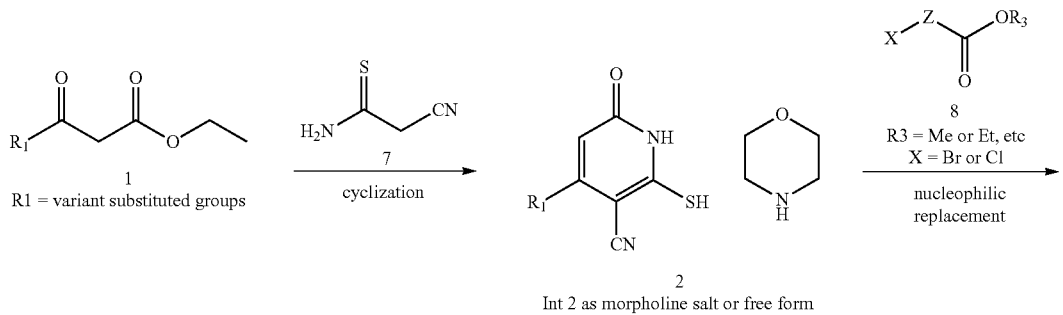

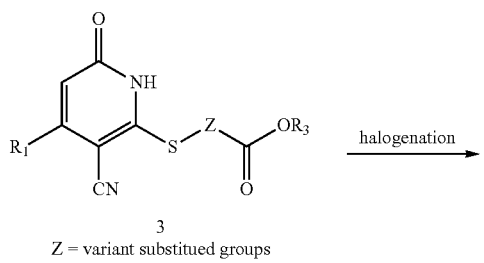

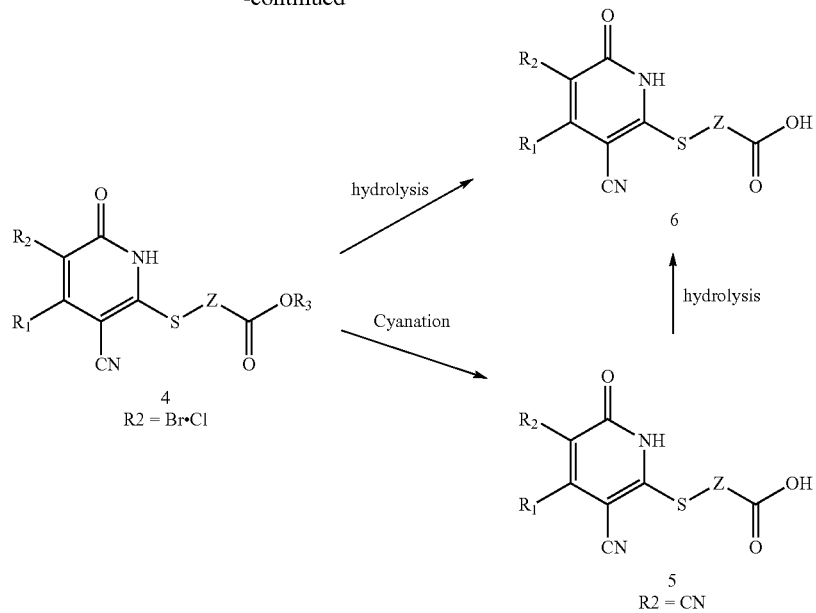

3-oxobutanoate 1 may be reacted with 2-cyanoethanethio-amide 7, preferably in the presence of morpholine, to form cyclization product 2, either as a morpholine salt or a free base. Compound 3 is formed by a nucleophilic substitution reaction between intermediate 2 and ester 8. Compound 3 is then converted into compound 4 by a halogenation reaction. Compound 4 is then hydrolyzed to form final product compound 6. Alternatively, compound 4 may be converted into compound 5 after a cynation step, which is further hydrolyzed to yield final product 6.

General synthesis scheme 3

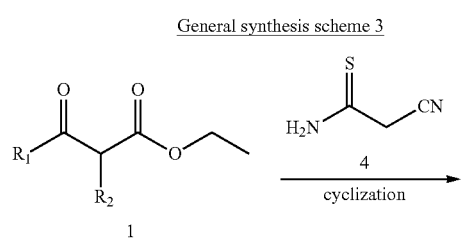

R1 = variant substituted groups
R2 = H or variant substituted groups

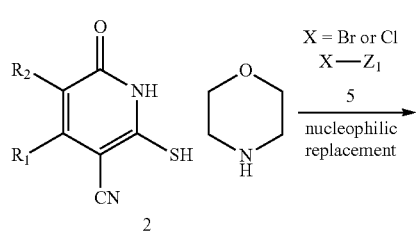

Int 2 as morpholine salt or free form

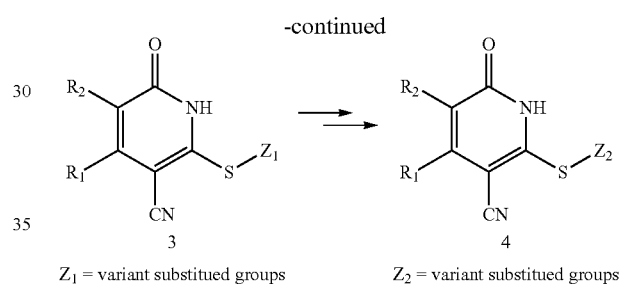

$Z_1$ = variant substitued groups  $Z_2$ = variant substitued groups 3-oxobutanoate 1 may be reacted with 2-cyanoethanethio-amide 4, preferably in the presence of morpholine, to form cyclization product 2, either as a morpholine salt or a free base. Compound 3 is formed by a nucleophilic substitution reaction between intermediate 2 and compound 5. Based on the different functional group $Z_1$ (e.g., —CN), compound 3 can be further converted into compound 4 with a functional group $Z_2$ (e.g., $Z_2$ being tetrazole).

EXEMPLIFICATION

Abbreviations

Me methyl
Et ethyl
iPr isopropyl
tBu tert-butyl
Boc tert-butyloxycarbonyl
Ac acetyl
AIBN azobisisobutyronitrile
DIPEA diisopropylethylamine
DCM dichloromethane
DMF dimethylformamide
DMSO dimethylsulfoxide
EA ethyl acetate
NBS N-bromosuccinimide
NCS N-chlorosuccinimide
NMP N-Methyl-2-pyrrolidone PE petroleum ether
Ph phenyl
Tf trifluoromethanesulfonyl
TFA trifluoroacetic acid
THF tetrahydrofuran
TMS trimethyl silane
TMSOTf trimethylsilyl trifluoromethanesulfonate
aq aqueous
M concencetration expressed in mol/L
r.t. room temperature
TLC thin layer chromatography
HPLC high-performance liquid chromatography
NMI 1-methyl imidazole
LCMS liquid chromatography-mass spectrometry
ESI+ m/z values in mass spectroscopy (Ionization ESI)
ESI− m/z values in mass spectroscopy (Ionization ESI)
ACN Acetonitrile
H NMR (DMSO-d$_6$) δ (ppm) of peak in $^1$H NMR in DMSO-d$_6$
s singlet (spectrum)
d doublet (spectrum)
t triplet (spectrum)
q quartet (spectrum)
dd double doublet (spectrum)
br broad line (spectrum)
m multiplet (spectrum).
mg milli gram
mM milli molar
nM nano molar
ng nano gram
μL microliter
EtOH ethanol
MeOH methanol
LAH lithium aluminum hydride Example 1—Synthesis of 2-((3-cyano-6-oxo-4-(trifluoromethyl)-1,6-dihydropyridin-2-yl)thio)acetic acid Synthesis scheme

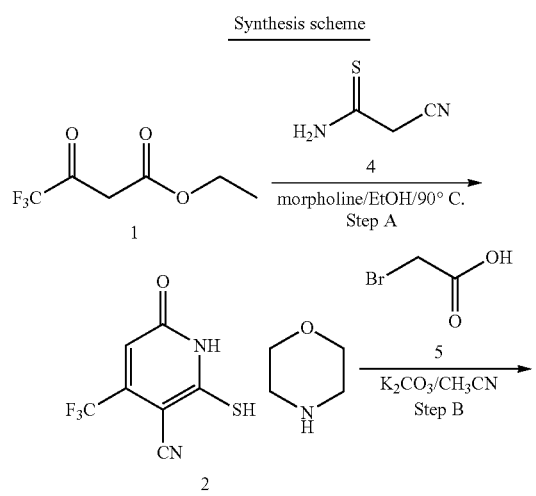

Step A: 2-mercapto-6-oxo-4-(trifluoromethyl)-1,6-dihydropyridine-3-carbonitrile as a 1:1 morpholine salt

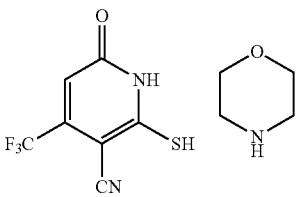

A mixture of ethyl 4,4,4-trifluoro-3-oxobutanoate (5 g, 27.2 mmol), 2-cyanoethanethioamide (2.99 g, 29.2 mmol), and morpholine (2.6 g, 29.9 mmol) in EtOH (30 mL) was stirred at 90° C. for 3 h under argon. Then the reaction mixture was cooled to room temperature and stirred overnight. The yellow precipitate was collected by filtration to give of the desired compound as a 1:1 morpholine salt (5.65 g).

$^1$H NMR (400 MHz, DMSO-d$_6$) δ: 11.45 (brs, 1H), 8.67 (brs, 2H), 5.81 (d, J=1.34 Hz, 1H), 3.67-3.82 (m, 4H), 3.05-3.16 (m, 4H). LC-MS (ESI$^+$): m/z 221.0 (M+H)$^+$.

Step B: 2-(3-cyano-6-oxo-4-(trifluoromethyl)-1,6-dihydropyridin-2-ylthio)acetic acid

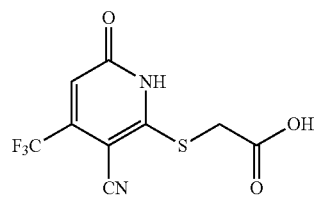

A mixture of 2-mercapto-6-oxo-4-(trifluoromethyl)-1,6-dihydropyridine-3-carbonitrile as a 1:1 morpholine salt (200 mg, 0.91 mmol), 2-bromoacetic acid (139 mg, 1.00 mmol), and K$_2$CO$_3$ (188 mg, 1.365 mmol) in acetonitrile (10 mL) was stirred at room temperature for 2 h. The solvent was removed under reduced pressure. The residue was poured into water (20 mL) and extracted with EtOAc (3×20 mL). The combined organic layers were washed with brine, dried over Na$_2$SO$_4$, filtered, and concentrated under reduced pressure. The residue was purified by prep-HPLC, eluting with MeOH/H$_2$O=65% (containing 0.1% HCOOH), to get the desired compound (120 mg) as a white solid.

$^1$H NMR (400 MHz, DMSO-d$_6$) δ: 13.12 (brs, 1H), 6.88 (s, 1H), 4.15 (s, 2H). LC-MS (ESI$^-$): m/z 277.0 (M−H)$^-$.

23

Example 2—Synthesis of 3-(3-cyano-6-oxo-4-(trifluoromethyl)-1,6-dihydropyridin-2-ylthio)propanioc acid

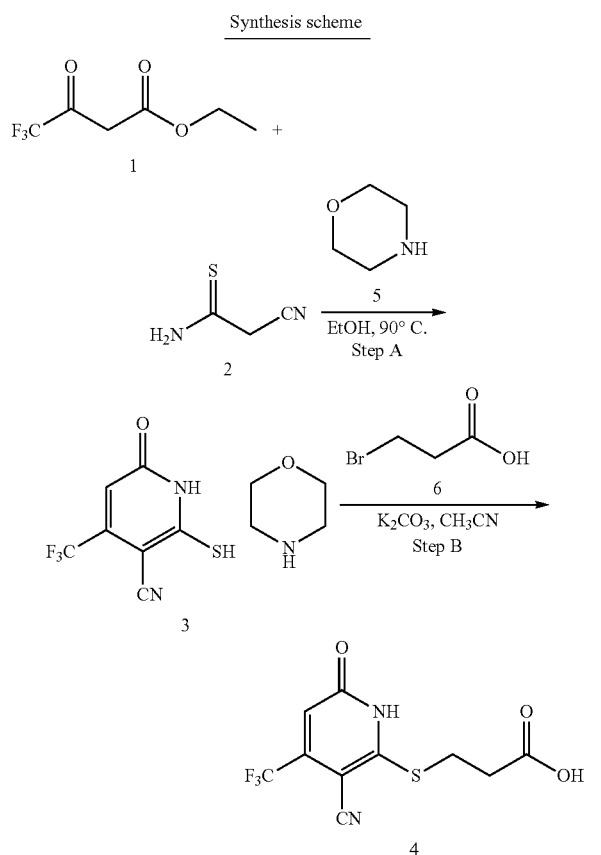

Step B: 3-(3-cyano-6-oxo-4-(trifluoromethyl)-1,6-dihydropyridin-2-ylthio)propanoic acid

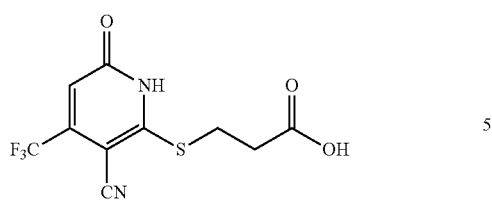

A mixture of 2-mercapto-6-oxo-4-(trifluoromethyl)-1,6-dihydropyridine-3-carbonitrile as a 1:1 morpholine salt (see Example 1, 200 mg, 0.651 mmol), 3-chloropropanoic acid (78 mg, 0.716 mmol), K₂CO₃ (188 mg, 1.302 mmol) in acetonitrile (10 mL) was stirred at room temperature for 2 h. The solvent was removed under reduced pressure. The residue was mixed with water (20 mL) and extracted with EtOAc (3×20 mL). The combined organic layers were washed with brine, dried over Na₂SO₄, filtered, and concentrated under reduced pressure. The residue was purified by prep-HPLC, eluting with MeOH/H₂O=65% (containing 0.1% HCOOH), to get the desired compound (110 mg) as a white solid.

24

$^1$H NMR (400 MHz, DMSO-d$_6$) δ: 12.71 (brs, 1H), 6.84 (s, 1H), 3.40 (t, J=6.98 Hz, 2H), 2.72 (t, J=6.85 Hz, 2H). LC-MS (ESI$^+$): m/z 293.1 (M+H)$^+$.

Example 3—Synthesis of 4-chloro-3-((3-cyano-6-oxo-4-(trifluoromethyl)-1,6-dihydropyridin-2-ylthio)methyl)benzoic acid Synthesis scheme

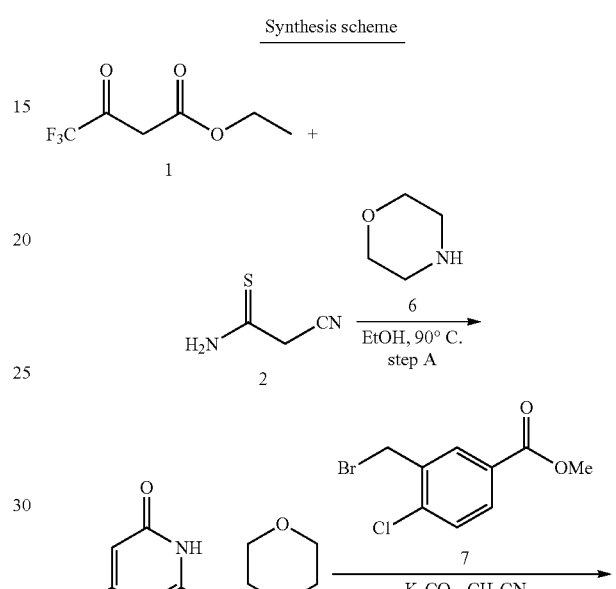

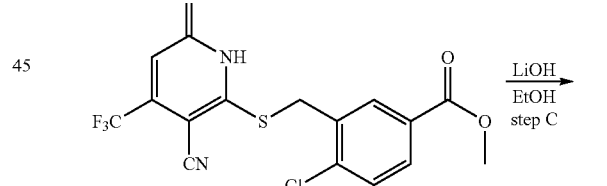

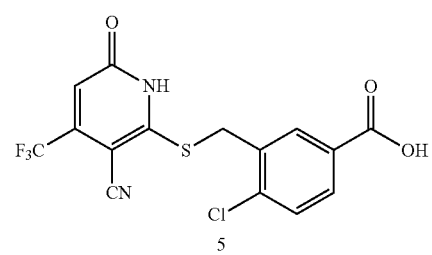

Step B: Methyl 4-chloro-3-((3-cyano-6-oxo-4-(trifluoromethyl)-1,6-dihydropyridin-2-ylthio)methyl)benzoate

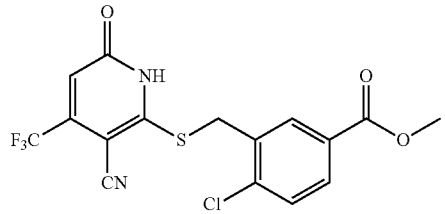 [SMILES: COC(=O)c1ccc(Cl)c(CSc2[nH]c(=O)cc(C(F)(F)F)c2C#N)c1]

A mixture of 2-mercapto-6-oxo-4-(trifluoromethyl)-1,6-dihydropyridine-3-carbonitrile as a 1:1 morpholine salt (see Example 1, 200 mg, 0.651 mmol), methyl 3-(bromomethyl)-4-chlorobenzoate (187 mg, 0.716 mmol), $K_2CO_3$ (188 mg, 1.302 mmol) in acetonitrile (10 mL) was stirred at room temperature for 2 h. The solvent was removed in vacuo. The residue was mixed with water (20 mL) and extract with EtOAc (3×20 mL). The combined organic layers were washed with brine, dried over $Na_2SO_4$, filtered, and concentrated under reduced pressure. The residue (220 mg) was used in the next step without further purification. LC-MS (ESI$^+$): m/z 403.0 (M+H)$^+$.

Step C: 4-chloro-3-((3-cyano-6-oxo-4-(trifluoromethyl)-1,6-dihydropyridin-2-ylthio)methyl)benzoic acid

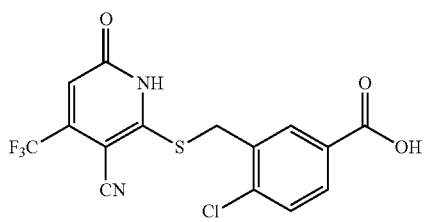

To a solution of methyl 4-chloro-3-((3-cyano-6-oxo-4-(trifluoromethyl)-1,6-dihydropyridin-2-ylthio)methyl)benzoate (220 mg, 0.55 mmol) in MeOH (5 mL) was added LiOH (45 mg, 1.1 mmol) in water (1 mL). Then the mixture was stirred at room temperature for 3 h. The solvent was removed in vacuo. The residue was poured in water (30 mL), acidified to pH=3-5 by addition of 1 N HCl, and extracted with EtOAc (3×30 mL). The combined organic layers were concentrated under reduced pressure. The residue was purified by prep-HPLC, eluting with MeOH/$H_2O$=50%-80%, to get the title compound (42 mg) as a white solid.

$^1$H NMR (400 MHz, DMSO-$d_6$) δ: 13.27 (brs, 2H), 8.22 (s, 1H), 7.81-7.93 (m, 1H), 7.65 (d, J=8.33 Hz, 1H), 6.90 (brs, 1H), 4.74 (brs, 2H). LC-MS (ESI$^+$): m/z 371.0 [M-OH]$^+$.

Example 4—Synthesis of 2-((3-cyano-4-(difluoromethyl)-6-oxo-1,6-dihydropyridin-2-yl)thio)acetic acid

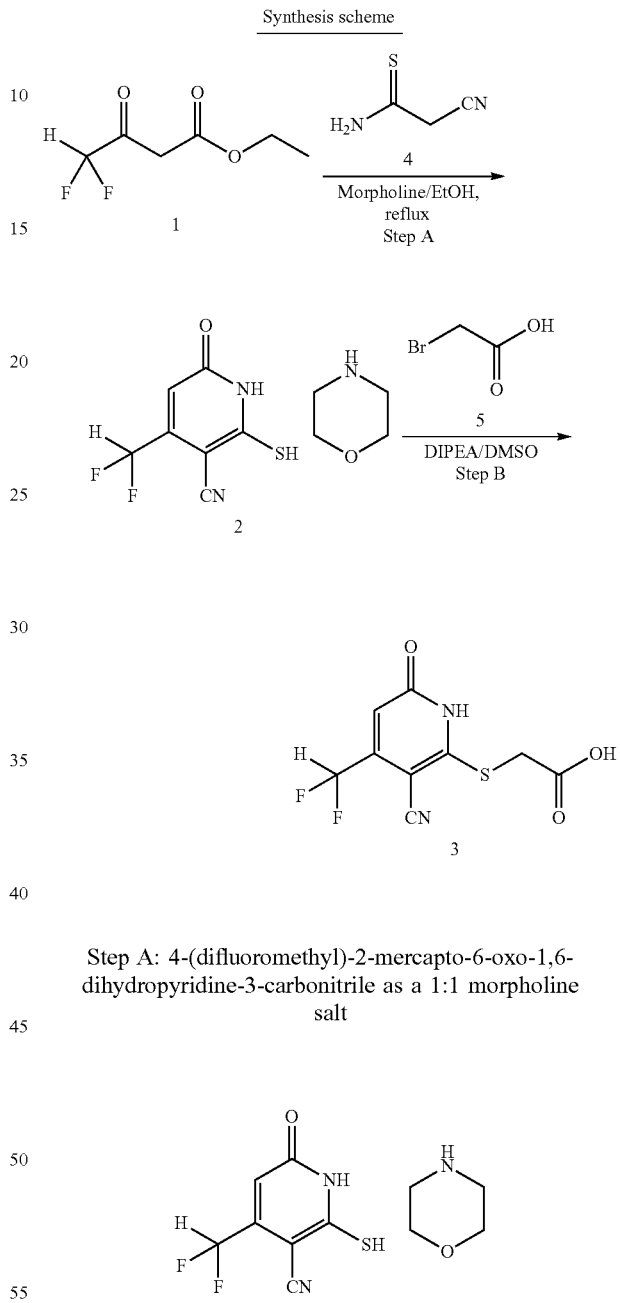

Step A: 4-(difluoromethyl)-2-mercapto-6-oxo-1,6-dihydropyridine-3-carbonitrile as a 1:1 morpholine salt To a solution of ethyl 4,4-difluoro-3-oxobutanoate (500 mg, 3.0 mmol) and 2-cyanoethanethioamide (300 mg, 3.0 mmol) in EtOH (15 mL) was added morpholine (287.1 mg, 3.3 mmol) at room temperature. The reaction was stirred at reflux for 3 h. TLC (EtOAc/PE=1:1, silica gel plate) showed complete consumption of the starting material after this time. The mixture was cooled to room temperature. The gray solid was collected by filtration, dried under vacuum to give the desired compound (591 mg) as a 1:1 morpholine salt. LC-MS (ESI$^+$): m/z 203.04 (M+H)$^+$.

Step B: 2-((3-cyano-4-(difluoromethyl)-6-oxo-1,6-dihydropyridin-2-yl)thio)acetic acid

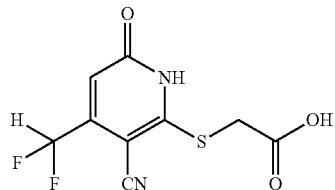

To a solution of 4-(difluoromethyl)-2-mercapto-6-oxo-1,6-dihydropyridine-3-carbonitrile as a 1:1 morpholine salt (202 mg, 1.0 mmol) and 2-bromoacetic acid (153 mg, 1.1 mmol) in DMSO (5 mL) was added DIPEA (142 mg, 1.1 mmol) at room temperature. The reaction was stirred at room temperature for 1 h. TLC (10% MeOH/90% DCM, silica gel plate) showed complete consumption of the starting material after this time. The solvent was removed under reduced pressure. The residue was poured into water (20 mL) and extracted with EtOAc (3×20 mL). The combined organic layers were washed with brine, dried over $Na_2SO_4$, filtered, and concentrated under reduced pressure. The residue was purified by prep-HPLC to get the desired compound (68.1 mg) as a white solid.

$^1$H NMR (400 MHz, DMSO-$d_6$) δ: 12.91 (s, 2H), 7.14 (t, J=53.7 Hz, 1H), 6.71 (s, 1H), 4.13 (s, 2H). LC-MS (ESI$^+$): m/z 261.0 (M+H)$^+$.

Example 5—Synthesis of 2-((3-cyano-5-methyl-6-oxo-4-(trifluoromethyl)-1,6-dihydropyridin-2-yl)thio)acetic acid Synthesis scheme

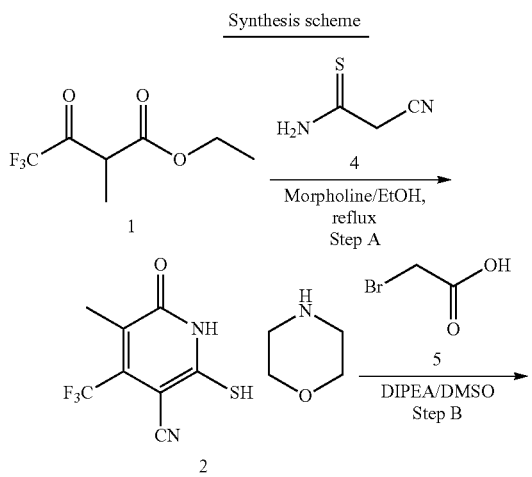

Step A: 2-mercapto-5-methyl-6-oxo-4-(trifluoromethyl)-1,6-dihydropyridine-3-carbonitrile as a 1:1 morpholine salt

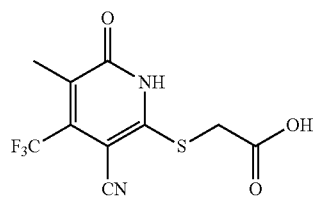

To a solution of ethyl 4,4,4-trifluoro-2-methyl-3-oxobutanoate (500 mg, 2.52 mmol) and 2-cyanoethanethioamide (252.4 mg, 2.52 mmol) in EtOH (15 mL) was added morpholine (285.0 mg, 3.3 mmol) at room temperature. The reaction was stirred at reflux for 3 h. TLC (EtOAc/PE=1:1, silica gel plate) showed complete consumption of the starting material after this time. The mixture was concentrated in vacuo. The residue was purified via reverse phase column chromatography (MeOH/$H_2O$=5%-80%) to give the desired compound as a 1:1 morpholine salt (235.1 mg) as a yellow solid. LC-MS (ESI$^+$): m/z 235.0 (M+H)$^+$.

Step B: 2-((3-cyano-5-methyl-6-oxo-4-(trifluoromethyl)-1,6-dihydropyridin-2-yl)thio)acetic acid

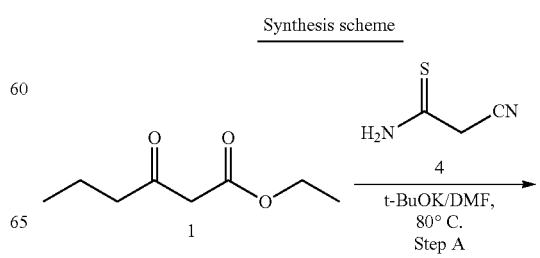

To a solution of 2-mercapto-5-methyl-6-oxo-4-(trifluoromethyl)-1,6-dihydropyridine-3-carbonitrile as a 1:1 morpholine salt (234 mg, 1.0 mmol) and 2-bromoacetic acid (153 mg, 1.1 mmol) in DMSO (5 mL) was added DIPEA (142 mg, 1.1 mmol) at room temperature. The reaction was stirred at room temperature for 1 h. TLC (10% MeOH/90% DCM, silica gel plate) showed complete consumption of the starting material after this time. The residue was purified by prep-HPLC to get the desired compound (58.8 mg) as a white solid.

$^1$H NMR (400 MHz, DMSO-$d_6$) δ: 13.15 (s, 2H), 4.16 (s, 2H), 2.20 (q, J=2.4 Hz, 3H). LC-MS (ESI$^+$): m/z 293.0 (M+H)$^+$.

Example 6—Synthesis of 2-((3-cyano-6-oxo-4-propyl-1,6-dihydropyridin-2-yl)thio)acetic acid Synthesis scheme

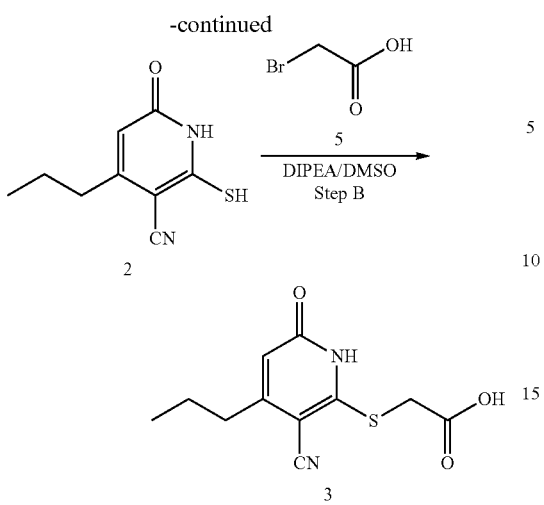

Step A: 2-mercapto-6-oxo-4-propyl-1,6-dihydropyridine-3-carbonitrile

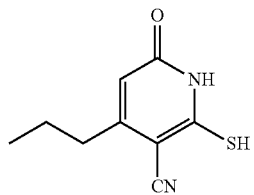

To a solution of ethyl 3-oxohexanoate (1.0 g, 6.321 mmol) and 2-cyanoethanethioamide (695 mg, 6.95 mmol) in DMF (20 mL) was added t-BuOK (701.6 mg, 6.321 mmol) at room temperature. The reaction was heated at 80° C. for 4 h under $N_2$. TLC (50% PE/50% EtOAc, silica gel plate) showed complete consumption of the starting material after this time. The mixture was cooled to room temperature, adjusted to pH=5.0, and extracted with EtOAc (2×50 mL). The combined organic layers were washed with brine, dried, and concentrated in vacuo. The residue was purified via column chromatography (DCM/MeOH=10:1) to give the desired compound (560.0 mg) as a yellow solid. LC-MS (ESI⁺): m/z 195.1 (M+H)⁺.

Step B: 2-((3-cyano-6-oxo-4-propyl-1,6-dihydropyridin-2-yl)thio)acetic acid

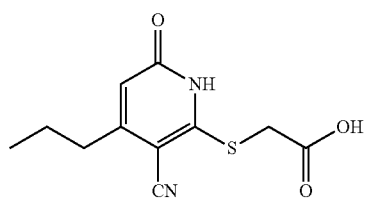 [SMILES: CCCc1cc(=O)[nH]c(SCC(=O)O)c1C#N]

To a solution of 2-mercapto-6-oxo-4-propyl-1,6-dihydropyridine-3-carbonitrile (250 mg, 1.29 mmol) and 2-bromoacetic acid (188.1 mg, 1.35 mmol) in DMSO (5 mL) was added DIPEA (199.7 mg, 1.55 mmol) at room temperature. The reaction was stirred at room temperature for 1 h. TLC (10% MeOH/90% DCM, silica gel plate) showed complete consumption of the starting material after this time. The mixture was cooled to room temperature, adjusted to pH=5.0, extracted with EtOAc (2×50 mL). The combined organic layer was washed with brine, dried, and concentrated in vacuo. The mixture was purified via reverse phase column chromatography (MeOH/H₂O=5%-80%) to give the desired compound (165.1 mg) as a white solid.

¹H NMR (400 MHz, DMSO-d₆) δ: 12.37 (s, 2H), 6.40 (s, 1H), 4.08 (s, 2H), 2.66-2.56 (m, 2H), 1.67-1.55 (m, 2H), 0.92 (t, J=7.3 Hz, 3H). LC-MS (ESI⁺): m/z 253.1 (M+H)⁺.

Example 7—Synthesis of 2-(3-cyano-6-oxo-4-(trifluoromethyl)-1,6-dihydropyridin-2-ylthio)propanoic acid Synthesis scheme

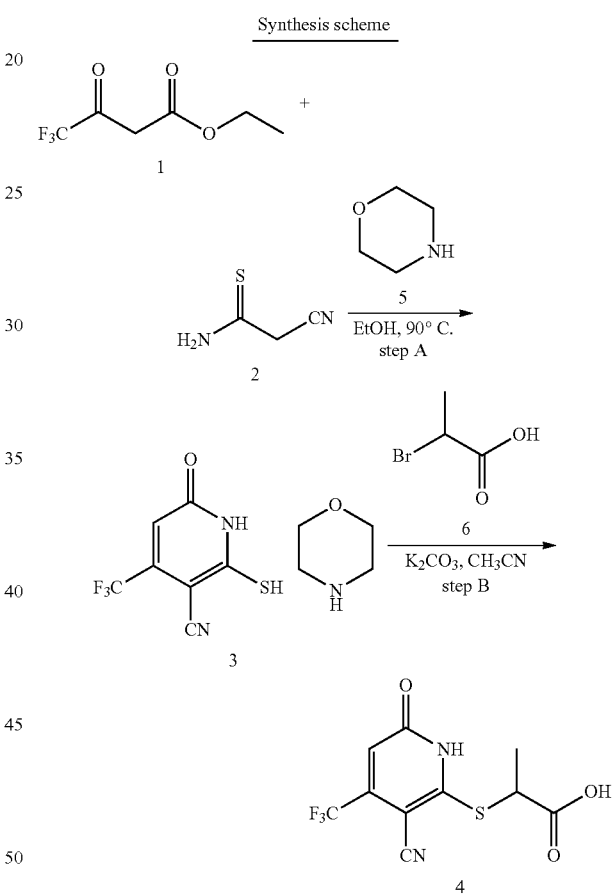

Step B: 2-(3-cyano-6-oxo-4-(trifluoromethyl)-1,6-dihydropyridin-2-ylthio)propanoic acid

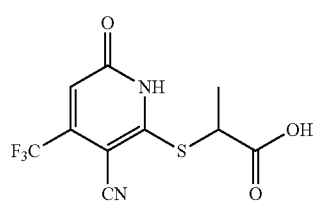

A mixture of 2-mercapto-6-oxo-4-(trifluoromethyl)-1,6-dihydropyridine-3-carbonitrile as a 1:1 morpholine salt (see Example 1, 200 mg, 0.651 mmol), 2-bromopropanoic acid (119 mg, 0.781 mmol), K$_2$CO$_3$ (188 mg, 1.302 mmol) in acetonitrile (10 ml) was stirred at room temperature for 2 h. The solvent was removed under reduced pressure. The residue was mixed with water (20 ml) and extracted with EtOAc (3×20 mL). The combined organic layers were washed with brine, dried over Na$_2$SO$_4$, filtered, and concentrated under reduced pressure. The residue was purified by prep-HPLC, eluting with MeOH/H$_2$O=50-80% (containing 0.1% HCOOH), to get the desired compound (25 mg) as a white solid.

$^1$H NMR (400 MHz, DMSO-d$_6$) δ: 13.30 (brs, 1H), 6.84 (s, 1H), 4.62 (d, J=7.3 Hz, 1H), 1.55 (d, J=7.6 Hz, 3H). LC-MS (ESI$^+$): m/z 292.9 (M+H)$^+$.

Example 8—Synthesis of 3-((3-cyano-6-oxo-4-(trifluoromethyl)-1,6-dihydropyridin-2-ylthio)methyl)benzoic acid Synthesis scheme

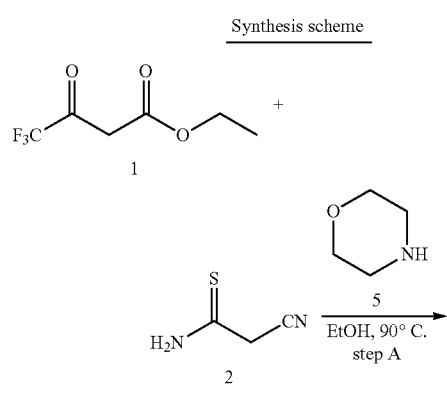

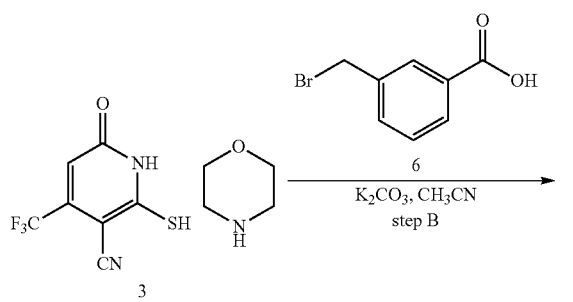

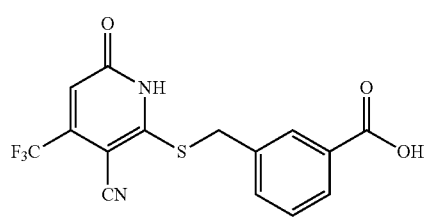 [SMILES: N#Cc1c(C(F)(F)F)cc(=O)[nH]c1SCc1cccc(C(=O)O)c1]

Step B: 3-((3-cyano-6-oxo-4-(trifluoromethyl)-1,6-dihydropyridin-2-ylthio)methyl)benzoic acid

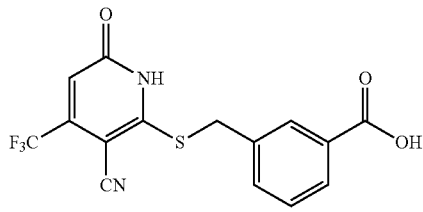

A mixture of 2-mercapto-6-oxo-4-(trifluoromethyl)-1,6-dihydropyridine-3-carbonitrile as a 1:1 morpholine salt (see Example 1, 200 mg, 0.651 mmol), 3-(bromomethyl)benzoic acid (154 mg, 0.717 mmol), K$_2$CO$_3$ (188 mg, 1.302 mmol) in acetonitrile (10 mL) was stirred at room temperature for 2 h. The solvent was removed in vacuo. The residue was poured into water (20 mL) and extracted with EtOAc (3×20 mL). The combined organic layers were washed with brine, dried over Na$_2$SO$_4$, filtered, and concentrated under reduced pressure. The residue was purified by prep-HPLC, eluting with MeOH/H$_2$O=50%-80%, to get the title compound (42 mg) as a white solid.

$^1$H NMR (400 MHz, Methanol-d$_4$) δ: 13.06 (brs, 2H), 8.04 (s, 1H), 7.84 (d, J=7.93 Hz, 1H), 7.74 (d, J=7.63 Hz, 1H), 7.46 (t, J=7.63 Hz, 1H), 6.88 (s, 1H), 4.62 (s, 2H). LC-MS (ESI$^-$): m/z 353.0 (M−H)$^-$.

Example 9—Synthesis of 2-((3-cyano-4-ethyl-6-oxo-1,6-dihydropyridin-2-yl)thio)acetic acid Synthesis scheme

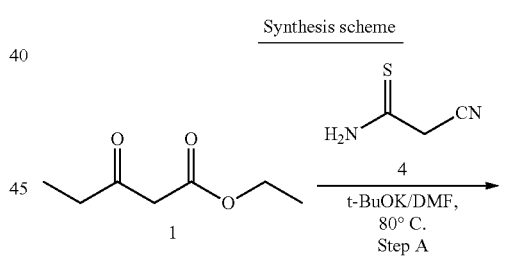

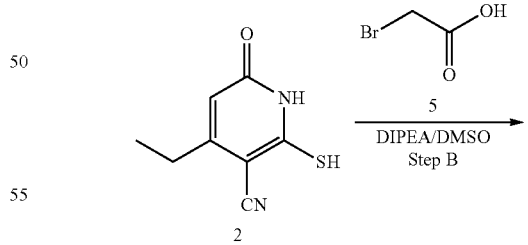

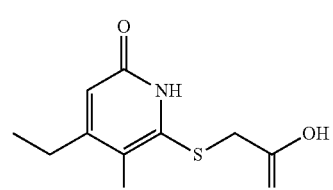

Step A: 4-ethyl-2-mercapto-6-oxo-1,6-dihydropyridine-3-carbonitrile

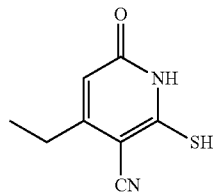

To a solution of ethyl 3-oxopentanoate (1.0 g, 6.94 mmol) and 2-cyanoethanethioamide (764 mg, 7.64 mmol) in DMF (10 mL) was added t-BuOK (855.6 mg, 7.64 mmol) at room temperature. The reaction mixture was heated at 80° C. for 4 h under $N_2$. TLC (50% PE/50% EtOAc, silica gel plate) showed complete consumption of the starting material after this time. The mixture was cooled to room temperature, adjusted to pH=5.0, and extracted with EtOAc (2×50 mL). The combined organic layers were washed with brine, dried, and concentrated in vacuo. The residue was purified via column chromatography (DCM/MeOH=10:1) to give the desired compound (1.05 g) as a yellow solid.

LC-MS (ESI$^+$): m/z 181.1 (M+H)$^+$.

Step B: 2-((3-cyano-4-ethyl-6-oxo-1,6-dihydropyridin-2-yl)thio)acetic acid

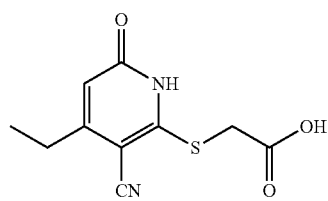 [SMILES: CCc1cc(=O)[nH]c(SCC(=O)O)c1C#N]

To a solution of 4-ethyl-2-mercapto-6-oxo-1,6-dihydropyridine-3-carbonitrile (250 mg, 1.39 mmol) and 2-bromoacetic acid (203 mg, 1.46 mmol) in DMSO (5 mL) was added DIPEA (215 mg, 1.67 mmol) at r.t. The reaction was stirred at r.t. for 1 h. TLC (10% MeOH/90% DCM, silica gel plate) showed complete consumption of the starting material after this time. The mixture was cooled to r.t., adjusted to pH=5.0, and extracted with EtOAc (2×50 mL). The combined organic layers were washed with brine, dried, and concentrated in vacuo. The mixture was purified via reverse phase column chromatography (MeOH/$H_2O$=5%-80%) to give the desired compound (160 mg) as a white solid.

$^1$H NMR (400 MHz, DMSO-$d_6$) δ: 12.40 (s, 2H), 6.42 (s, 1H), 4.08 (s, 2H), 2.66 (q, J=7.5 Hz, 2H), 1.19 (t, J=7.5 Hz, 3H). LC-MS (ESI$^+$): m/z 239.1 (M+H)$^+$.

Example 10—Synthesis of 2-((4-(tert-butyl)-3-cyano-6-oxo-1,6-dihydropyridin-2-yl)thio)acetic acid

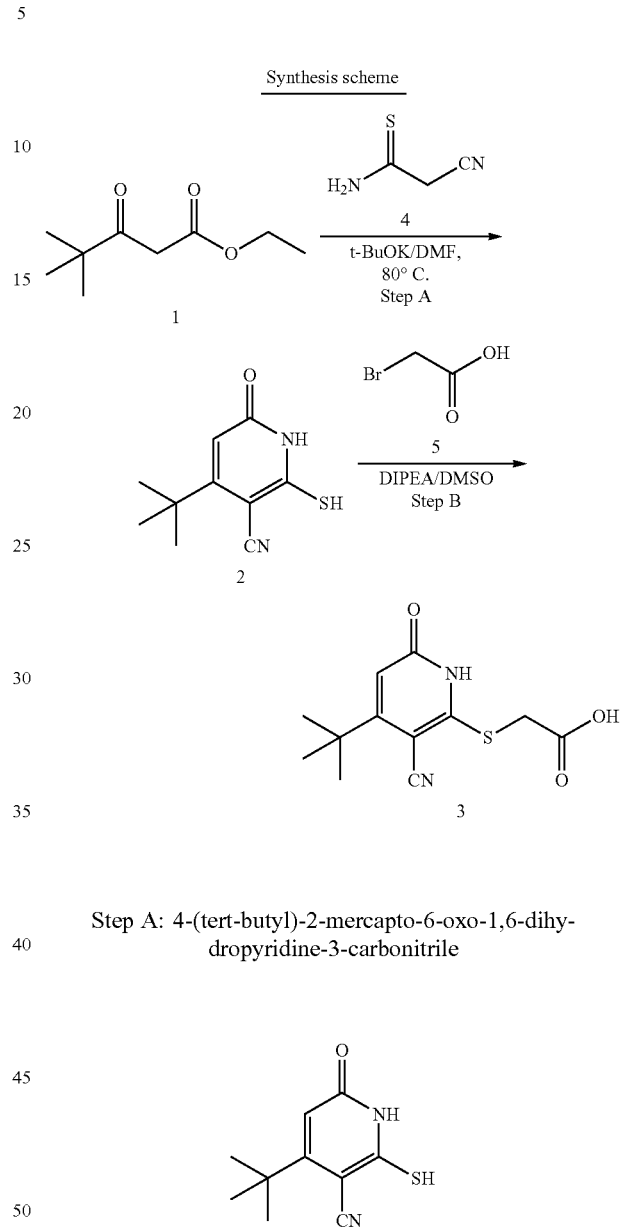

Synthesis scheme

Step A: 4-(tert-butyl)-2-mercapto-6-oxo-1,6-dihydropyridine-3-carbonitrile

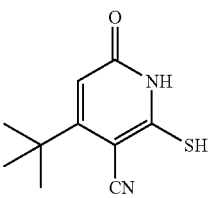

To a solution of ethyl 4,4-dimethyl-3-oxopentanoate (1.72 g, 10 mmol) and 2-cyanoethanethioamide (1.1 g, 11 mmol) in DMF (20 mL) was added t-BuOK (1.23 g, 11 mmol) at room temperature. The reaction was heated at 80° C. for 4 h under $N_2$. TLC (50% PE/50% EtOAc, silica gel plate) showed complete consumption of the starting material after this time. The mixture was cooled to room temperature, adjusted to pH=5.0, and extracted with EtOAc (2×50 mL). The combined organic layers were washed with brine, dried and concentrated in vacuo. The residue was purified via column chromatography (DCM/MeOH=10:1) to give the desired compound (196.0 mg) as a yellow solid. LC-MS (ESI$^+$): m/z 209.1 (M+H)$^+$.

Step B: 2-((4-(tert-butyl)-3-cyano-6-oxo-1,6-dihydropyridin-2-yl)thio)acetic acid

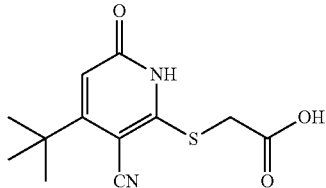 [SMILES: CC(C)(C)c1cc(=O)[nH]c(SCC(=O)O)c1C#N]

To a solution of 4-(tert-butyl)-2-mercapto-6-oxo-1,6-dihydropyridine-3-carbonitrile (196 mg, 0.942 mmol) and 2-bromoacetic acid (144 mg, 1.04 mmol) in DMSO (5 mL) was added DIPEA (146 mg, 1.13 mmol) at room temperature. The reaction was stirred at room temperature for 1 h. TLC (10% MeOH/90% DCM, silica gel plate) showed complete consumption of the starting material after this time. The mixture was cooled to room temperature, adjusted to PH=5.0, and extracted with EtOAc (2×50 mL). The combined organic layer was washed with brine, dried and concentrated in vacuo. The mixture was purified via reverse phase column chromatography (MeOH/H$_2$O=5%-80%) to give the desired compound (63.5 mg) as a yellow solid.

$^1$H NMR (400 MHz, DMSO-d$_6$) δ: 12.63 (s, 2H), 6.68 (s, 1H), 3.98 (s, 2H), 1.24 (s, 9H). LC-MS (ESI$^+$): m/z 267.1 (M+H)$^+$.

Example 11—Synthesis of 2-(3-cyano-4-(methoxymethyl)-6-oxo-1,6-dihydropyridin-2-ylthio)acetic acid Synthesis scheme

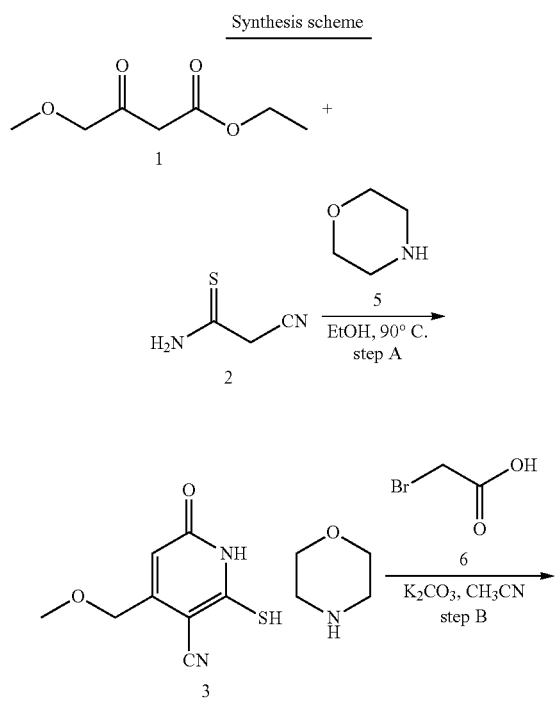

Step A: 2-mercapto-4-(methoxymethyl)-6-oxo-1,6-dihydropyridine-3-carbonitrile as a 1:1 morpholine salt

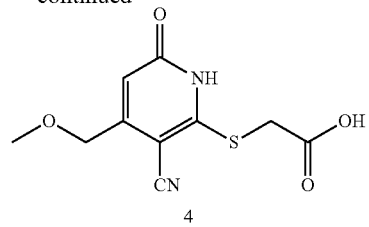

A mixture of ethyl 4-methoxy-3-oxobutanoate (500 mg, 3.42 mmol), 2-cyanoethanethioamide (377 mg, 3.77 mmol), morpholine (328 mg, 3.77 mmol) in EtOH (15 mL) was stirred at 90° C. for 3 h. The mixture was cooled to room temperature and stirred overnight. The yellow precipitate was collected by filtration to give of the desired compound (450 mg) as a 1:1 morpholine salt. LC-MS (ESI$^+$): m/z 197.0 (M+H)$^+$.

Step B: 2-(3-cyano-4-(methoxymethyl)-6-oxo-1,6-dihydropyridin-2-ylthio)acetic acid

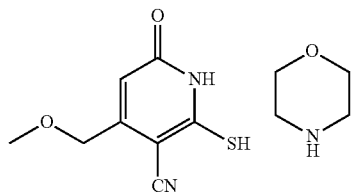

A mixture of 2-mercapto-4-(methoxymethyl)-6-oxo-1,6-dihydropyridine-3-carbonitrile as a 1:1 morpholine salt (200 mg, 0.704 mmol), 2-bromoacetic acid (107 mg, 0.774 mmol), K$_2$CO$_3$ (194 mg, 1.408 mmol) in DMF (10 mL) was stirred at room temperature for 2 h. The mixture was poured into water (20 mL), acidified by addition of 1 N HCl to pH=3-5, and extracted with EtOAc (3×20 mL). The combined organic layers were washed with brine, dried over Na$_2$SO$_4$, filtered, and concentrated under reduced pressure. The residue was purified by prep-HPLC, eluting with MeOH/water=50%-60% (containing 0.1% HCOOH), to get the desired compound (40 mg) as a white solid.

$^1$H NMR (400 MHz, DMSO-d$_6$) δ: 6.50 (s, 1H), 4.47 (s, 2H), 4.09 (s, 2H), 3.37 (s, 4H). LC-MS (ESI$^-$) m/z 253.0 (M−H)$^-$.

Example 12—Synthesis of 2-((3-cyano-6-oxo-4-phenyl-1,6-dihydropyridin-2-yl)thio)acetic acid

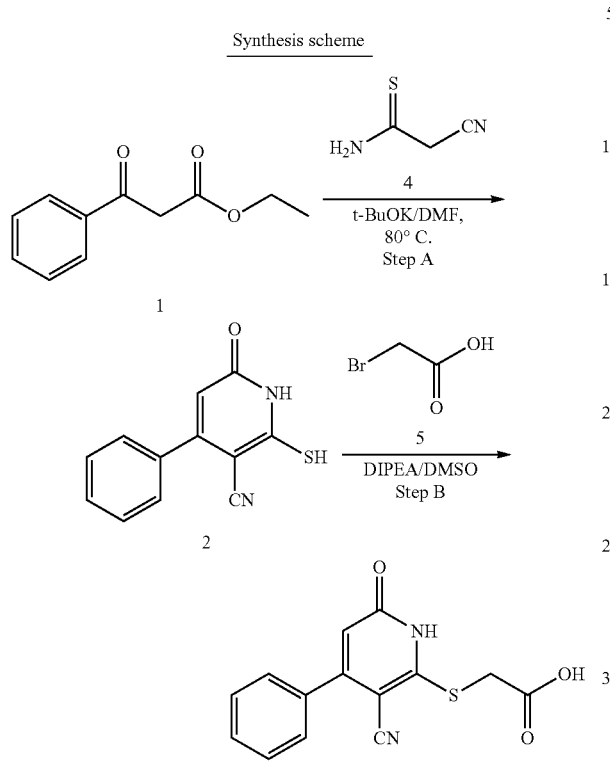

Step A: 2-mercapto-6-oxo-4-phenyl-1,6-dihydropyridine-3-carbonitrile

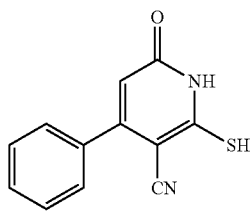 [SMILES: N#Cc1c(-c2ccccc2)cc(=O)[nH]c1S]

To a solution of ethyl 3-oxo-3-phenylpropanoate (1.2 g, 6.25 mmol) and 2-cyanoethanethioamide (687.5 mg, 6.88 mmol) in DMF (20 mL) was added t-BuOK (770 mg, 6.88 mmol) at room temperature. The reaction was heated at 80° C. for 4 h under $N_2$. TLC (50% PE/50% EtOAc, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The residue was purified via column chromatography (DCM/MeOH=10:1) to give the desired compound (568.0 mg) as a yellow solid.

$^1$H NMR (400 MHz, DMSO-d$_6$) δ: 13.25 (s, 1H), 7.72-7.64 (m, 2H), 7.61-7.50 (m, 3H), 6.50 (s, 1H). LC-MS (ESI$^+$): m/z 229.1 (M+H)$^+$.

Step B: 2-((3-cyano-6-oxo-4-phenyl-1,6-dihydropyridin-2-yl)thio)acetic acid

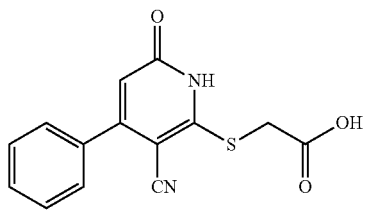 [SMILES: N#Cc1c(-c2ccccc2)cc(=O)[nH]c1SCC(=O)O]

To a solution of 2-mercapto-6-oxo-4-phenyl-1,6-dihydropyridine-3-carbonitrile (228 mg, 1.0 mmol) and 2-bromoacetic acid (146 mg, 1.05 mmol) in DMSO (5 mL) was added DIPEA (155 mg, 1.2 mmol) at room temperature. The reaction was stirred at room temperature for 1 h. TLC (10% MeOH/90% DCM, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The mixture was purified via reverse phase column chromatography (MeOH/H$_2$O=5%-80%) to give the desired compound (68.1 mg) as a white solid.

$^1$H NMR (400 MHz, DMSO-d$_6$) δ: 12.83 (s, 2H), 8.06-8.00 (m, 2H), 7.56-7.48 (m, 3H), 7.19 (s, 1H), 4.10 (s, 2H). LC-MS (ESI$^+$): m/z 287.1 (M+H)$^+$.

Example 13—Synthesis of 2-((3-cyano-4-isopropyl-6-oxo-1,6-dihydropyridin-2-yl)thio)acetic acid

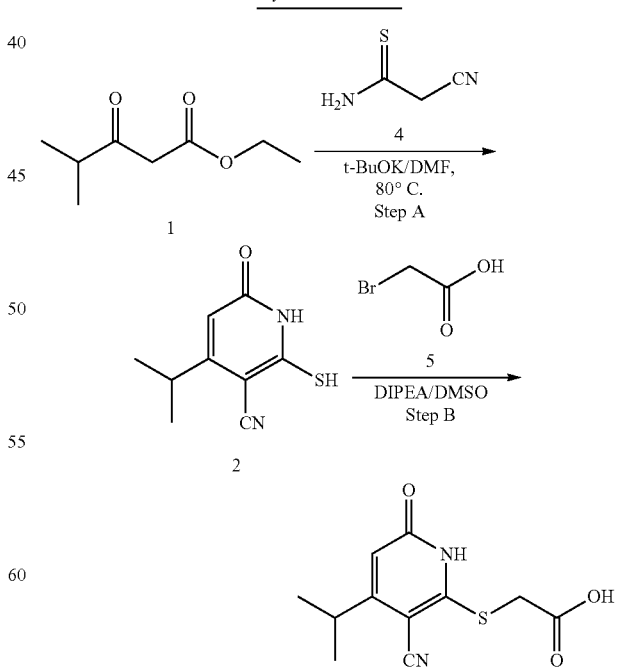

Step A: 4-isopropyl-2-mercapto-6-oxo-1,6-dihydropyridine-3-carbonitrile

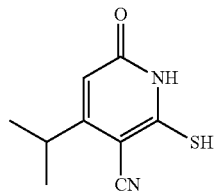

To a solution of ethyl 4-methyl-3-oxopentanoate (1.2 g, 7.59 mmol) and 2-cyanoethanethioamide (834 mg, 8.34 mmol) in DMF (20 mL) was added t-BuOK (935 mg, 8.34 mmol) at room temperature. The reaction was heated at 80° C. for 4 h under $N_2$. TLC (50% PE/50% EtOAc, silica gel plate) showed complete consumption of the starting material after this time. The mixture was cooled to r.t., adjusted to pH=5, and extracted with EtOAc (2×50 mL). The combined organic layers were washed with brine, dried and concentrated in vacuo. The residue was purified via column chromatography (DCM/MeOH=10:1) to give the desired compound (578 mg) as a brown solid. LC-MS (ESI+): m/z 195.1 (M+H)+.

Step B: 2-((3-cyano-4-isopropyl-6-oxo-1,6-dihydropyridin-2-yl)thio)acetic acid

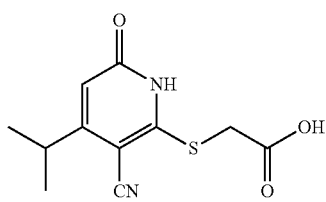 [SMILES: CC(C)c1cc(=O)[nH]c(SCC(=O)O)c1C#N]

To a solution of 4-isopropyl-2-mercapto-6-oxo-1,6-dihydropyridine-3-carbonitrile (194 mg, 1.0 mmol) and 2-bromoacetic acid (146 mg, 1.05 mmol) in DMSO (5 mL) was added DIPEA (155 mg, 1.2 mmol) at room temperature. The reaction was stirred at room temperature for 1 h. TLC (10% MeOH/90% DCM, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The mixture was purified via reverse phase column chromatography (MeOH/$H_2O$=5%-80%) to give the desired compound (33.6 mg) as a white solid.

$^1$H NMR (400 MHz, DMSO-$d_6$) δ: 12.20 (brs, 2H), 6.38 (s, 1H), 4.03 (s, 2H), 3.00 (dt, J=13.6 Hz, 6.8 Hz, 1H), 1.21 (d, J=6.9 Hz, 6H). LC-MS (ESI+): m/z 253.1 (M+H)+.

Example 14—Synthesis of 2-((3-cyano-4-cyclopropyl-6-oxo-1,6-dihydropyridin-2-yl)thio)acetic acid Synthesis scheme

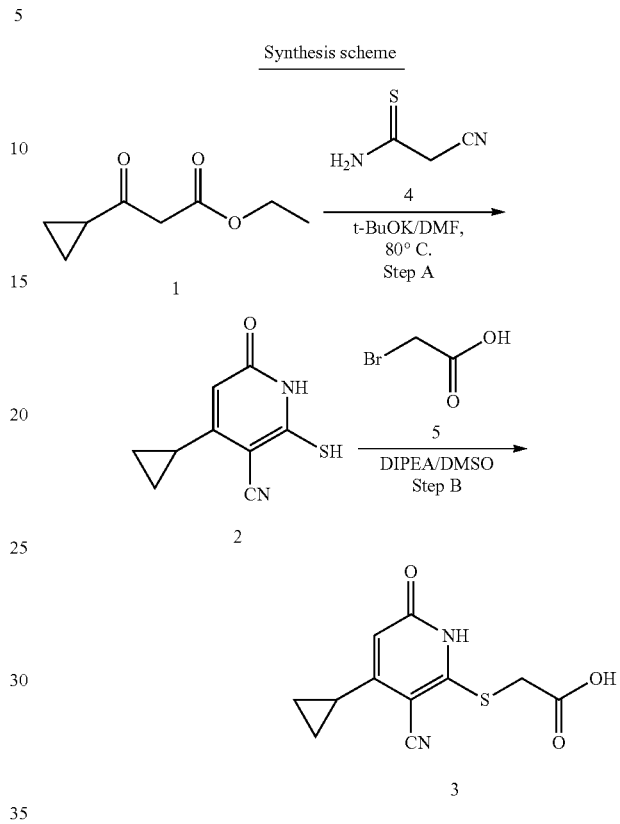

Step A: 4-cyclopropyl-2-mercapto-6-oxo-1,6-dihydropyridine-3-carbonitrile

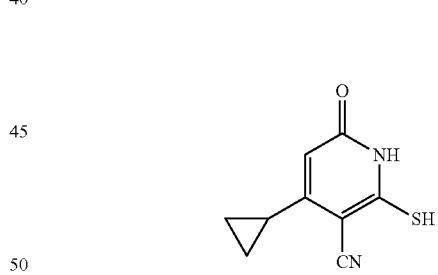

To a solution of ethyl 3-cyclopropyl-3-oxopropanoate (1.2 g, 7.68 mmol) and 2-cyanoethanethioamide (845 mg, 8.45 mmol) in DMF (15 mL) was added t-BuOK (946.5 mg, 8.45 mmol) at room temperature. The reaction was heated at 80° C. for 4 h under $N_2$. TLC (50% PE/50% EtOAc, silica gel plate) showed complete consumption of the starting material after this time. The mixture was cooled to room temperature, adjusted to PH=5.0, and extracted with EtOAc (2×50 mL). The combined organic layer was washed with brine, dried and concentrated in vacuo. The residue was purified via column chromatography (DCM/MeOH=10:1) to give the desired compound (598.1 mg) as a yellow solid. LC-MS (ESI+): m/z 193.1 (M+H)+.

Step B: 2-((3-cyano-4-cyclopropyl-6-oxo-1,6-dihydropyridin-2-yl)thio)acetic acid

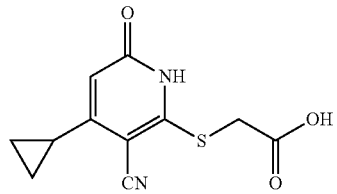 [SMILES: N#Cc1c(C2CC2)cc(=O)[nH]c1SCC(=O)O]

To a solution of 4-cyclopropyl-2-mercapto-6-oxo-1,6-dihydropyridine-3-carbonitrile (300 mg, 1.56 mmol) and 2-bromoacetic acid (217.2 mg, 1.56 mmol) in DMSO (10 mL) was added DIPEA (302 mg, 2.34 mmol) at room temperature. The reaction was stirred at room temperature for 1 h. TLC (10% MeOH/90% DCM, silica gel plate) showed complete consumption of the starting material after this time. The mixture was cooled to room temperature, adjusted to pH=5.0, and extracted with EtOAc (2×50 mL). The combined organic layer was washed with brine, dried and concentrated in vacuo. The mixture was purified via reverse phase column chromatography (MeOH/H$_2$O=5%-80%) to give the desired compound (93.9 mg) as a yellow solid.

$^1$H NMR (400 MHz, DMSO-d$_6$) δ: 12.69 (s, 1H), 12.33 (s, 1H), 6.68 (s, 1H), 3.90 (s, 2H), 2.07-1.95 (m, 1H), 1.06-0.99 (m, 2H), 0.95 (m, 2H). LC-MS (ESI$^-$): m/z 249.0 (M−H)$^-$.

Example 15—Synthesis of 3-(((3-cyano-6-oxo-4-phenyl-1,6-dihydropyridin-2-yl)thio)methyl)benzoic acid Synthesis scheme

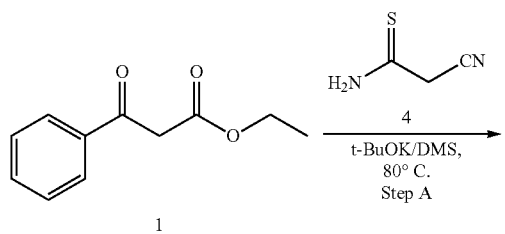

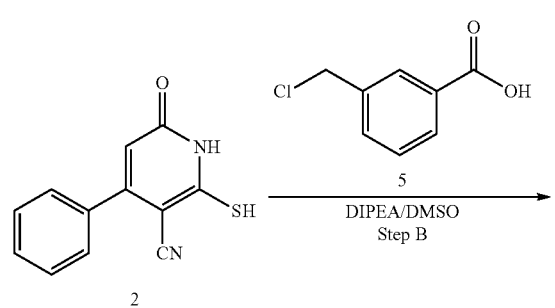

Step B: 3-(((3-cyano-6-oxo-4-phenyl-1,6-dihydropyridin-2-yl)thio)methyl)benzoic acid

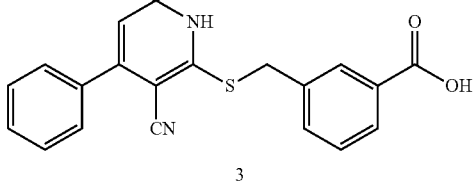

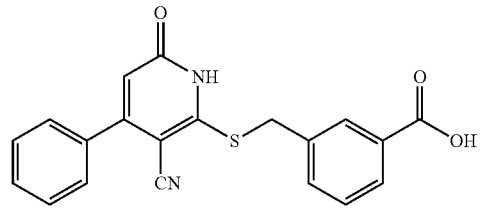

To a solution of 2-mercapto-6-oxo-4-phenyl-1,6-dihydropyridine-3-carbonitrile (see Example 12, 228 mg, 1.0 mmol) and 3-(chloromethyl)benzoic acid (170.6 mg, 1.0 mmol) in DMSO (5 mL) was added DIPEA (155 mg, 1.2 mmol) at room temperature. The reaction was stirred at room temperature for 1 h. TLC (10% MeOH/90% DCM, silica gel plate) showed complete consumption of the starting material after this time. The mixture was cooled to room temperature, adjusted to pH=5.0, and extracted with EtOAc (2×50 mL). The combined organic layers were washed with brine, dried and concentrated in vacuo. The mixture was purified via reverse phase column chromatography (MeOH/H$_2$O=5%-80%) to give the desired compound (29.4 mg) as a yellow solid.

$^1$H NMR (400 MHz, DMSO-d$_6$) δ: 12.97 (s, 2H), 8.09 (s, 1H), 8.05-7.96 (m, 2H), 7.82 (d, J=7.8 Hz, 1H), 7.71 (d, J=7.9 Hz, 1H), 7.58-7.49 (m, 3H), 7.44 (t, J=7.7 Hz, 1H), 7.17 (s, 1H), 4.70 (s, 2H). LC-MS (ESI$^-$): m/z 361.0 (M−H)$^-$.

Example 16—Synthesis of 3-(((3-cyano-6-oxo-4-(trifluoromethyl)-1,6-dihydropyridin-2-yl)thio)methyl)-4-methoxybenzoic acid Synthesis scheme

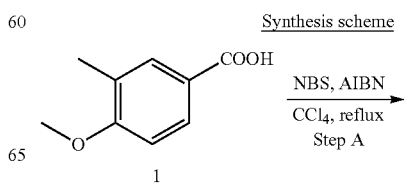

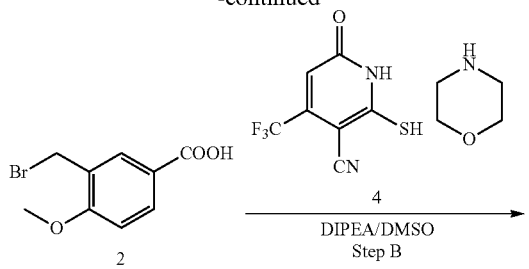

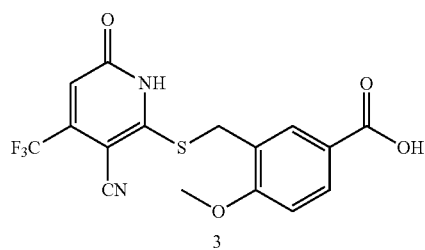

Step A: 3-(bromomethyl)-4-methoxybenzoic acid

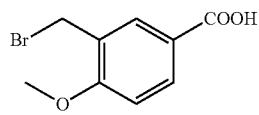

To a solution of 4-methoxy-3-methylbenzoic acid (1 g, 6.02 mmol) and NBS (1.61 g, 9.04 mmol) in CCl$_4$ (20 mL) was added AIBN (98.4 mg, 0.6 mmol) at room temperature. The reaction was stirred at reflux for 3 h. TLC (EtOAc/PE=2:1, silica gel plate) showed complete consumption of the starting material after this time. The mixture was concentrated in vacuo. The residue was purified via column chromatography (MeOH/DCM=1%-10%) to give the desired compound (371.2 mg) as a white solid. LC-MS (ESI$^+$): m/z 245.0, 247.0 (M+H)$^+$.

Step B: 3-(((3-cyano-6-oxo-4-(trifluoromethyl)-1,6-dihydropyridin-2-yl)thio)methyl)-4-methoxybenzoic acid

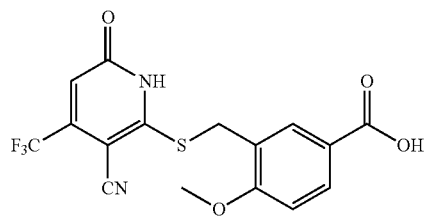 [SMILES: COc1ccc(C(=O)O)cc1CSc1[nH]c(=O)cc(C(F)(F)F)c1C#N]

To a solution of 2-mercapto-6-oxo-4-(trifluoromethyl)-1,6-dihydropyridine-3-carbonitrile as a 1:1 morpholine salt (307 mg, 1.0 mmol) and 3-(bromomethyl)-4-methoxybenzoic acid (268.5 mg, 1.1 mmol) in DMSO (5 mL) was added DIPEA (194 mg, 1.5 mmol) at room temperature. The reaction was stirred at room temperature for 1 h. TLC (10% MeOH/90% DCM, silica gel plate) showed complete consumption of the starting material after this time. The mixture was purified via reverse phase column chromatography (MeOH/H$_2$O=5%-80%) to give the desired compound (105 mg) as a white solid.

$^1$H NMR (400 MHz, DMSO-d$_6$) δ: 13.35 (s, 1H), 12.69 (s, 1H), 8.03 (d, J=2.2 Hz, 1H), 7.91 (dd, J=8.6, 2.2 Hz, 1H), 7.14 (d, J=8.7 Hz, 1H), 6.89 (s, 1H), 4.56 (s, 2H), 3.91 (s, 3H). LC-MS (ESI$^+$): m/z 383.0 (M–H)$^-$.

Example 17—Synthesis of 2-(3-cyano-5-fluoro-6-oxo-4-(trifluoromethyl)-1,6-dihydropyridin-2-ylthio)acetic acid Synthesis scheme

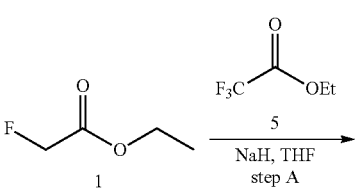

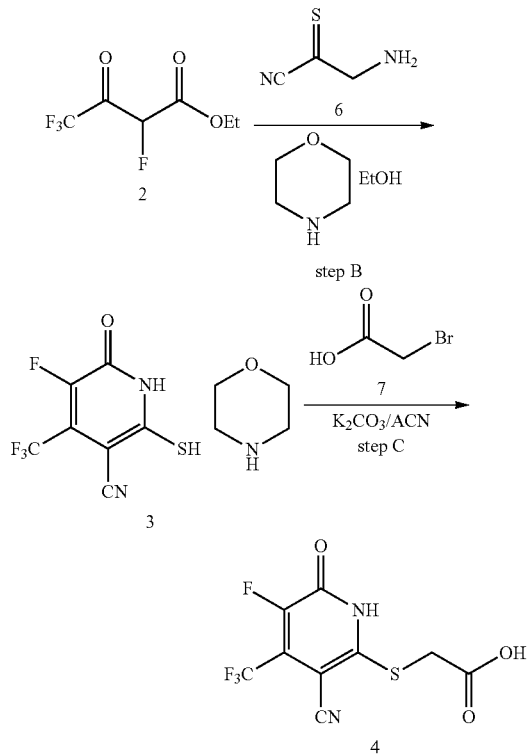

Step A: ethyl 2,4,4,4-tetrafluoro-3-oxobutanoate

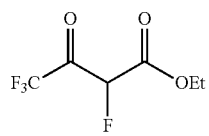

To a solution of ethyl 2,2,2-trifluoroacetate (2.68 g, 18.8 mmol) in dry THF (50 mL) was added NaH (380 mg, 9.5 mmol, 60% in oil) in portions, and the resultant mixture was heated to 50° C. Ethyl 2-fluoroacetate (1 g, 9.4 mmol) was then added dropwise over 5 min, and the mixture was stirred at 50° C. for 2 hr. The reaction mixture was cooled to room temperature and poured into ice (5 g)/concentrated sulfuric acid (0.5 mL). The aqueous layer was extracted with EtOAc (20 mL), and the organic layer washed with water (10 mL) and aqueous NaCl (50 mL), dried over $Na_2SO_4$, and evaporated. The residue was purified by silica gel column chromatography, eluting with PE/EtOAc=5:1, to get the title compound (600 mg) as a colorless oil.

$^1$H NMR (400 MHz, $CDCl_3$) δ: 5.17 (d, J=44 Hz, 1H), 4.42 (q, J=7.2 Hz, 2H), 1.40 (t, J=7.1 Hz, 3H).

Step B: 5-fluoro-2-mercapto-6-oxo-4-(trifluoromethyl)-1,6-dihydropyridine-3-carbonitrile as a 1:1 morpholine salt

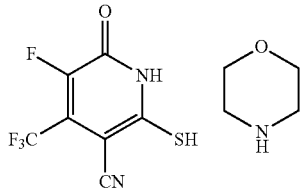

A mixture of ethyl 2,4,4,4-tetrafluoro-3-oxobutanoate (300 mg, 1.485 mmol), 2-cyanoethanethioamide (163 mg, 1.63 mmol), morpholine (142 mg, 1.63 mmol) in EtOH (10 mL) was stirred at 90° C. for 3 h. The mixture was cooled to room temperature and stirred overnight. The yellow precipitate was collected by filtration to give of the desired compound (240 mg) as a 1:1 morpholine salt. LC-MS (ESI⁻): m/z 237.0 (M−H)⁻.

Step C: 2-(3-cyano-5-fluoro-6-oxo-4-(trifluoromethyl)-1,6-dihydropyridin-2-ylthio)acetic acid

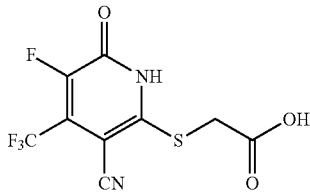 [SMILES: N#Cc1c(SCC(=O)O)[nH]c(=O)c(F)c1C(F)(F)F]

A mixture of 5-fluoro-2-mercapto-6-oxo-4-(trifluoromethyl)-1,6-dihydropyridine-3-carbonitrile as a 1:1 morpholine salt (240 mg, 0.74 mmol), 2-bromoacetic acid (124 mg, 0.888 mmol), $K_2CO_3$ (204 mg, 1.48 mmol) in $CH_3CN$ (10 mL) was stirred at room temperature for 2 h. The mixture was poured into water (20 mL), acidified by addition of 1 N HCl to pH=3-5, and extracted with EtOAc (3×20 mL). The combined organic layers were washed with brine, dried over $Na_2SO_4$, filtered, and concentrated under reduced pressure. The residue was purified by prep-HPLC, eluting with MeOH/Water=40%-60% (containing 0.1% HCOOH), to get the desired compound (150 mg) as a white solid.

$^1$H NMR (400 MHz, DMSO-$d_6$) δ: 4.10 (s, 2H). LC-MS (ESI⁻): m/z 294.9 (M−H)⁻

Example 18—Synthesis of 2-((4-benzyl-3-cyano-6-oxo-1,6-dihydropyridin-2-yl)thio)acetic acid

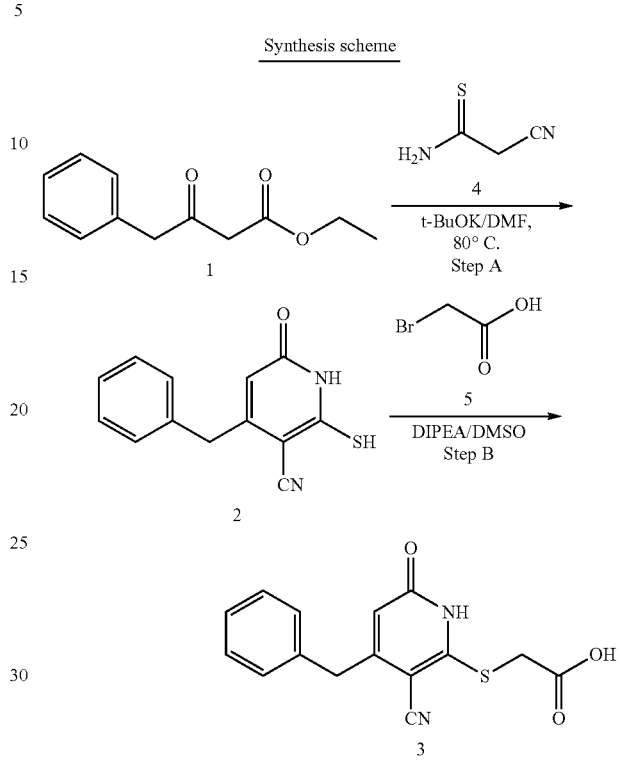

Step A: 4-benzyl-2-mercapto-6-oxo-1,6-dihydropyridine-3-carbonitrile

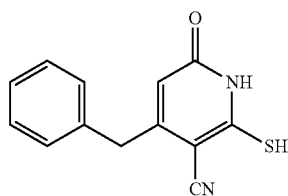 [SMILES: N#Cc1c(Cc2ccccc2)cc(=O)[nH]c1S]

To a solution of ethyl 3-oxo-4-phenylbutanoate (900 mg, 4.68 mmol) and 2-cyanoethanethioamide (515 mg, 5.15 mmol) in DMF (15 mL) was added t-BuOK (576.9 mg, 5.15 mmol) at room temperature. The reaction mixture was heated at 80° C. for 4 h under $N_2$. TLC (50% PE/50% EtOAc, silica gel plate) showed complete consumption of the starting material after this time. The mixture was cooled to room temperature, adjusted to pH=5, and extracted with EtOAc (2×50 mL). The combined organic layers were washed with brine, dried, and concentrated in vacuo. The residue was purified via column chromatography (DCM/MeOH=10:1) to give the desired compound (468.1 mg) as a yellow solid.

$^1$H NMR (400 MHz, DMSO-$d_6$) δ: 12.78 (s, 1H), 7.34 (dd, J=9.3, 5.3 Hz, 2H), 7.30-7.23 (m, 3H), 5.73 (s, 1H), 3.86 (s, 2H). LC-MS (ESI⁺): m/z 243.0 (M+H)⁺.

Step B: 2-((4-benzyl-3-cyano-6-oxo-1,6-dihydro-pyridin-2-yl)thio)acetic acid

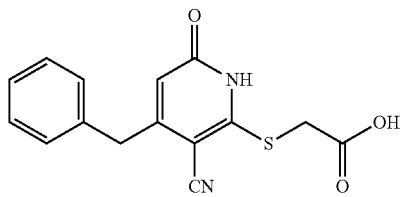 [SMILES: N#Cc1c(Cc2ccccc2)cc(=O)[nH]c1SCC(=O)O]

To a solution of 4-benzyl-2-mercapto-6-oxo-1,6-dihydropyridine-3-carbonitrile (200 mg, 0.826 mmol) and 2-bromoacetic acid (138 mg, 0.992 mmol) in DMSO (5 mL) was added DIPEA (159.8 mg, 1.239 mmol) at room temperature. The reaction mixture was stirred at room temperature for 1 h. TLC (10% MeOH/90% DCM, silica gel plate) showed complete consumption of the starting material after this time. The mixture was purified via reverse phase column chromatography (MeOH/H$_2$O=5%-80%) to give the desired compound (103.1 mg) as a yellow solid.

$^1$H NMR (400 MHz, DMSO-d$_6$) δ: 7.35 (dd, J=10.3, 4.4 Hz, 2H), 7.27 (dt, J=6.8, 3.0 Hz, 3H), 6.35 (s, 1H), 4.08 (s, 2H), 4.02 (s, 2H). LC-MS (ESI$^+$): m/z 301.1 (M+H)$^+$.

Example 19—Synthesis of 3-((3-cyano-6-oxo-4-(trifluoromethyl)-1,6-dihydropyridin-2-ylthio)methyl)-4-fluorobenzoic acid Synthesis scheme

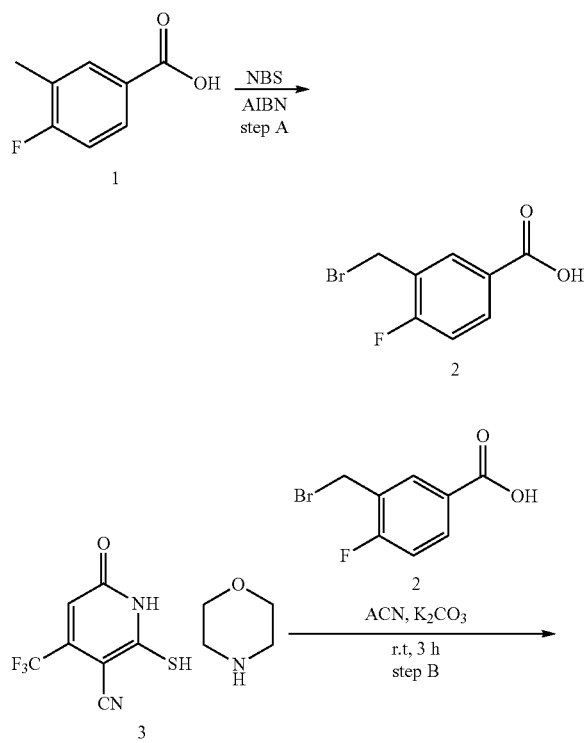

Step A: 3-(bromomethyl)-4-fluorobenzoic acid

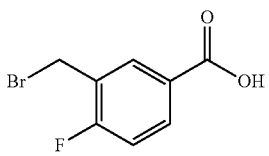 [SMILES: O=C(O)c1ccc(F)c(CBr)c1]

A mixture of 4-fluoro-3-methylbenzoic acid (500 mg, 3.25 mmol), NBS (867 mg, 4.87 mmol), AIBN (106 mg, 0.65 mmol) in CH$_3$CN (30 mL) was stirred at 80° C. for 18 h under argon. The mixture was cooled to room temperature, and removed the solvent under reduce pressure. The residue was purified by silica gel column chromatography, eluting with PE/EA=30%-50%, to get the title compound (600 mg) as a white solid.

Step B: 3-((3-cyano-6-oxo-4-(trifluoromethyl)-1,6-dihydropyridin-2-ylthio)methyl)-4-fluorobenzoic acid

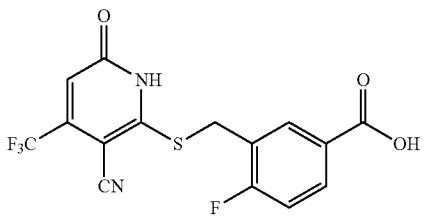 [SMILES: N#Cc1c(C(F)(F)F)cc(=O)[nH]c1SCc1cc(C(=O)O)ccc1F]

A mixture of 2-mercapto-6-oxo-4-(trifluoromethyl)-1,6-dihydropyridine-3-carbonitrile as a 1:1 morpholine salt (200 mg, 0.651 mmol), 3-(bromomethyl)-4-fluorobenzoic acid (182 mg, 0.782 mmol), K$_2$CO$_3$ (180 mg, 1.3 mmol) in CH$_3$CN (10 mL) was stirred at room temperature for 2 h. The mixture was poured into water (20 mL), acidified by addition of 1 N HCl to pH=3-5, and extracted with EtOAc (3×20 mL). The combined organic layers were washed with brine, dried over Na$_2$SO$_4$, filtered, and concentrated under reduced pressure. The residue was purified by prep-HPLC, eluting with MeOH/water=50%-80% (containing 0.1% HCOOH) to get the desired compound (84 mg) as a white solid.

$^1$H NMR (400 MHz, DMSO-d$_6$) δ: 13.16 (brs, 2H), 8.18 (dd, J=7.4, 2.3 Hz, 1H), 7.93 (ddd, J=8.5, 5.2, 2.2 Hz, 1H), 7.36 (dd, J=9.7, 8.9 Hz, 1H), 6.89 (s, 1H), 4.64 (s, 2H). LCMS (ESI$^-$): m/z 371.0 (M–H)$^-$.

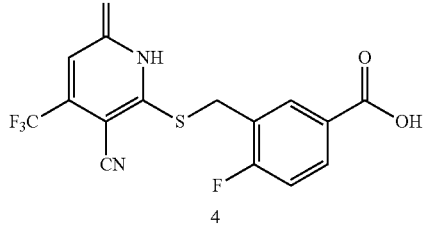

Example 20—Synthesis of 3-(((3-cyano-6-oxo-4-(trifluoromethyl)-1,6-dihydropyridin-2-yl)thio)methyl)-5-fluorobenzoic acid

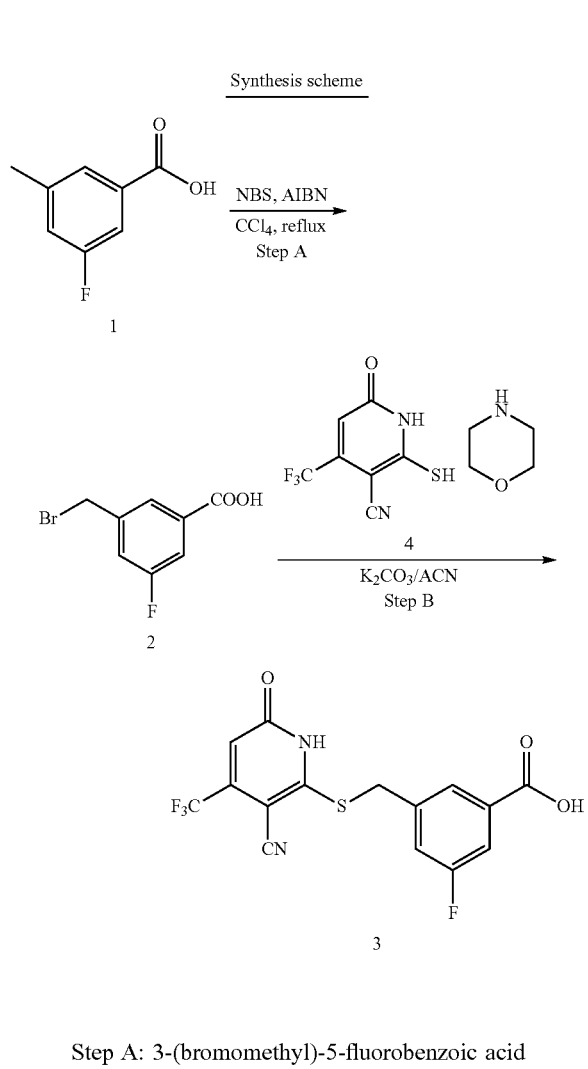

Step A: 3-(bromomethyl)-5-fluorobenzoic acid

To a solution of 3-fluoro-5-methylbenzoic acid (300 mg, 1.95 mmol) and NBS (416 mg, 2.34 mmol) in acetonitrile (10 mL) was added AIBN (64 mg, 0.39 mmol) at room temperature. The reaction was stirred at reflux for 3 h. TLC (EtOAc/PE=2:1, silica gel plate) showed complete consumption of the starting material after this time. The mixture was concentrated in vacuo. The residue was purified via column chromatography (PE/EA=1:1) to give the desired compound (300 mg) as a yellow solid which was directly used in the next step.

Step B: 3-(((3-cyano-6-oxo-4-(trifluoromethyl)-1,6-dihydropyridin-2-yl)thio)methyl)-5-fluorobenzoic acid

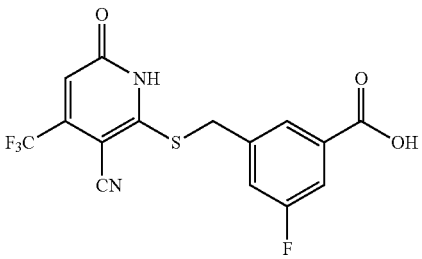 [SMILES: N#Cc1c(C(F)(F)F)cc(=O)[nH]c1SCc1cc(F)cc(C(=O)O)c1]

To a solution of 2-mercapto-6-oxo-4-(trifluoromethyl)-1,6-dihydropyridine-3-carbonitrile as a 1:1 morpholine salt (123 mg, 0.43 mmol) and 3-(bromomethyl)-5-fluorobenzoic acid (100 mg, 0.43 mmol) in CH$_3$CN (10 mL) was added K$_2$CO$_3$ (118 mg, 0.86 mmol) at room temperature. The resultant reaction mixture was stirred at room temperature for 1.5 h. TLC (10% MeOH/90% DCM, silica gel plate) showed complete consumption of the starting material after this time. The mixture was purified via reverse phase column chromatography (MeOH/H$_2$O=5%-80%) to give the desired compound (36 mg) as a white solid.

$^1$H NMR (400 MHz, DMSO-d$_6$) δ: 13.34 (s, 2H), 7.90 (s, 1H), 7.66 (d, J=8.9 Hz, 1H), 7.55 (dd, J=9.1, 1.3 Hz, 1H), 6.89 (s, 1H), 4.61 (s, 2H). LC-MS (ESI$^+$): m/z 373.0 (M+H)$^+$.

Example 21—Synthesis of 5-(((3-cyano-6-oxo-4-(trifluoromethyl)-1,6-dihydropyridin-2-yl)thio)methyl)-2-fluorobenzoic acid

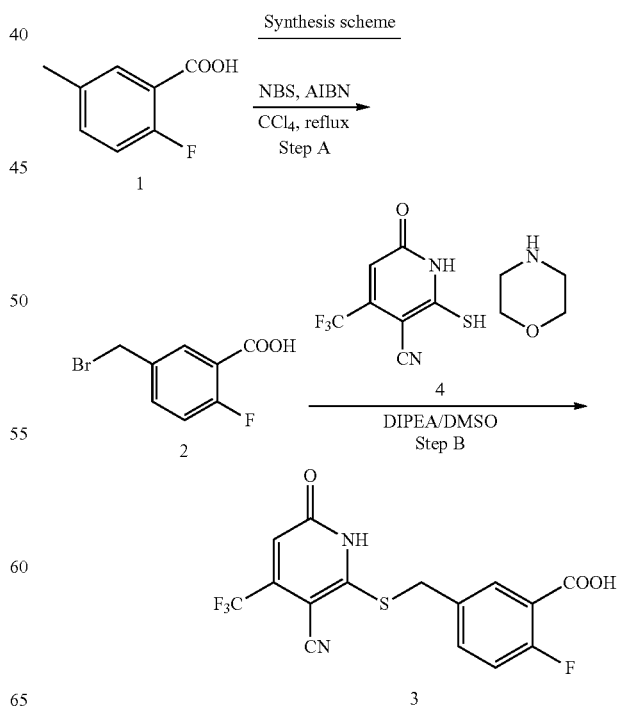

51

Step A: 5-(bromomethyl)-2-fluorobenzoic acid

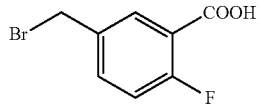

To a solution of 2-fluoro-5-methylbenzoic acid (1.0 g, 6.49 mmol) and NBS (1.7 g, 9.74 mmol) in CH$_3$CN (50 mL) was added AIBN (160 mg, 0.974 mmol) at room temperature. The reaction mixture was stirred at reflux for 12 h. TLC (EtOAc/PE=1:1, silica gel plate) showed complete consumption of the starting material after this time. The mixture was concentrated in vacuo. The residue was purified via column chromatography (PE/EA=1:1) to give the desired compound (981 mg) as a white solid, which was used in the next reaction without further purification.

Step B: 5-(((3-cyano-6-oxo-4-(trifluoromethyl)-1,6-dihydropyridin-2-yl)thio)methyl)-2-fluorobenzoic acid

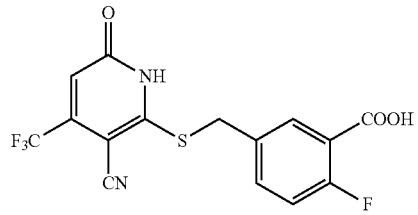 [SMILES: N#Cc1c(C(F)(F)F)cc(=O)[nH]c1SCc1ccc(F)c(C(=O)O)c1]

To a solution of 2-mercapto-6-oxo-4-(trifluoromethyl)-1,6-dihydropyridine-3-carbonitrile as a 1:1 morpholine salt (154 mg, 0.5 mmol) and 5-(bromomethyl)-2-fluorobenzoic acid (116.5 mg, 0.5 mmol) in DMSO (5 mL) was added DIPEA (129 mg, 1.0 mmol) at room temperature. The reaction mixture was stirred at room temperature for 1 h. TLC (10% MeOH/90% DCM, silica gel plate) showed complete consumption of the starting material after this time. The mixture was purified via reverse phase column chromatography (MeOH/H$_2$O=5%-80%) to give the desired compound (98.1 mg) as a pale yellow solid.

$^1$H NMR (400 MHz, DMSO-d$_6$) δ: 13.37 (s, 2H), 8.03 (dd, J=6.9, 1.9 Hz, 1H), 7.92-7.69 (m, 1H), 7.33 (dd, J=10.5, 8.8 Hz, 1H), 6.96 (s, 1H), 4.64 (s, 2H). LC-MS (ESI$^+$): m/z 373.0 (M+H)$^+$.

Example 22—Synthesis of 3-(((3-cyano-6-oxo-4-(trifluoromethyl)-1,6-dihydropyridin-2-yl)thio)methyl)-2-fluorobenzoic acid Synthesis scheme

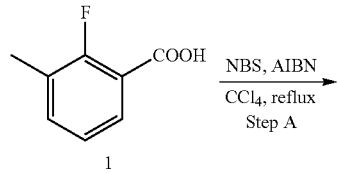

52

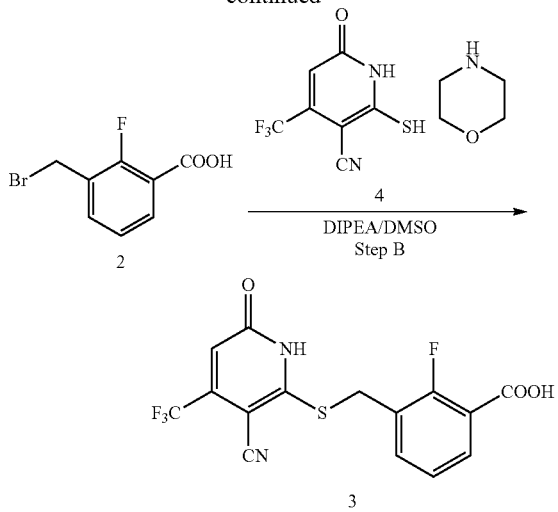

Step A: 3-(bromomethyl)-2-fluorobenzoic acid

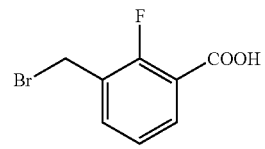

To a solution of 2-fluoro-3-methylbenzoic acid (1.0 g, 6.49 mmol) and NBS (1.7 g, 9.74 mmol) in CH$_3$CN (50 mL) was added AIBN (160 mg, 0.974 mmol) at room temperature. The reaction mixture was stirred at reflux for 12 h. TLC (EtOAc/PE=1:1, silica gel plate) showed complete consumption of the starting material after this time. The mixture was concentrated in vacuo. The residue was purified via column chromatography (PE/EA=1:1) to give the desired compound (891 mg) as a white solid, which was used in the next reaction without further purification.

Step B: 3-(((3-cyano-6-oxo-4-(trifluoromethyl)-1,6-dihydropyridin-2-yl)thio)methyl)-2-fluorobenzoic acid

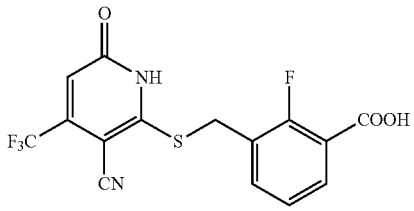 [SMILES: N#Cc1c(C(F)(F)F)cc(=O)[nH]c1SCc1cccc(C(=O)O)c1F]

To a solution of 2-mercapto-6-oxo-4-(trifluoromethyl)-1,6-dihydropyridine-3-carbonitrile as a 1:1 morpholine salt (200 mg, 0.651 mmol) and 3-(bromomethyl)-2-fluorobenzoic acid (151.8 mg, 0.651 mmol) in DMSO (5 mL) was added DIPEA (84 mg, 0.651 mmol) at room temperature. The reaction mixture was stirred at room temperature for 1 h. TLC (10% MeOH/90% DCM, silica gel plate) showed complete consumption of the starting material after this time. The mixture was purified via reverse phase column chromatography (MeOH/H₂O=5%-80%) to give the desired compound (140.1 mg) as a pale white solid.

¹H NMR (400 MHz, DMSO-d₆) δ: 13.33 (s, 2H), 7.91-7.72 (m, 2H), 7.25 (t, J=7.7 Hz, 1H), 6.91 (s, 1H), 4.61 (s, 2H). LC-MS (ESI⁺): m/z 373.0 (M+H)⁺.

Example 23—Synthesis of 3-(((3-cyano-6-oxo-4-(thiophen-2-yl)-1,6-dihydropyridin-2-yl)thio)methyl) benzoic acid

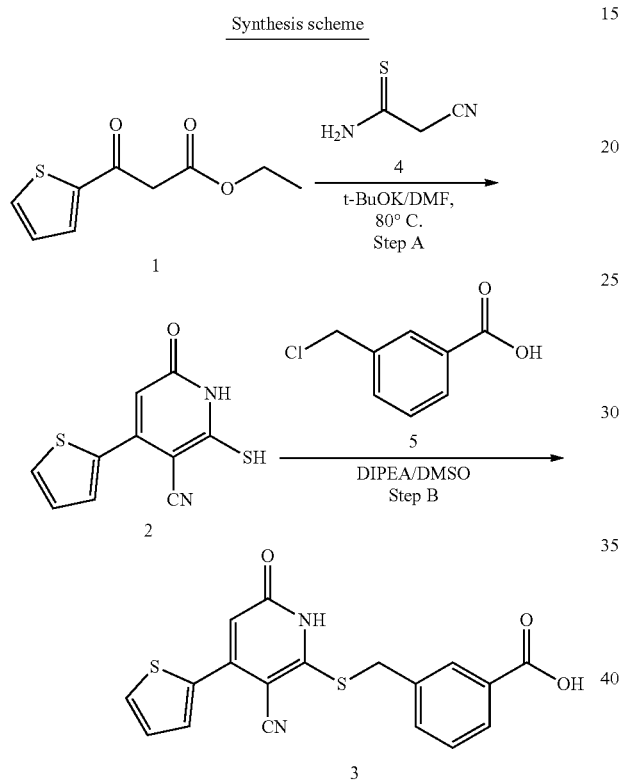

Step A: 2-mercapto-6-oxo-4-(thiophen-2-yl)-1,6-dihydropyridine-3-carbonitrile

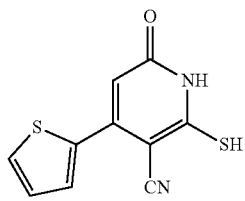 [SMILES: N#Cc1c(-c2cccs2)cc(=O)[nH]c1S]

To a solution of ethyl 3-oxo-3-(thiophen-2-yl)propanoate (1.0 g, 5.05 mmol) and 2-cyanoethanethioamide (555 mg, 5.55 mmol) in DMF (50 mL) was added t-BuOK (2.83 g, 25.3 mmol) at room temperature. The reaction mixture was heated at 80° C. for 4 h under N₂. TLC (50% PE/50% EtOAc, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The residue was purified via column chromatography (DCM/MeOH=10:1) to give the desired compound (238.1 mg) as a yellow solid. LC-MS (ESI⁺): m/z 235.0 (M+H)⁺.

Step B: 3-(((3-cyano-6-oxo-4-(thiophen-2-yl)-1,6-dihydropyridin-2-yl)thio)methyl)benzoic acid

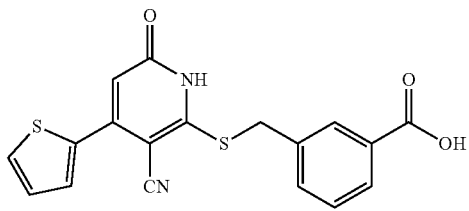 [SMILES: N#Cc1c(-c2cccs2)cc(=O)[nH]c1SCc1cccc(C(=O)O)c1]

To a solution of 2-mercapto-6-oxo-4-(thiophen-2-yl)-1,6-dihydropyridine-3-carbonitrile (234 mg, 1.0 mmol) and 3-(chloromethyl)benzoic acid (171 mg, 1.0 mmol) in DMSO (5 mL) was added DIPEA (189 mg, 1.5 mmol) at room temperature. The reaction mixture was stirred at room temperature for 1 h. TLC (10% MeOH/90% DCM, silica gel plate) showed complete consumption of the starting material after this time. The mixture was cooled to room temperature, adjusted to pH=5.0, and extracted with EtOAc (2×50 mL). The combined organic layers were washed with brine, dried and concentrated in vacuo. The mixture was purified via reverse phase column chromatography (MeOH/H₂O=5%-80%) to give the desired compound (100.2 mg) as a yellow solid.

¹H NMR (400 MHz, DMSO-d₆) δ: 12.89 (brs, 1H), 12.68 (brs, 1H), 8.08 (s, 1H), 7.84-7.77 (m, 3H), 7.74 (d, J=7.7 Hz, 1H), 7.44 (t, J=7.7 Hz, 1H), 7.26-7.19 (m, 1H), 7.10 (s, 1H), 4.66 (s, 2H). LC-MS (ESI⁺): m/z 369.1 (M+H)⁺.

Example 24—Synthesis of 3-(((3-cyano-4-cyclohexyl-6-oxo-1,6-dihydropyridin-2-yl)thio)methyl) benzoic acid

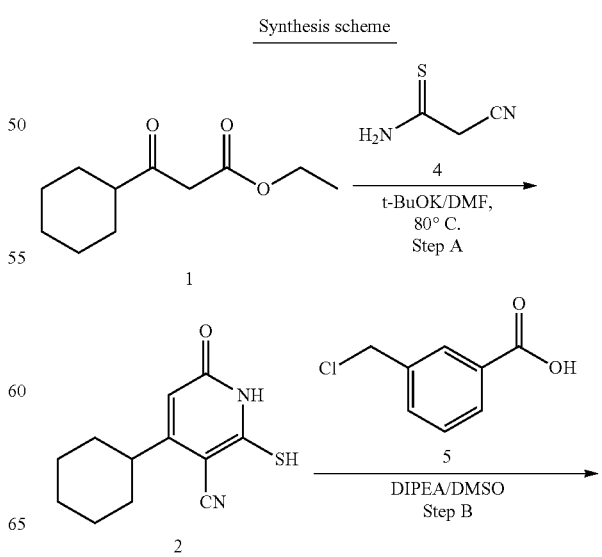

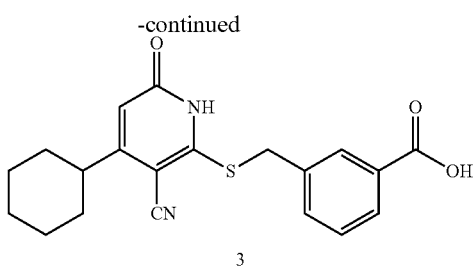

3

Step A: 4-cyclohexyl-2-mercapto-6-oxo-1,6-dihydropyridine-3-carbonitrile

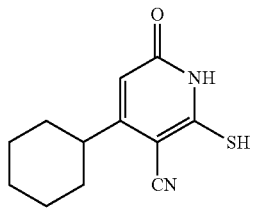 [SMILES: N#Cc1c(C2CCCCC2)cc(=O)[nH]c1S]

To a solution of ethyl 3-cyclohexyl-3-oxopropanoate (1.0 g, 5.05 mmol) and 2-cyanoethanethioamide (556 mg, 5.56 mmol) in DMF (50 mL) was added t-BuOK (2.83 g, 25.3 mmol) at room temperature. The reaction mixture was heated at 80° C. for 4 h under $N_2$. TLC (50% PE/50% EtOAc, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The residue was purified via column chromatography (DCM/MeOH=10:1) to give the desired compound (178.1 mg) as a yellow solid. LC-MS (ESI$^+$): m/z 235.1 (M+H)$^+$.

Step B: 3-(((3-cyano-4-cyclohexyl-6-oxo-1,6-dihydropyridin-2-yl)thio)methyl)benzoic acid

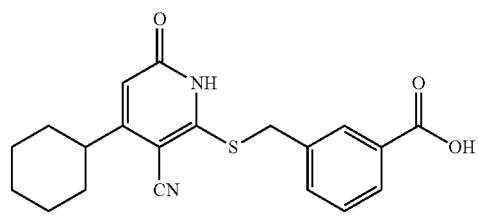 [SMILES: N#Cc1c(C2CCCCC2)cc(=O)[nH]c1SCc1cccc(C(=O)O)c1]

To a solution of 4-cyclohexyl-2-mercapto-6-oxo-1,6-dihydropyridine-3-carbonitrile (178 mg, 0.761 mmol) and 3-(chloromethyl)benzoic acid (130.1 mg, 0.761 mmol) in DMSO (5 mL) was added DIPEA (147.2 mg, 1.14 mmol) at room temperature. The reaction mixture was stirred at room temperature for 1 h. TLC (10% MeOH/90% DCM, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The mixture was purified via reverse phase column chromatography (MeOH/H$_2$O=5%-80%) to give the desired compound (51.7 mg) as a white solid.

$^1$H NMR (400 MHz, DMSO-d$_6$) δ: 12.90 (brs, 2H), 8.04 (s, 1H), 7.80 (d, J=7.8 Hz, 1H), 7.66 (d, J=7.7 Hz, 1H), 7.43 (t, J=7.7 Hz, 1H), 6.49 (s, 1H), 4.54 (s, 2H), 2.58 (t, J=11.3 Hz, 1H), 1.72 (dd, J=38.6, 9.5 Hz, 5H), 1.51-1.15 (m, 5H). LC-MS (ESI$^+$): m/z 369.2 (M+H)$^+$.

Example 25—Synthesis of 3-(((3-cyano-6-oxo-4-(m-tolyl)-1,6-dihydropyridin-2-yl)thio)methyl)benzoic acid Synthesis scheme

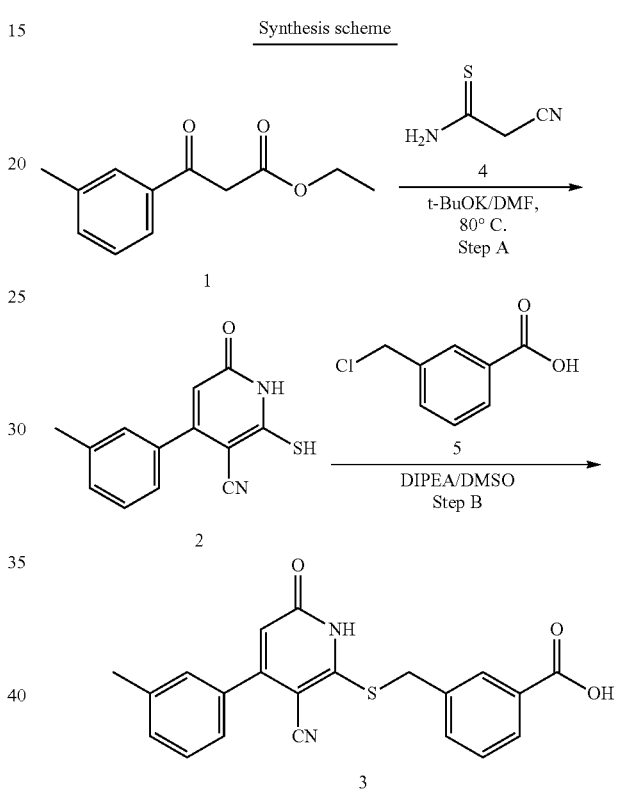

Step A: 2-mercapto-6-oxo-4-(m-tolyl)-1,6-dihydropyridine-3-carbonitrile

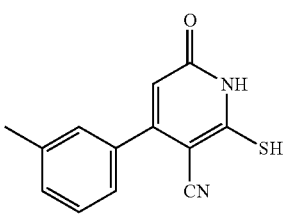 [SMILES: Cc1cccc(-c2cc(=O)[nH]c(S)c2C#N)c1]

To a solution of ethyl 3-oxo-3-(m-tolyl)propanoate (1.1 g, 5.34 mmol) and 2-cyanoethanethioamide (801 mg, 8.01 mmol) in DMF (50 mL) was added t-BuOK (2.99 g, 26.7 mmol) at room temperature. The reaction mixture was heated at 80° C. for 12 h under $N_2$. TLC (50% PE/50% EtOAc, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The residue was purified via column chromatography (DCM/MeOH=10:1) to give the desired compound (198.1.1 mg) as a yellow solid. LC-MS (ESI⁺): m/z 243.1 (M+H)⁺.

Step B: 3-(((3-cyano-6-oxo-4-(m-tolyl)-1,6-dihydro-pyridin-2-yl)thio)methyl)benzoic acid

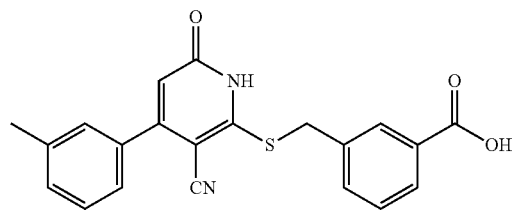 [SMILES: Cc1cccc(-c2cc(=O)[nH]c(SCc3cccc(C(=O)O)c3)c2C#N)c1]

To a solution of 2-mercapto-6-oxo-4-(m-tolyl)-1,6-dihydropyridine-3-carbonitrile (200 mg, 0.826 mmol) and 3-(chloromethyl)benzoic acid (169.6 mg, 0.992 mmol) in DMSO (5 mL) was added DIPEA (128 mg, 0.992 mmol) at room temperature. The reaction mixture was stirred at room temperature for 1 h. TLC (10% MeOH/90% DCM, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The mixture was purified via reverse phase column chromatography (MeOH/H$_2$O=5%-80%) to give the desired compound (35.8 mg) as a white solid.

¹H NMR (400 MHz, DMSO-d$_6$) δ: 12.94 (s, 2H), 8.09 (s, 1H), 7.80 (dd, J=19.9, 4.7 Hz, 3H), 7.72 (d, J=7.8 Hz, 1H), 7.42 (dt, J=17.7, 7.9 Hz, 2H), 7.32 (d, J=7.4 Hz, 1H), 7.14 (s, 1H), 4.69 (s, 2H), 2.39 (s, 3H). LC-MS (ESI⁺): m/z 377.1 (M+H)⁺.

Example 26—Synthesis of 3-(((3-cyano-6-oxo-1,6-dihydro-[4,4'-bipyridin]-2-yl)thio)methyl)benzoic acid Synthesis scheme

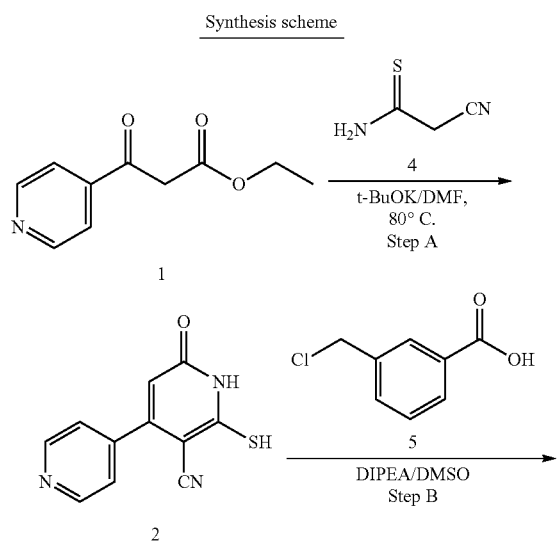

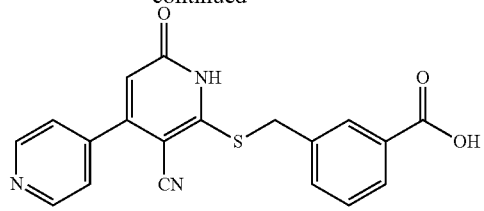

Step A: 2-mercapto-6-oxo-1,6-dihydro-[4,4'-bipyridine]-3-carbonitrile

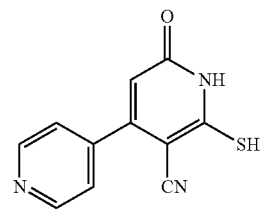 [SMILES: N#Cc1c(-c2ccncc2)cc(=O)[nH]c1S]

To a solution of ethyl 3-oxo-3-(pyridin-4-yl)propanoate (1.0 g, 5.2 mmol) and 2-cyanoethanethioamide (569.4 mg, 5.69 mmol) in DMF (50 mL) was added t-BuOK (2.91 g, 26 mmol) at room temperature. The reaction mixture was heated at 90° C. for 4 h under N$_2$. TLC (50% PE/50% EtOAc, silica gel plate) showed complete consumption of the starting material after this time. The mixture was concentrated in vacuo. The residue was purified via reverse phase column chromatography (MeOH/H$_2$O=5%-80%) to give the desired compound (75.1 mg) as a yellow solid. LC-MS (ESI⁺): m/z 230.1 (M+H)⁺.

Step B: 3-(((3-cyano-6-oxo-1,6-dihydro-[4,4'-bipyridin]-2-yl)thio)methyl)benzoic acid

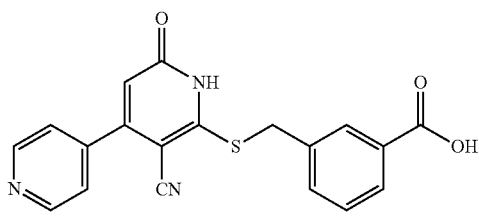 [SMILES: N#Cc1c(-c2ccncc2)cc(=O)[nH]c1SCc1cccc(C(=O)O)c1]

To a solution of 2-mercapto-6-oxo-1,6-dihydro-[4,4'-bipyridine]-3-carbonitrile (170 mg, 0.742 mmol) and 3-(chloromethyl)benzoic acid (152.3 mg, 0.891 mmol) in DMSO (5 mL) was added DIPEA (143.6 mg, 1.123 mmol) at room temperature. The reaction mixture was stirred at room temperature for 1 h. TLC (10% MeOH/90% DCM, silica gel plate) showed complete consumption of the starting material after this time. The mixture was cooled to room temperature, adjusted to pH=5.0, and extracted with EtOAc (2×50 mL). The combined organic layers were washed with brine, dried and concentrated in vacuo. The mixture was purified via reverse phase column chromatography (MeOH/H$_2$O=5%-80%) to give the desired compound (65.1 mg) as a yellow solid.

¹H NMR (400 MHz, DMSO-d₆) δ: 12.94 (s, 2H), 8.69 (s, 2H), 8.11 (d, J=23.6 Hz, 1H), 7.93 (d, J=5.0 Hz, 2H), 7.80 (d, J=7.7 Hz, 1H), 7.70 (d, J=7.7 Hz, 1H), 7.43 (t, J=7.7 Hz, 1H), 7.04 (s, 1H), 4.65 (s, 2H). LC-MS (ESI⁺): m/z 364.0 (M+H)⁺.

Example 27—Synthesis of 2-(3-cyano-6-oxo-4-(trifluoromethyl)-1,6-dihydropyridin-2-ylthio)-2-fluoroacetic acid

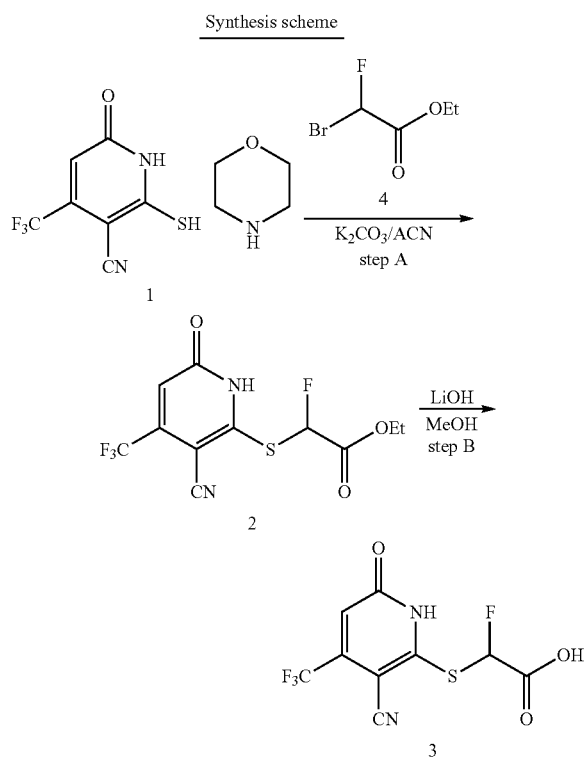

Step A: ethyl 2-(3-cyano-6-oxo-4-(trifluoromethyl)-1,6-dihydropyridin-2-ylthio)-2-fluoroacetate

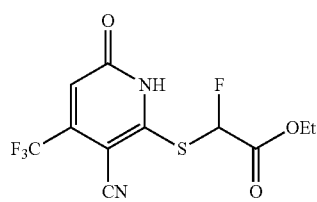 [SMILES: CCOC(=O)C(F)Sc1[nH]c(=O)cc(C(F)(F)F)c1C#N]

To a mixture of 2-mercapto-6-oxo-4-(trifluoromethyl)-1,6-dihydropyridine-3-carbonitrile as a 1:1 morpholine salt (500 mg, 1.63 mmol), ethyl 2-bromo-2-fluoroacetate (361 mg, 1.95 mmol) in CH₃CN (10 mL) was added K₂CO₃ (450 mg, 3.26 mmol). The reaction mixture was stirred at room temperature for 2 h. The mixture was concentrated in vacuo. The residue was dissolved in water (20 mL), and acidified to pH=3-5 by addition of 1 N HCl, and extracted with EtOAc (3×20 mL), the combined organic layers were concentrated in vacuo. The residue was purified via column chromatography (MeOH/DCM=3%) to give of title compound (324 mg) as a yellow solid. LCMS (ESI⁺): m/z 325.0 (M+H)⁺.

Step B: 2-(3-cyano-6-oxo-4-(trifluoromethyl)-1,6-dihydropyridin-2-ylthio)-2-fluoroacetic acid

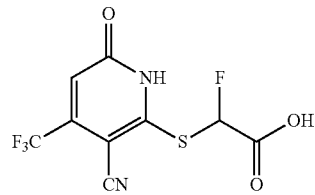

To a solution of ethyl 2-(3-cyano-6-oxo-4-(trifluoromethyl)-1,6-dihydropyridin-2-ylthio)-2-fluoroacetate(324 mg, 1 mmol) in THF (10 mL) was added LiOH (84 mg, 2 mmol) in water (1 mL). Then the mixture was stirred at room temperature for 2 h. The mixture was poured into water (20 mL) and extracted with ether (2×30 mL). The organic layers were discarded. The aqueous layer was acidified to pH=3-5 by addition of 1 N HCl, and extracted with EtOAc (3×20 mL). The combined organic layers were washed with brine, dried over Na₂SO₄, filtered, and concentrated under reduce pressure to give desired compound (200 mg) as a white solid.

¹H NMR (400 MHz, DMSO-d₆) δ: 13.85 (br. s., 1H), 7.12 (d, J=50.4 Hz, 1H), 7.07 (s, 1H). LC-MS (ESI⁺): m/z 296.9 (M+H)⁺.

Example 28—Synthesis of 2-((3-cyano-6-oxo-4-(trifluoromethyl)-1,6-dihydropyridin-2-yl)thio)-2,2-difluoroacetic acid Synthesis scheme

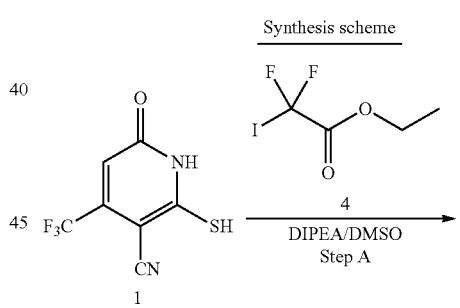

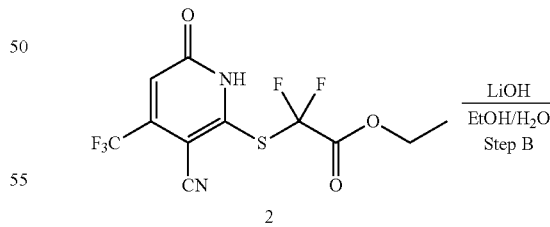

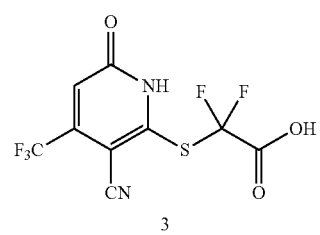

Step A: ethyl 2-((3-cyano-6-oxo-4-(trifluoromethyl)-1,6-dihydropyridin-2-yl)thio)-2,2-difluoroacetate

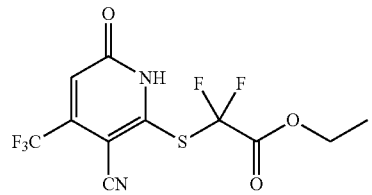 [SMILES: CCOC(=O)C(F)(F)Sc1[nH]c(=O)cc(C(F)(F)F)c1C#N]

To a solution of 2-mercapto-6-oxo-4-(trifluoromethyl)-1,6-dihydropyridine-3-carbonitrile (1 g, 4.54 mmol) and ethyl 2,2-difluoro-2-iodoacetate (1.72 g, 6.82 mmol) in DMSO (30 mL) was added DIPEA (880 mg, 6.82 mmol) at room temperature. The reaction mixture was stirred at 75° C. for 12 h in a sealed bottle. TLC (10% MeOH/90% DCM, silica gel plate) showed complete consumption of the starting material after this time. The mixture was adjusted to pH=5, extracted with EtOAc (2×50 mL), washed with brine, dried and concentrated in vacuo. The residue was purified via column chromatography (DCM/MeOH=10:1) to give the desired compound (188 mg) as a yellow solid.

LC-MS (ESI$^+$): m/z 343.0 (M+H)$^+$.

Step B: 2-((3-cyano-6-oxo-4-(trifluoromethyl)-1,6-dihydropyridin-2-yl)thio)-2,2-difluoroacetic acid

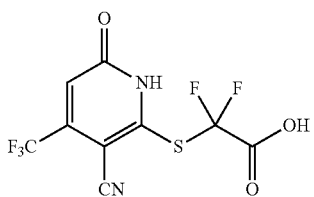 [SMILES: N#Cc1c(C(F)(F)F)cc(=O)[nH]c1SC(F)(F)C(=O)O]

To a solution of ethyl 2-((3-cyano-6-oxo-4-(trifluoromethyl)-1,6-dihydropyridin-2-yl)thio)-2,2-difluoroacetate (188 mg, 0.550 mmol) in EtOH (10 mL) and H$_2$O (1 mL) was added LiOH (34.6 mg, 0.825 mmol) at room temperature. The reaction mixture was stirred at 60° C. for 2 h. TLC (10% MeOH/90% DCM, silica gel plate) showed complete consumption of the starting material after this time. The mixture was adjusted to pH=5, extracted with EtOAc (2×50 mL), washed with brine, dried and concentrated in vacuo. The residue was purified via reverse phase column chromatography (MeOH/H$_2$O=5%-80%) to give the desired compound (18.8 mg) as a yellow solid.

$^1$H NMR (400 MHz, DMSO-d$_6$) δ: 7.14 (s, 1H). LC-MS (ESI$^+$): m/z 315.0 (M+H)$^+$.

Example 29—Synthesis of 3-(((3-cyano-6-oxo-4-(p-tolyl)-1,6-dihydropyridin-2-yl)thio)methyl)benzoic acid Synthesis scheme

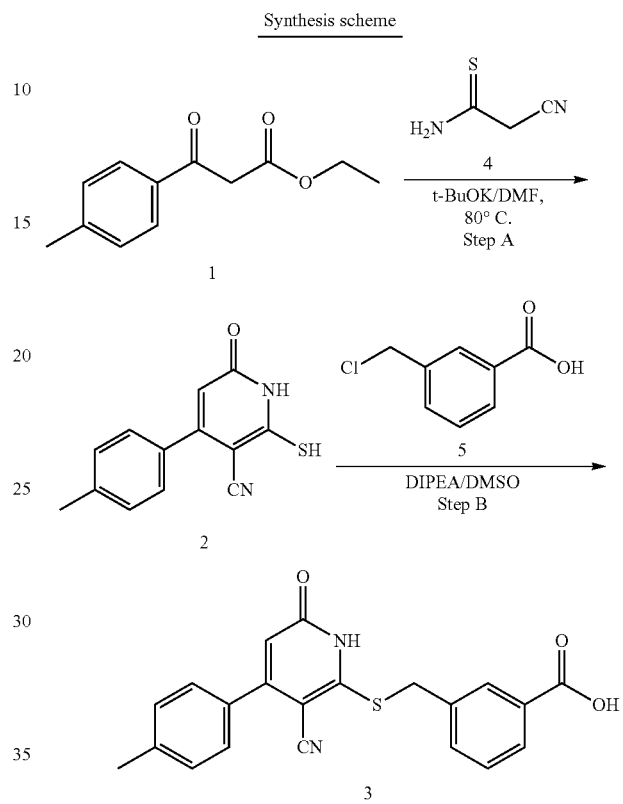

Step A: 2-mercapto-6-oxo-4-(p-tolyl)-1,6-dihydropyridine-3-carbonitrile

To a solution of ethyl 3-oxo-3-(p-tolyl)propanoate (1.5 g, 7.28 mmol) and 2-cyanoethanethioamide (946.6 mg, 9.47 mmol) in DMF (50 mL) was added t-BuOK (4.07 g, 36.4 mmol) at room temperature. The reaction mixture was heated at 90° C. for 4 h under N$_2$. TLC (50% PE/50% EtOAc, silica gel plate) showed complete consumption of the starting material after this time. The mixture was concentrated in vacuo. The residue was purified via reverse phase column chromatography (MeOH/H$_2$O=5%-80%) to give the desired compound (381 mg) as a yellow solid. LC-MS (ESI$^+$): m/z 243.0 (M+H)$^+$.

Step B: 3-(((3-cyano-6-oxo-4-(p-tolyl)-1,6-dihydro-pyridin-2-yl)thio)methyl)benzoic acid

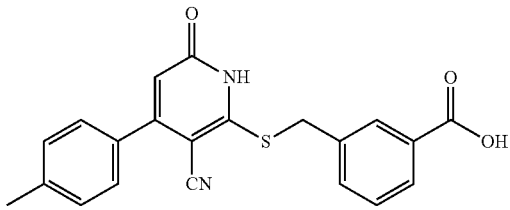 [SMILES: Cc1ccc(-c2cc(=O)[nH]c(SCc3cccc(C(=O)O)c3)c2C#N)cc1]

To a solution of 2-mercapto-6-oxo-4-(p-tolyl)-1,6-dihydropyridine-3-carbonitrile (250 mg, 1.03 mmol) and 3-(chloromethyl)benzoic acid (230 mg, 1.34 mmol) in DMSO (5 mL) was added DIPEA (200 mg, 1.55 mmol) at room temperature. The reaction mixture was stirred at room temperature for 1 h. TLC (10% MeOH/90% DCM, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The mixture was purified via reverse phase column chromatography (MeOH/H$_2$O=5%-80%) to give the desired compound (79.3 mg) as a yellow solid.

$^1$H NMR (400 MHz, DMSO-d$_6$) δ: 13.08 (brs, 1H), 12.75 (brs, 1H), 8.08 (s, 1H), 7.91 (d, J=8.2 Hz, 2H), 7.82 (d, J=7.8 Hz, 1H), 7.71 (d, J=7.9 Hz, 1H), 7.44 (t, J=7.7 Hz, 1H), 7.33 (d, J=8.0 Hz, 2H), 7.14 (s, 1H), 4.69 (s, 2H), 2.38 (s, 3H). LC-MS (ESI$^+$): m/z 377.1 (M+H)$^+$.

Example 30—Synthesis of 3-(((3-cyano-5-fluoro-6-oxo-4-phenyl-1,6-dihydropyridin-2-yl)thio)methyl)benzoic acid Synthesis scheme

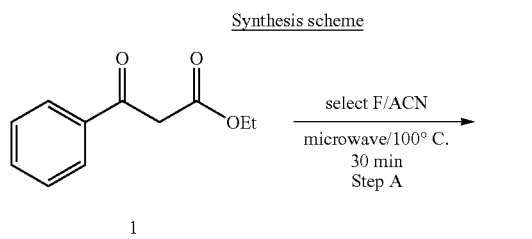

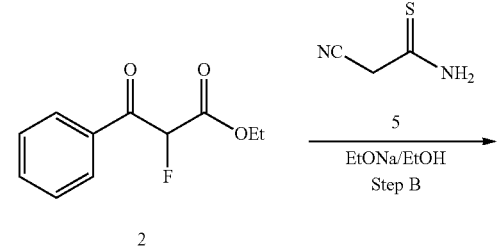

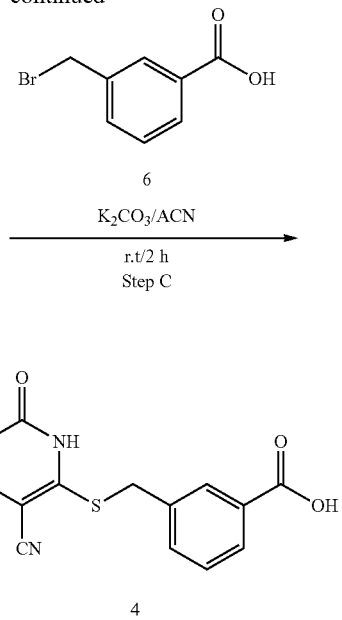

Step A: ethyl 2-fluoro-3-oxo-3-phenylpropanoate

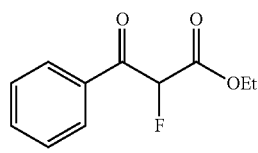 [SMILES: CCOC(=O)C(F)C(=O)c1ccccc1]

A mixture of ethyl 3-oxo-3-phenylpropanoate (1 g, 5.2 mmol), 1-chloromethyl-4-fluoro-1,4-diazoniabicyclo[2.2.2]octane bis(tetrafluoroborate) (1.843 g, 5.2 mmol) in acetonitrile (5 mL) was stirred under microwave at 100° C. for 45 min. The solvent was removed under reduced pressure. The residue was poured into water (20 mL) and extracted with EtOAc (3×20 mL). The combined organic layers were washed with brine, dried over Na$_2$SO$_4$, filtered, and concentrated under reduced pressure. The residue was purified by silica gel column chromatography, eluting with PE/EA=10:1 to get the desired compound (880 mg) as a colorless oil. LC-MS(ESI$^+$): m/z 211.1 (M+H)$^+$ Step B: 5-fluoro-2-mercapto-6-oxo-4-phenyl-1,6-dihydropyridine-3-carbonitrile

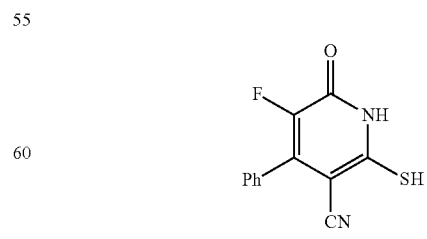

To a solution of 2-cyanoethanethioamide (340 mg, 3.4 mmol) in EtOH (10 mL) was added EtONa (3.1 mL, 4.65 mmol, 1.5 M in EtOH) at 60° C. Then the mixture was stirred at 60° C. for 1 h. Then ethyl 2-fluoro-3-oxo-3-phenylpropanoate (650 mg, 3.1 mmol) was added. The mixture was warmed to 90° C. and stirred for 3 h. The reaction mixture was cooled to room temperature, poured into water (50 mL), and extracted with EtOAc (3×50 mL). The organic layers were discarded. The aqueous layer was acidified to pH=3-5 by addition of 1 N HCl and extracted with EtOAc (3×50 mL). The combined organic layers were washed with brine, dried over $Na_2SO_4$, filtered, and evaporated in vacuo to get the crude title compound (500 mg) which was directly used in the next step. LC-MS (ESI$^+$): m/z 247.0 (M+H)$^+$.

Step C: 3-(((3-cyano-5-fluoro-6-oxo-4-phenyl-1,6-dihydropyridin-2-yl)thio)methyl)benzoic acid

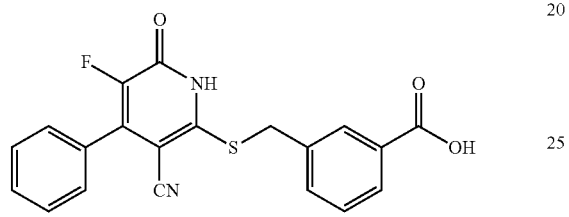

A mixture of 5-fluoro-2-mercapto-6-oxo-4-phenyl-1,6-dihydropyridine-3-carbonitrile (250 mg, 0.506 mmol), 3-(bromomethyl)benzoic acid (120 mg, 0.556 mmol), and $K_2CO_3$ (210 mg, 1.52 mmol) in acetonitrile (5 mL) was stirred at room temperature for 2 h. The solvent was removed under reduced pressure. The residue was poured into water (20 mL) and extracted with EtOAc (3×20 mL). The combined organic layers were washed with brine, dried over $Na_2SO_4$, filtered, and concentrated under reduced pressure. The residue was purified by silica gel column chromatography, eluting with MeOH/DCM=1/10, to get the desired compound (50 mg) as a white solid.

$^1$H NMR (400 MHz, DMSO-$d_6$) δ: 13.40 (brs, 1H), 13.05 (brs, 1H), 8.00 (s, 1H), 7.84 (d, J=7.63 Hz, 1H), 7.71 (d, J=7.32 Hz, 1H), 7.51-7.57 (m, 3H), 7.44-7.50 (m, 3H), 4.58 (s, 2H). LC-MS (ESI$^+$): m/z 380.9 (M+H)$^+$ Example 31—Synthesis of 3-((3-cyano-5-methyl-6-oxo-4-phenyl-1,6-dihydropyridin-2-ylthio)methyl)benzoic acid Synthesis scheme

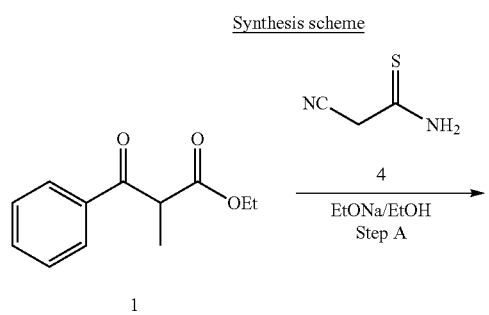

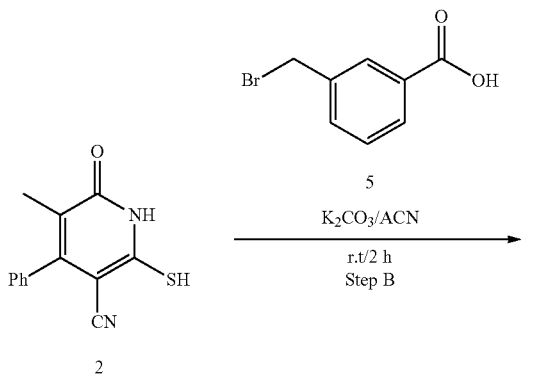

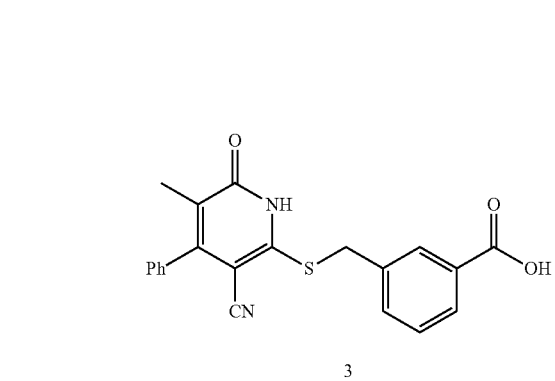

Step A: 2-mercapto-5-methyl-6-oxo-4-phenyl-1,6-dihydropyridine-3-carbonitrile

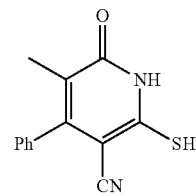

To a solution of 2-cyanoethanethioamide (534 mg, 5.335 mmol) in EtOH (10 mL) was added EtONa (4.6 ml, 7.3 mmol, 1.5 M in EtOH) at 60° C. Then the mixture was stirred at 60° C. for 1 h. Then ethyl 2-methyl-3-oxo-3-phenylpropanoate (1 g, 4.85 mmol) was added. The mixture was warmed to 90° C. and stirred for 3 h. The reaction mixture was cooled to room temperature, poured into water (50 mL), and extracted with EtOAc (3×50 ml). The organic layers were discarded. The aqueous layer was acidified to pH=3-5 by addition of 1 N HCl and extracted with EtOAc (3×50 mL), the combined organic layers were washed with brine, dried over $Na_2SO_4$, filtered, and evaporated in vacuo to get the crude title compound (600 mg) which was directly used in the next step. LC-MS (ESI$^+$): m/z 243.0 (M+H)$^+$.

Step B: 3-((3-cyano-5-methyl-6-oxo-4-phenyl-1,6-dihydropyridin-2-ylthio)methyl)benzoic acid

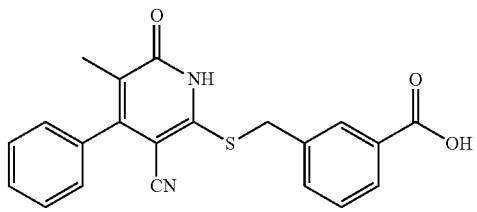 [SMILES: Cc1c(-c2ccccc2)c(C#N)c(SCc2cccc(C(=O)O)c2)[nH]c1=O]

A mixture of 2-mercapto-5-methyl-6-oxo-4-phenyl-1,6-dihydropyridine-3-carbonitrile (600 mg, 0.74 mmol, 30% purity), 3-(bromomethyl)benzoic acid (160 mg, 0.74 mmol), and $K_2CO_3$ (306 mg, 2.22 mmol) in acetonitrile (10 ml) was stirred at room temperature for 2 h. The solvent was removed under reduced pressure. The residue was poured into water (20 mL) and extracted with EtOAc (3×20 ml). The combined organic layers were washed with brine, dried over $Na_2SO_4$, filtered, and concentrated under reduced pressure. The residue was purified by prep HPLC, eluting with MeOH/water=53% (containing 0.1% HCOOH), get the desired compound (70 mg) as a white solid.

$^1H$ NMR (400 MHz, DMSO-$d_6$) δ: 12.81 (brs, 1H), 8.02 (s, 1H), 7.82 (d, J=7.93 Hz, 1H), 7.71 (d, J=7.63 Hz, 1H), 7.37-7.57 (m, 4H), 7.28 (d, J=6.41 Hz, 2H), 4.58 (s, 2H), 1.80 (s, 3H). LC-MS (ESI+): m/z 377.0 (M+H)+

Example 32—Synthesis of 3-(((3'-cyano-6'-oxo-1', 6'-dihydro-[2,4'-bipyridin]-2'-yl)thio)methyl)benzoic acid Synthesis scheme

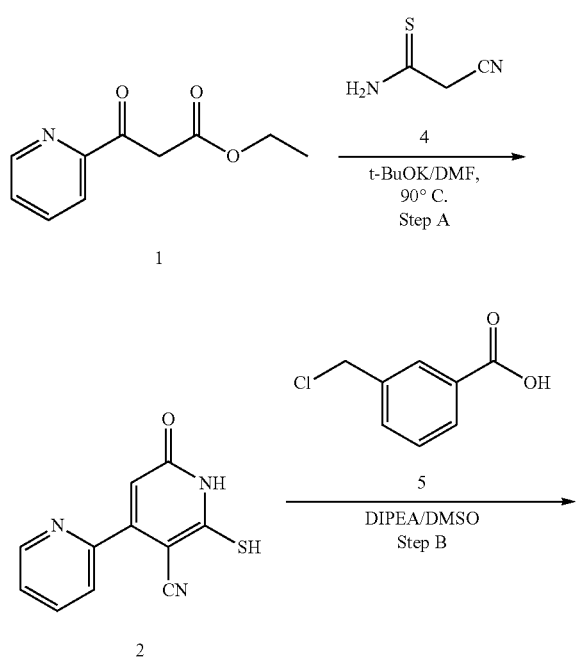

Step A: 2'-mercapto-6'-oxo-1',6'-dihydro-[2,4'-bipyridine]-3'-carbonitrile

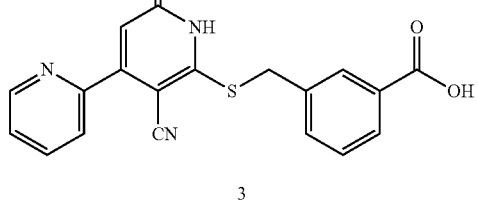

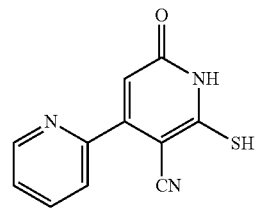 [SMILES: N#Cc1c(-c2ccccn2)cc(=O)[nH]c1S]

To a solution of ethyl 3-oxo-3-(pyridin-2-yl)propanoate (1 g, 5.2 mmol) and 2-cyanoethanethioamide (569.4 mg, 5.7 mmol) in DMF (50 mL) was added t-BuOK (2.91 g, 26 mmol) at room temperature. The reaction mixture was heated at 90° C. for 4 h under $N_2$. TLC (50% PE/50% EtOAc, silica gel plate) showed complete consumption of the starting material after this time. The mixture was concentrated in vacuo. The residue was purified via reverse phase column chromatography (MeOH/$H_2O$=5%-80%) to give the desired compound (89.1 mg) as a black solid. LC-MS (ESI+): m/z 230.1 (M+H)+.

Step B: 3-(((3'-cyano-6'-oxo-1',6'-dihydro-[2,4'-bipyridin]-2'-yl)thio)methyl)benzoic acid

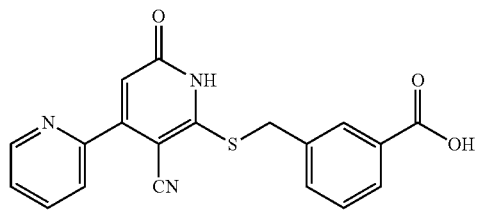 [SMILES: N#Cc1c(-c2ccccn2)cc(=O)[nH]c1SCc1cccc(C(=O)O)c1]

To a solution of 2'-mercapto-6'-oxo-1',6'-dihydro-[2,4'-bipyridine]-3'-carbonitrile (180 mg, 0.786 mmol) and 3-(chloromethyl)benzoic acid (174.7 mg, 1.02 mmol) in DMSO (5 mL) was added DIPEA (152.1 mg, 1.18 mmol) at room temperature. The reaction mixture was stirred at room temperature for 1 h. TLC (10% MeOH/90% DCM, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The mixture was purified via reverse phase column chromatography (MeOH/$H_2O$=5%-80%) to give the desired compound (20.8 mg) as a yellow solid.

¹H NMR (400 MHz, DMSO-d₆) δ: 12.79 (s, 2H), 8.73 (d, J=4.6 Hz, 1H), 8.06 (s, 1H), 8.00 (td, J=7.8, 1.6 Hz, 1H), 7.90-7.80 (m, 2H), 7.76 (d, J=7.6 Hz, 1H), 7.55 (dd, J=7.2, 5.1 Hz, 1H), 7.46 (t, J=7.7 Hz, 1H), 6.77 (s, 1H), 4.62 (s, 2H). LC-MS (ESI⁺): m/z 363.9 (M+H)⁺.

Example 33—Synthesis of 6-(((3-cyano-6-oxo-4-phenyl-1,6-dihydropyridin-2-yl)thio)methyl)picolinic acid Synthesis scheme

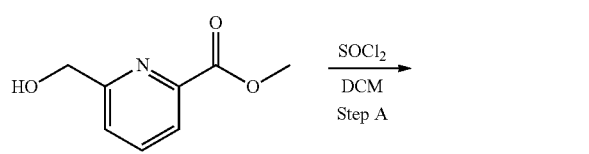

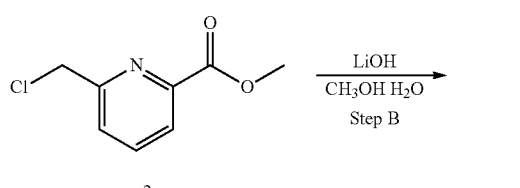

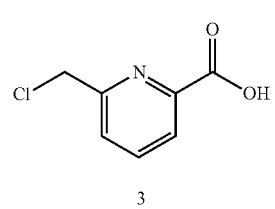

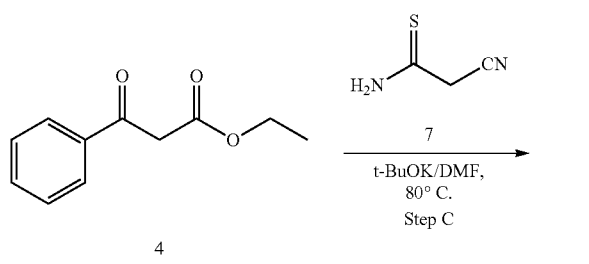

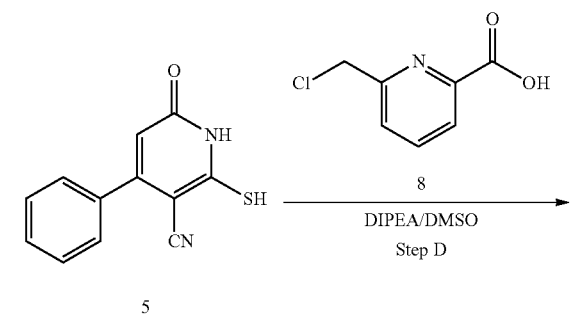

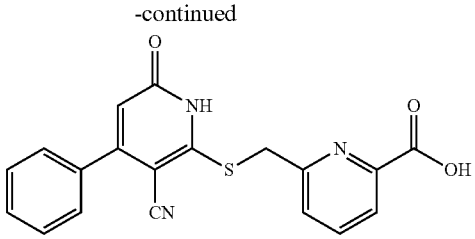

Step A: methyl 6-(chloromethyl)picolinate

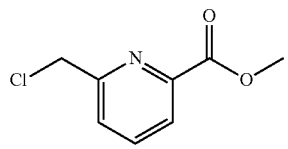

To a solution of methyl 6-(hydroxymethyl)picolinate (1.0 g, 5.98 mmol) in DCM (10 mL) was added thionyl chloride (2 ml) at 0° C. The reaction mixture was stirred at 0° C. for 1 h. TLC (EtOAc/PE=4:1, silica gel plate) showed complete consumption of the starting material after this time. The mixture was concentrated in vacuo. The residue was dissolved with EtOAc (100 mL), washed with sat. Na₂CO₃ aq. solution and brine, dried and concentrated in vacuo to give the desired compound (1.01 g) as a pale yellow solid. LC-MS (ESI⁺): m/z 186.0 (M+H)⁺.

Step B: 6-(chloromethyl)picolinic acid

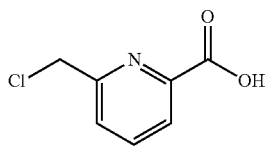 [SMILES: O=C(O)c1cccc(CCl)n1]

To a solution of methyl 6-(chloromethyl)picolinate (500 mg, 2.72 mmol) in MeOH (10 mL) and H₂O (2 mL) was added LiOH (171.2 mg, 4.08 mmol) at room temperature. The reaction mixture was stirred at room temperature for 2 h. TLC (10% MeOH/90% DCM, silica gel plate) showed complete consumption of the starting material after this time. The mixture was adjusted to pH=5, extracted with EtOAc (2×50 mL), washed with brine, dried and concentrated in vacuo to give the desired compound (441 mg) as a white solid. LC-MS (ESI⁺): m/z 172.0 (M+H)⁺.

Step D: 6-(((3-cyano-6-oxo-4-phenyl-1,6-dihydro-pyridin-2-yl)thio)methyl)picolinic acid

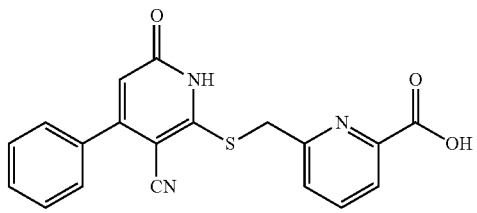 [SMILES: N#Cc1c(-c2ccccc2)cc(=O)[nH]c1SCc1cccc(C(=O)O)n1]

To a solution of 2-mercapto-6-oxo-4-phenyl-1,6-dihydro-pyridine-3-carbonitrile (see Example 12, 100 mg, 0.439 mmol) and 6-(chloromethyl)picolinic acid (97.5 mg, 0.571 mmol) in DMSO (5 mL) was added DIPEA (84.95 mg, 0.659 mmol) at room temperature. The reaction mixture was stirred at room temperature for 1 h. TLC (10% MeOH/90% DCM, silica gel plate) showed complete consumption of the starting material after this time. The mixture was adjusted to pH=5.0, and extracted with EtOAc (2×50 mL). The combined organic layers were washed with brine, dried and concentrated in vacuo. The mixture was purified via reverse phase column chromatography (MeOH/H$_2$O=5%-80%) to give the desired compound (14.8 mg) as a yellow solid.

$^1$H NMR (400 MHz, DMSO-d$_6$) δ: 7.95-7.87 (m, 4H), 7.75 (d, J=3.1 Hz, 1H), 7.45 (s, 3H), 7.02 (s, 1H), 4.75 (s, 2H). LC-MS (ESI$^+$): m/z 363.9 (M+H)$^+$.

Example 34—Synthesis of 5-(((3-cyano-6-oxo-4-phenyl-1,6-dihydropyridin-2-yl)thio)methyl)nicotinic acid

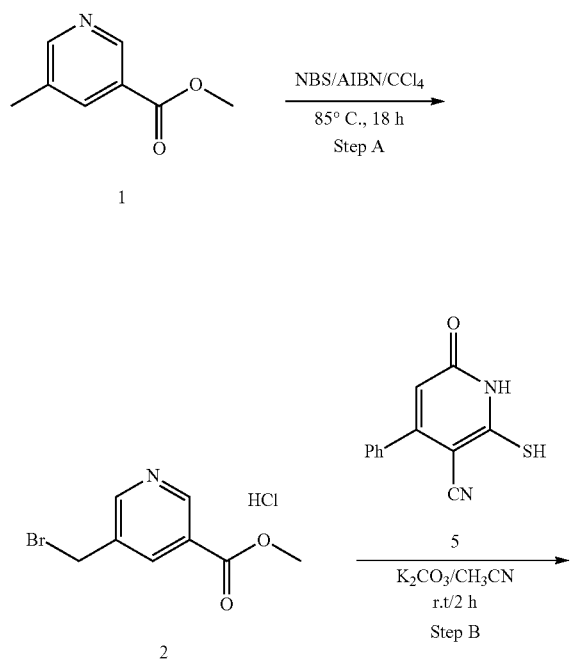

Step A: methyl 5-(bromomethyl)nicotinate hydrochloride

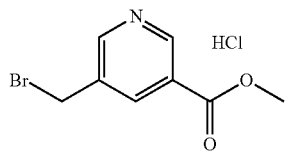

A mixture of methyl 5-methylnicotinate (770 mg, 5.1 mmol), NBS (1.36 g, 7.65 mmol) and AIBN (125 mg, 0.765 mmol) in CCl$_4$ (5 ml) was stirred at 85° C. for 18 h under argon. The reaction mixture was cooled to room temperature. The solvent was removed under reduced pressure. The residue was purified by silica gel column chromatography, eluting with PE/EA=5:1, to get the desired compound, which was treated with HCl (1 N in ether) to give its HCl salt (280 mg) as a white solid. LC-MS (ESI$^+$): m/z 228.9, 230.9 (M+H)$^+$ Step B: methyl 5-(((3-cyano-6-oxo-4-phenyl-1,6-dihydropyridin-2-yl)thio)methyl)nicotinate

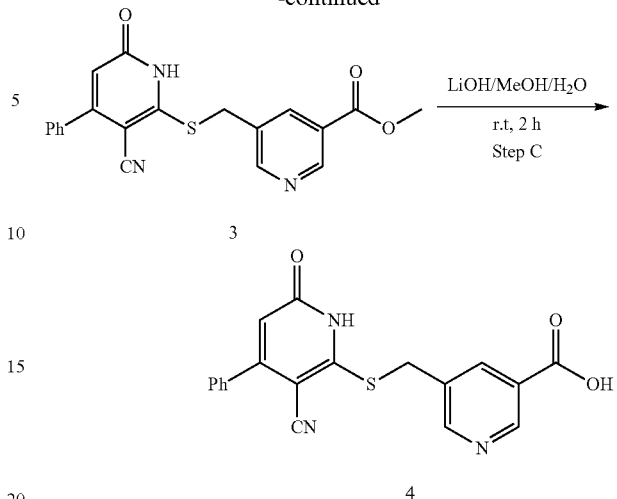

A mixture of methyl 5-(bromomethyl)nicotinate hydrochloride (230 mg, 0.86 mmol), 2-mercapto-6-oxo-4-phenyl-1,6-dihydropyridine-3-carbonitrile (see Example 12, 200 mg, 0.74 mmol), and K$_2$CO$_3$ (237 mg, 1.72 mmol) in acetonitrile (10 ml) was stirred at room temperature for 2 h. The solvent was removed under reduced pressure. The residue was poured into water (20 ml) acidified to pH=3-5 by addition of 1 N HCl, and extracted with EtOAc (3×20 ml). The combined organic layers were washed with brine, dried over Na$_2$SO$_4$, filtered, and concentrated under reduced pressure. The residue was purified by silica gel column chromatography, eluting with MeOH/DCM=5%, to get the desired compound (180 mg) as a white solid. LC-MS (ESI$^+$): m/z 377.9 (M+H)$^+$.

Step C: 5-(((3-cyano-6-oxo-4-phenyl-1,6-dihydropyridin-2-yl)thio)methyl)nicotinic acid

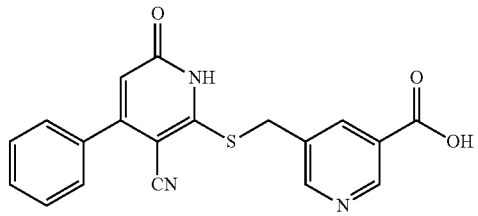 [SMILES: N#Cc1c(-c2ccccc2)cc(=O)[nH]c1SCc1cncc(C(=O)O)c1]

A mixture of methyl 5-(((3-cyano-6-oxo-4-phenyl-1,6-dihydropyridin-2-yl)thio)methyl)nicotinate (60 mg, 0.16 mmol), Lithium hydroxide hydrate (13.4 mg, 0.32 mmol) in MeOH (5 mL) and H$_2$O (1 mL) was stirred at 45° C. for 18 h. The solvent was removed under reduced pressure. The residue was poured into water (5 ml), acidified to pH=5 by addition of 1 N HCl and extracted with EtOAc (3×10 ml). The combined organic layers were washed with brine, dried over Na$_2$SO$_4$, filtered, and concentrated under reduced pressure. The residue was purified by prep HPLC, eluting with MeOH/water=50% (containing 0.1% HCOOH), to get the desired compound (50 mg) as a white solid.

$^1$H NMR (400 MHz, DMSO-d$_6$) δ: 13.13 (brs, 1H), 8.86 (d, J=2.14 Hz, 1H), 8.90 (d, J=1.83 Hz, 1H), 8.37 (t, J=1.98 Hz, 1H), 8.00 (dd, J=6.56, 2.90 Hz, 2H), 7.46-7.61 (m, 3H), 7.15 (s, 1H), 4.72 (s, 2H). LC-MS (ESI$^+$): m/z 364.1 (M+H)$^+$.

Example 35—Synthesis of 3-(((3-cyano-4-(cyclohexylmethyl)-6-oxo-1,6-dihydropyridin-2-yl)thio)methyl)benzoic acid Synthesis scheme

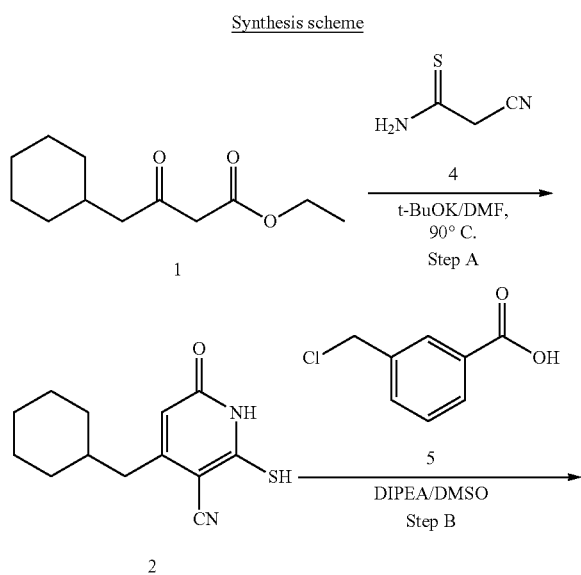

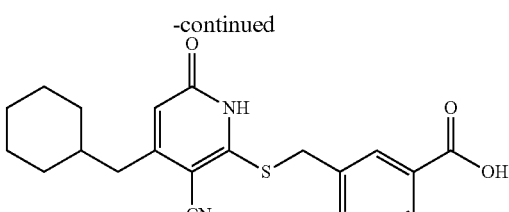

Step A: 4-(cyclohexylmethyl)-2-mercapto-6-oxo-1,6-dihydropyridine-3-carbonitrile

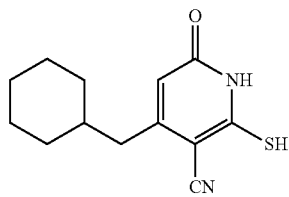 [SMILES: N#Cc1c(CC2CCCCC2)cc(=O)[nH]c1S]

To a solution of ethyl 4-cyclohexyl-3-oxobutanoate (1 g, 4.72 mmol) and 2-cyanoethanethioamide (708 mg, 7.08 mmol) in DMF (15 mL) was added t-BuOK (2.64 g, 23.6 mmol) at r.t. The reaction was heated at 90° C. for 4 h under N$_2$. TLC (50% PE/50% EtOAc, silica gel plate) showed complete consumption of the starting material after this time. The mixture was concentrated in vacuo. The residue was purified via reverse phase column chromatography (MeOH/H$_2$O=5%-80%) to give the desired compound (711.1 mg) as a yellow solid. LC-MS (ESI$^+$): m/z 249.1 (M+H)$^+$.

Step B: 3-(((3-cyano-4-(cyclohexylmethyl)-6-oxo-1,6-dihydropyridin-2-yl)thio)methyl)benzoic acid

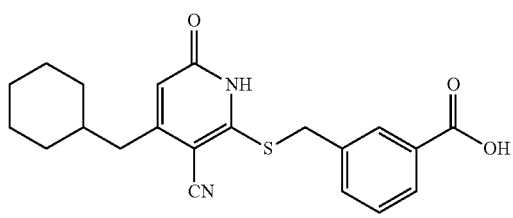 [SMILES: N#Cc1c(CC2CCCCC2)cc(=O)[nH]c1SCc1cccc(C(=O)O)c1]

To a solution of 4-(cyclohexylmethyl)-2-mercapto-6-oxo-1,6-dihydropyridine-3-carbonitrile (150 mg, 0.605 mmol) and 3-(chloromethyl)benzoic acid (155.1 mg, 0.907 mmol) in DMSO (5 mL) was added DIPEA (117 mg, 0.907 mmol) at room temperature. The reaction mixture was stirred at room temperature for 1 h. TLC (10% MeOH/90% DCM, silica gel plate) showed complete consumption of the starting material after this time. The mixture was adjusted to pH=5.0, and extracted with EtOAc (2×50 mL). The combined organic layers were washed with brine, dried and concentrated in vacuo. The mixture was purified via reverse phase column chromatography (MeOH/H$_2$O=5%-80%) to give the desired compound (87.1 mg) as a white solid.

$^1$H NMR (400 MHz, DMSO-d$_6$) δ: 12.93 (s, 1H), 12.38 (s, 1H), 8.02 (s, 1H), 7.80 (d, J=7.7 Hz, 1H), 7.65 (d, J=7.6 Hz, 1H), 7.42 (t, J=7.7 Hz, 1H), 6.51 (s, 1H), 4.54 (s, 2H), 2.54-2.53 (m, 2H), 1.75-1.47 (m, 6H), 1.15-1.05 (m, 3H), 0.95-0.87 (m, 2H). LC-MS (ESI⁺): m/z 383.0 (M+H)⁺.

Example 36—Synthesis of 3-((3-cyano-6-oxo-4-(thiophen-3-yl)-1,6-dihydropyridin-2-ylthio)methyl)benzoic acid Synthesis scheme

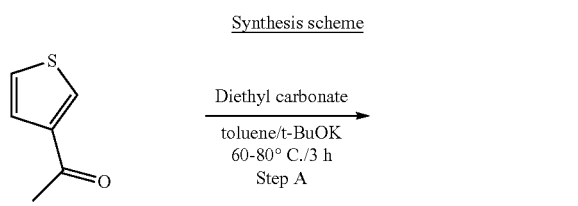

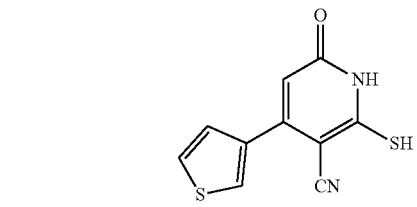

Step A: ethyl 3-oxo-3-(thiophen-3-yl)propanoate

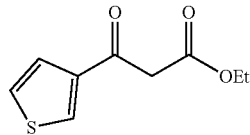 [SMILES: CCOC(=O)CC(=O)c1ccsc1]

Diethyl carbonate (9.36 g, 79.37 mmol) in toluene (50 ml) was heated to 60° C. At this temperature, potassium t-butoxide (7.11 g, 63.52 mmol) was added portionwise. The resultant mixture was heated at 65° C. for half an hour. Then the reaction temperature was raised to 75° C., and 1-(thiophen-3-yl)ethanone (5 g, 39.7 mmol) was added dropwise. The reaction mixture was heated to 80° C. for 90 min, and then allowed to cooled to room temperature. The precipitate solid was filtrated and washed thoroughly with ether. This solid was dissolved in ethyl acetate, washed with brine, dried over Na₂SO₄, filtered, and concentrated under reduced pressure. The residue was purified by silica gel column chromatography, eluting with PE/EtOAc=5:1, to get the desired compound (4.2 g) as a brown oil. LC-MS (ESI⁺): m/z 199.0 (M+H)⁺

Step B: 2-mercapto-6-oxo-4-(thiophen-3-yl)-1,6-dihydropyridine-3-carbonitrile

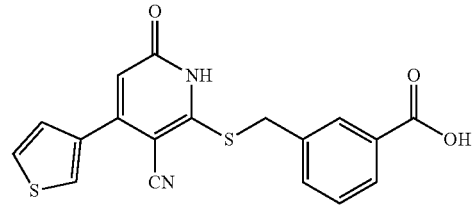 [SMILES: N#Cc1c(-c2ccsc2)cc(=O)[nH]c1SCc1cccc(C(=O)O)c1]

A mixture of ethyl 3-oxo-3-(thiophen-3-yl)propanoate (2.4 g, 12.1 mmol), 2-cyanoethanethioamide (2.42 g, 24.2 mmol) and EtONa (1.67 g, 24.2 mmol) in EtOH (30 mL) was stirred at 90° C. under argon overnight. Then the mixture was cooled to room temperature, poured into water (50 ml), acidified to pH=3-5 by addition of 1 N HCl, and extracted with EtOAc (3×50 ml). The combined organic layers were washed with brine, dried over Na₂SO₄, filtered, and evaporated under vacuo. The residue was purified by silica gel column chromatography, eluting with MeOH/DCM=1:10, to get the title compound (320 mg) as a black solid. LC-MS (ESI⁺): m/z 235.0 (M+H)⁺.

Step C: 3-((3-cyano-6-oxo-4-(thiophen-3-yl)-1,6-dihydropyridin-2-ylthio)methyl)benzoic acid A mixture of 2-mercapto-6-oxo-4-(thiophen-3-yl)-1,6-dihydropyridine-3-carbonitrile (120 mg, 0.513 mmol), 3-(bromomethyl)benzoic acid (134 mg, 0.564 mmol), and K₂CO₃ (142 mg, 1.026 mmol) in acetonitrile (5 mL) was stirred at room temperature for 2 h. The solvent was removed under reduced pressure. The residue was poured into water (20 ml), acidified to pH=3-5 by addition of 1 N HCl, and extracted with EtOAc (3×20 ml). The combined organic layers were washed with brine, dried over Na₂SO₄, filtered, and concentrated under reduced pressure. The residue was purified by pre-HPLC, eluting with MeOH/water=50% (containing 0.1% HCOOH), to get the desired compound (14 mg) as a white solid.

¹H NMR (400 MHz, DMSO-d₆) δ: 12.72 (brs, 2H), 7.99-8.12 (m, 2H), 7.83 (d, J=8.03 Hz, 1H), 7.67-7.78 (m, 2H), 7.39-7.51 (m, 2H), 6.58 (s, 1H), 4.60 (s, 2H). LC-MS (ESI⁺): m/z 369.0 (M+H)⁺.

Example 37—Synthesis of 3-(((3'-cyano-6'-oxo-1',6'-dihydro-[3,4'-bipyridin]-2'-yl)thio)methyl)benzoic acid

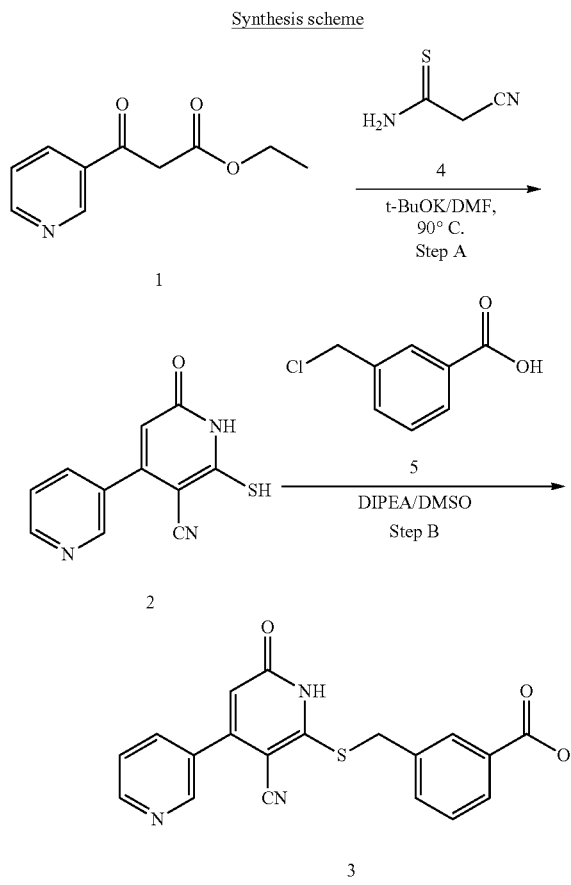

Step A: 2'-mercapto-6'-oxo-1',6'-dihydro-[3,4'-bipyridine]-3'-carbonitrile

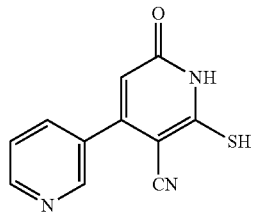 [SMILES: N#Cc1c(-c2cccnc2)cc(=O)[nH]c1S]

To a solution of ethyl 3-oxo-3-(pyridin-3-yl)propanoate (500 g, 2.59 mmol) and 2-cyanoethanethioamide (388 mg, 3.9 mmol) in DMF (50 mL) was added t-BuOK (1.45 g, 12.95 mmol) at room temperature. The reaction mixture was heated at 90° C. for 4 h under N₂. TLC (50% PE/50% EtOAc, silica gel plate) showed complete consumption of the starting material after this time. The mixture was concentrated in vacuo. The residue was purified via reverse phase column chromatography (MeOH/H₂O=5%-80%) to give the desired compound (210.6 mg) as a yellow solid. LC-MS (ESI⁺): m/z 230.0 (M+H)⁺.

Step B: 3-(((3'-cyano-6'-oxo-1',6'-dihydro-[3,4'-bipyridin]-2'-yl)thio)methyl)benzoic acid

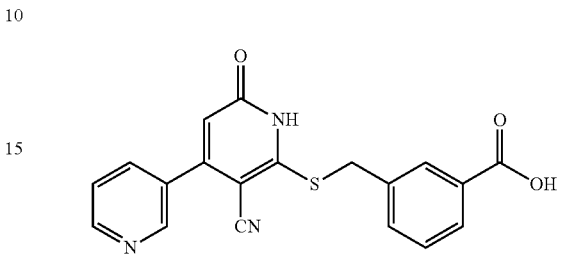

To a solution of 2'-mercapto-6'-oxo-1',6'-dihydro-[3,4'-bipyridine]-3'-carbonitrile (229 mg, 1.0 mmol) and 3-(chloromethyl)benzoic acid (256.5 mg, 1.5 mmol) in DMSO (5 mL) was added DIPEA (194 mg, 1.5 mmol) at room temperature. The reaction mixture was stirred at room temperature for 1 h. TLC (10% MeOH/90% DCM, silica gel plate) showed complete consumption of the starting material after this time. The mixture was adjusted to pH=5, and extracted with EtOAc (2×50 mL). The combined organic layers were washed with brine, dried and concentrated in vacuo. The mixture was purified via reverse phase column chromatography (MeOH/H₂O=5%-80%) to give the desired compound (34.8 mg) as a white solid.

¹H NMR (400 MHz, DMSO-d₆) δ: 12.95 (s, 2H), 9.17 (d, J=1.8 Hz, 1H), 8.74-8.64 (m, 1H), 8.38 (d, J=8.2 Hz, 1H), 8.06 (s, 1H), 7.81 (d, J=7.8 Hz, 1H), 7.70 (d, J=7.7 Hz, 1H), 7.55 (dd, J=8.0, 4.9 Hz, 1H), 7.43 (t, J=7.7 Hz, 1H), 7.22 (s, 1H), 4.70 (s, 2H). LC-MS (ESI⁺): m/z 364.0 (M+H)⁺.

Example 38—Synthesis of 2-(5-chloro-3-cyano-6-oxo-4-(trifluoromethyl)-1,6-dihydropyridin-2-ylthio)acetic acid

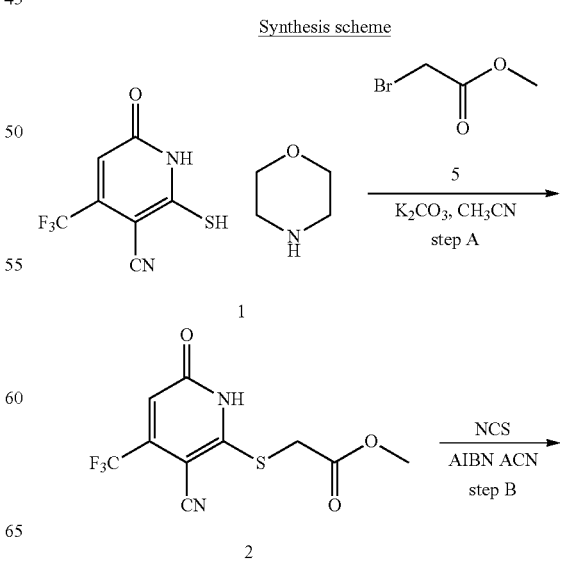

-continued

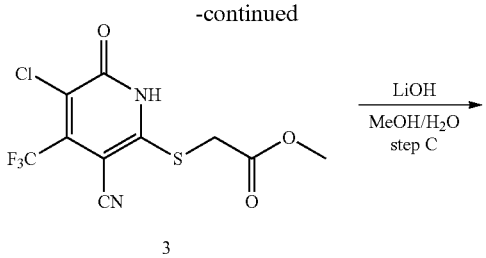

3

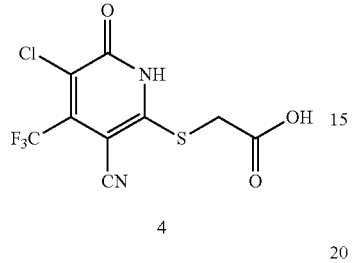

4

Step A: methyl 2-((3-cyano-6-oxo-4-(trifluoromethyl)-1,6-dihydropyridin-2-yl)thio)acetate

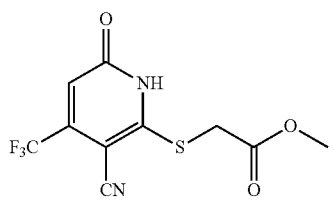 [SMILES: COC(=O)CSc1[nH]c(=O)cc(C(F)(F)F)c1C#N]

To a solution of 2-mercapto-6-oxo-4-(trifluoromethyl)-1,6-dihydropyridine-3-carbonitrile as a 1:1 morpholine salt (800 mg, 2.61 mmol) and methyl 2-bromoacetate (438.6 mg, 2.87 mmol) in DMSO (10 mL) was added DIPEA (370.2 mg, 2.87 mmol) at room temperature. The reaction mixture was stirred at room temperature for 1 h. TLC (10% MeOH/90% DCM, silica gel plate) showed complete consumption of the starting material after this time. The mixture was adjusted to pH=5, extracted with EtOAc (2×50 mL), washed with brine, dried and concentrated in vacuo to give the desired compound (818 mg) as a yellow solid. LC-MS (ESI+): m/z 293.1 (M+H)+.

Step B: methyl 2-(5-chloro-3-cyano-6-oxo-4-(trifluoromethyl)-1,6-dihydropyridin-2-ylthio)acetate

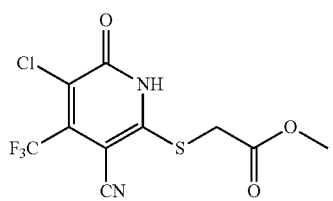

A mixture of methyl 2-(3-cyano-6-oxo-4-(trifluoromethyl)-1,6-dihydropyridin-2-ylthio)acetate (800 mg, 2.74 mmol), AIBN (49 mg, 0.274 mmol), and NCS (441 mg, 3.3 mmol) in acetonitrile (10 ml) was stirred at 80° C. under argon for 18 h. The reaction mixture was diluted with EtOAc (50 ml), washed with water (2×50 mL), and concentrated under reduced pressure. The residue was purified by silica gel column chromatography, eluting with MeOH/DCM=3%-5%, to get the title compound (350 mg) as a white solid. LCMS (ESI+): m/z 327.0 (M+H)+.

Step C: 2-(5-chloro-3-cyano-6-oxo-4-(trifluoromethyl)-1,6-dihydropyridin-2-ylthio)acetic acid

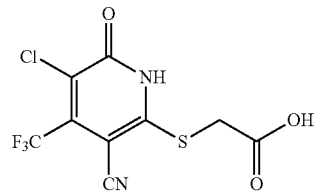

To a solution of methyl 2-(5-chloro-3-cyano-6-oxo-4-(trifluoromethyl)-1,6-dihydropyridin-2-ylthio)acetate (100 mg, 0.307 mmol) in MeOH (5 mL) was added LiOH (26 mg, 0.613 mmol) in water (1 mL). Then the mixture was stirred at room temperature for 3 h. The solvent was removed in vacuo. The residue was resolved in water (20 ml), acidified to pH=3-5 by addition of 1 N HCl, and extracted with EtOAc (3×25 ml). The combined organic layers were concentrated under reduced pressure. The residue was purified by prep-HPLC, eluting with MeOH/H2O=50%-55%, to get the title compound (40 mg) as a white solid.

1H NMR (400 MHz, DMSO-d6) δ: 4.13 (s, 2H). LC-MS (ESI−): m/z 311.0 (M−H)−.

Example 39—Synthesis of 2-((3,5-dicyano-6-oxo-4-(trifluoromethyl)-1,6-dihydropyridin-2-yl)thio)acetic acid Synthesis scheme

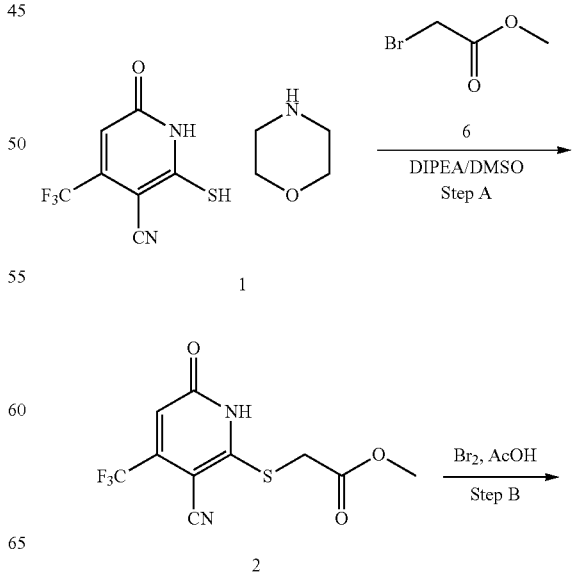

-continued

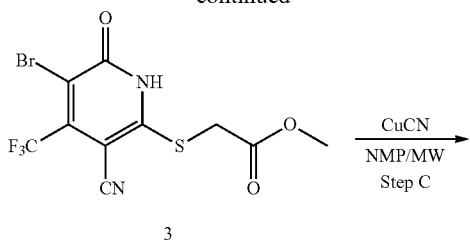

3

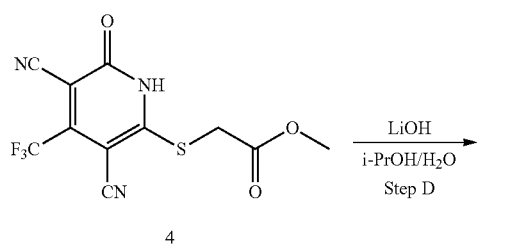

4

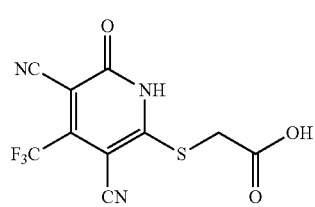

5

Step B: methyl 2-((5-bromo-3-cyano-6-oxo-4-(trifluoromethyl)-1,6-dihydropyridin-2-yl)thio)acetate

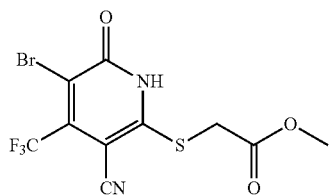

To a solution of methyl 2-((3-cyano-6-oxo-4-(trifluoromethyl)-1,6-dihydropyridin-2-yl)thio)acetate (see Example 38, 1.26 g, 4.32 mmol) in AcOH (30 mL) was added Br$_2$ (332 ul, 6.47 mmol) at r.t. The reaction mixture was stirred at room temperature for 1 h. TLC (EtOAc/PE=1:1, silica gel plate) showed complete consumption of the starting material after this time. The mixture was diluted with water, extracted with EtOAc (2×50 mL), washed with brine, dried and concentrated in vacuo. The residue was purified via column chromatography (DCM/MeOH=10:1) to give the desired compound (901 mg) as a yellow solid. LC-MS (ESI$^+$): m/z 371.0 (M+H)$^+$.

Step C: methyl 2-((3,5-dicyano-6-oxo-4-(trifluoromethyl)-1,6-dihydropyridin-2-yl)thio)acetate

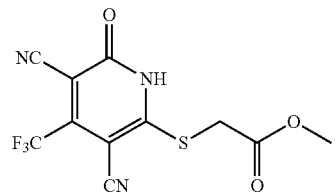 [SMILES: COC(=O)CSc1[nH]c(=O)c(C#N)c(C(F)(F)F)c1C#N]

To a solution of methyl 2-((5-bromo-3-cyano-6-oxo-4-(trifluoromethyl)-1,6-dihydropyridin-2-yl)thio)acetate (1.0 g, 2.69 mmol) in NMP (20 mL) was added CuCN (1.2 g, 13.44 mmol) at r.t. The reaction was stirred at 220° C. through microwave irradiation for 1 h. TLC (EtOAc/PE=3:1, silica gel plate) showed complete consumption of the starting material after this time. The mixture was diluted with EtOAc (100 mL), washed with brine, dried and concentrated in vacuo. The residue was purified via reverse phase column chromatography (MeOH/H$_2$O=5%-80%) to give the desired compound (220 mg) as a yellow solid. LC-MS (ESI$^+$): m/z 318.0 (M+H)$^+$.

Step D: 2-((3,5-dicyano-6-oxo-4-(trifluoromethyl)-1,6-dihydropyridin-2-yl)thio)acetic acid

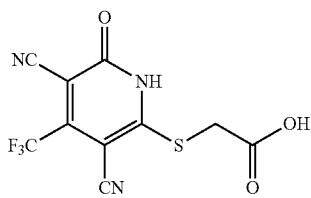 [SMILES: N#Cc1c(SCC(=O)O)[nH]c(=O)c(C#N)c1C(F)(F)F]

To a solution of methyl 2-((3,5-dicyano-6-oxo-4-(trifluoromethyl)-1,6-dihydropyridin-2-yl)thio)acetate (165 mg, 0.521 mmol) in i-PrOH (5 mL) and H$_2$O (3 mL) was added LiOH (33 mg, 0.781 mmol) at room temperature. The reaction mixture was stirred at 80° C. for 1 h. TLC (10% MeOH/90% DCM, silica gel plate) showed complete consumption of the starting material after this time. The mixture was adjusted to pH=5, extracted with EtOAc (2×50 mL), washed with brine, dried and concentrated in vacuo. The residue was purified via reverse phase column chromatography (MeOH/H$_2$O=5%-80%) to give the desired compound (15.1 mg) as a yellow solid.

$^1$H NMR (400 MHz, Methanol-d$_4$) δ: 3.81 (s, 2H). LC-MS (ESI$^-$): m/z 302.1 (M−H)$^-$.

Example 40—Synthesis of 2-((1H-tetrazol-5-yl)methylthio)-5-chloro-6-oxo-4-(trifluoromethyl)-1,6-dihydropyridine-3-carbonitrile Synthesis scheme

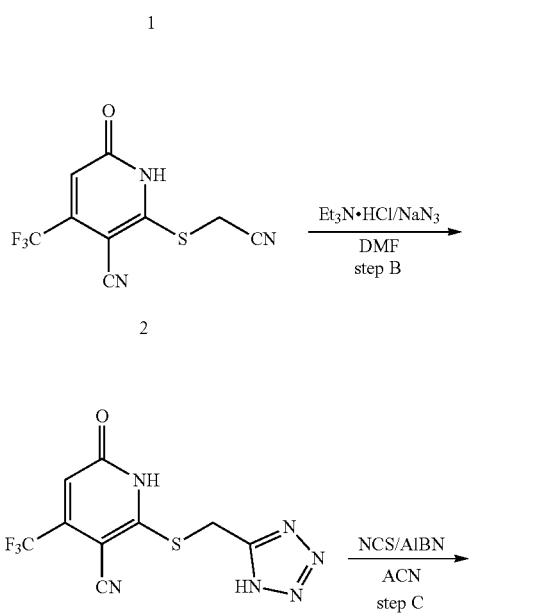

Step A: 2-(cyanomethylthio)-6-oxo-4-(trifluoromethyl)-1,6-dihydropyridine-3-carbonitrile

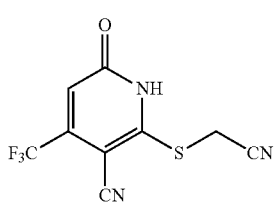 [SMILES: N#CCSc1[nH]c(=O)cc(C(F)(F)F)c1C#N]

To a mixture of 2-mercapto-6-oxo-4-(trifluoromethyl)-1,6-dihydropyridine-3-carbonitrile as a 1:1 morpholine salt (520 mg, 1.7 mmol), 2-bromoacetonitrile (209 mg, 1.87 mmol) in $CH_3CN$ (10 mL) was added $K_2CO_3$ (470 mg, 3.4 mmol), and stirred at room temperature for 2 h. The mixture was concentrated in vacuo. The residue was purified via column chromatography (MeOH/DCM=5%) to give of title compound (280 mg) as a yellow solid. LCMS (ESI$^+$): m/z 260.0 (M+H)$^+$.

Step B: 2-((1H-tetrazol-5-yl)methylthio)-6-oxo-4-(trifluoromethyl)-1,6-dihydropyridine-3-carbonitrile A mixture of 2-(cyanomethylthio)-6-oxo-4-(trifluoromethyl)-1,6-dihydropyridine-3-carbonitrile (280 mg, 1.08 mmol), triethylamine hydrochloride (192 mg, 1.405 mmol), $NaN_3$ (91.3 mg, 1.405 mmol) in DMF (10 mL) was stirred at 110° C. overnight. The reaction mixture was cooled to room temperature, and water (20 mL) was added. The resultant mixture was extracted with EtOAc (3×50 mL). The combined organic layers were concentrated under reduced pressure. The residue was purified by silica gel column chromatography, eluting with MeOH/DCM=10%, to get the title compound (160 mg) as a white solid. LCMS (ESI$^+$): m/z 303.1 (M+H)$^+$.

Step C: 2-((1H-tetrazol-5-yl)methylthio)-5-chloro-6-oxo-4-(trifluoromethyl)-1,6-dihydropyridine-3-carbonitrile A mixture of 2-((1H-tetrazol-5-yl)methylthio)-6-oxo-4-(trifluoromethyl)-1,6-dihydropyridine-3-carbonitrile (160 mg, 0.53 mmol), AIBN (20 mg, 0.106 mmol), NCS (78 mg, 0.582 mmol) in $CH_3CN$ (10 ml) was stirred at 80° C. for 24 h. The solvent was removed in vacuo. The residue was purified by silica gel column chromatography, eluting with MeOH/DCM=3%-8%, to get the title compound (30 mg) as a white solid.

$^1$H NMR (DMSO-$d_6$) δ: 4.82 (s, 2H). LCMS (ESI$^+$): 337.1 (M+H)$^+$.

Example 41—Synthesis of 3-(((5-chloro-3-cyano-6-oxo-4-phenyl-1,6-dihydropyridin-2-yl)thio)methyl)benzoic acid Synthesis scheme

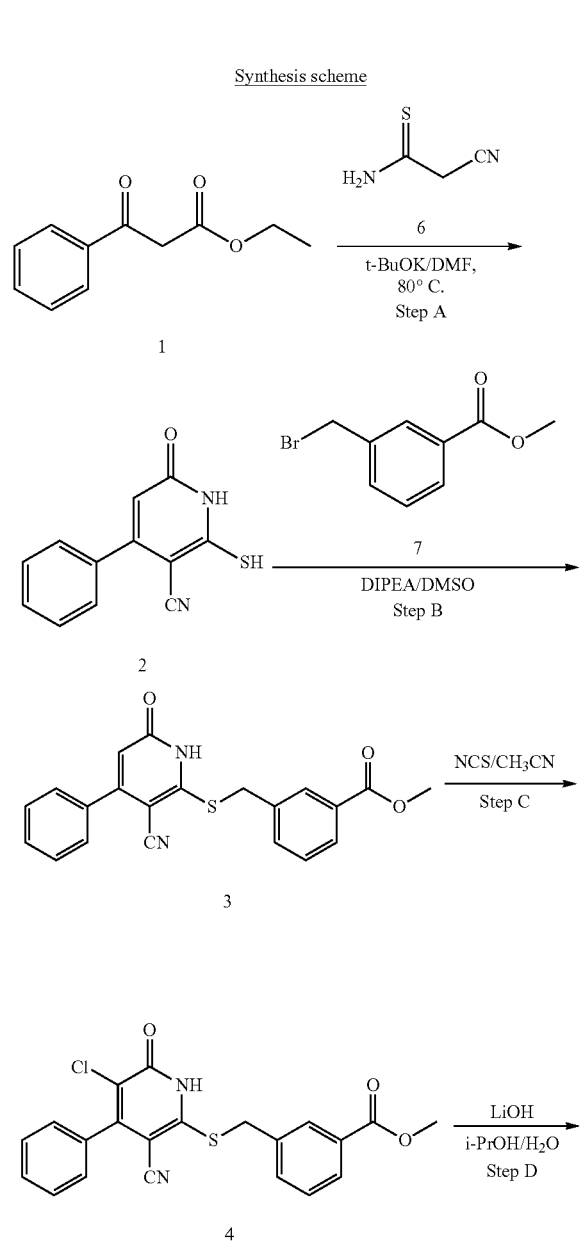

Step B: methyl 3-(((3-cyano-6-oxo-4-phenyl-1,6-dihydropyridin-2-yl)thio)methyl)benzoate

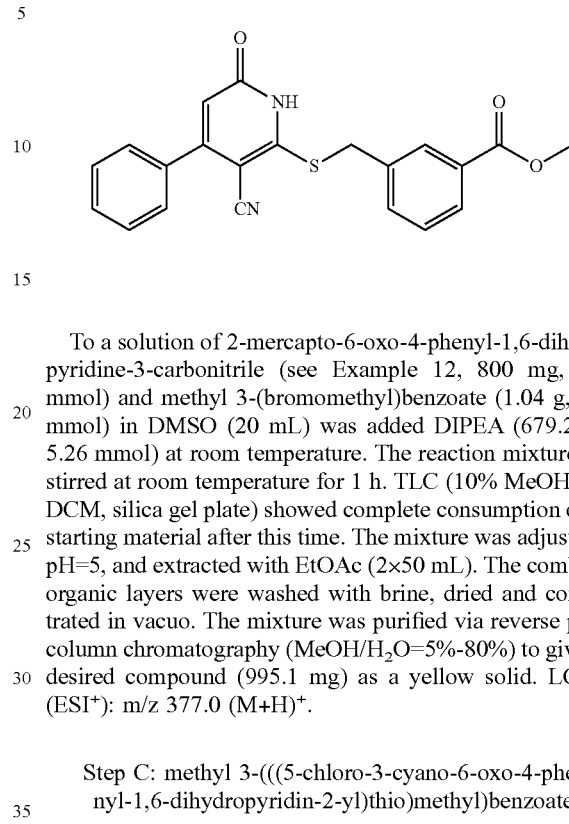

To a solution of 2-mercapto-6-oxo-4-phenyl-1,6-dihydropyridine-3-carbonitrile (see Example 12, 800 mg, 3.51 mmol) and methyl 3-(bromomethyl)benzoate (1.04 g, 4.56 mmol) in DMSO (20 mL) was added DIPEA (679.2 mg, 5.26 mmol) at room temperature. The reaction mixture was stirred at room temperature for 1 h. TLC (10% MeOH/90% DCM, silica gel plate) showed complete consumption of the starting material after this time. The mixture was adjusted to pH=5, and extracted with EtOAc (2×50 mL). The combined organic layers were washed with brine, dried and concentrated in vacuo. The mixture was purified via reverse phase column chromatography (MeOH/H$_2$O=5%-80%) to give the desired compound (995.1 mg) as a yellow solid. LC-MS (ESI$^+$): m/z 377.0 (M+H)$^+$.

Step C: methyl 3-(((5-chloro-3-cyano-6-oxo-4-phenyl-1,6-dihydropyridin-2-yl)thio)methyl)benzoate

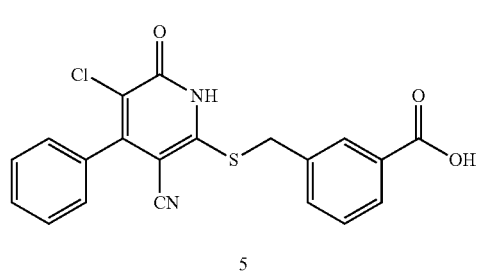

To a solution of methyl 3-(((3-cyano-6-oxo-4-phenyl-1,6-dihydropyridin-2-yl)thio)methyl)benzoate (600 g, 1.596 mmol) in CH$_3$CN (20 mL) was added NCS (319.4 mg, 2.394 mmol) at room temperature. The reaction mixture was stirred at reflux for 12 h. TLC (EtOAc/PE=1:1, silica gel plate) showed complete consumption of the starting material after this time. The mixture was diluted with water, extracted with EtOAc (2×50 mL), washed with brine, dried and concentrated in vacuo. The residue was purified via column chromatography (DCM/MeOH=10:1) to give the desired compound (281 mg) as a yellow solid. LC-MS (ESI$^+$): m/z 410.9 (M+H)$^+$.

Step D: 3-(((5-chloro-3-cyano-6-oxo-4-phenyl-1,6-dihydropyridin-2-yl)thio)methyl)benzoic acid

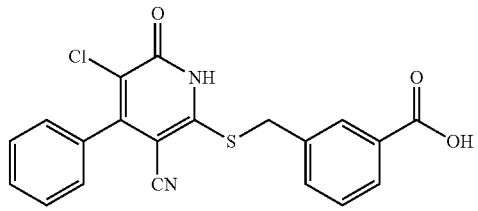

To a solution of methyl 3-(((5-chloro-3-cyano-6-oxo-4-phenyl-1,6-dihydropyridin-2-yl)thio)methyl)benzoate (160 mg, 0.390 mmol) in i-PrOH (5 mL) and H₂O (1 mL) was added LiOH (24.6 mg, 0.585 mmol) at room temperature. The reaction mixture was stirred at 60° C. for 2 h. TLC (10% MeOH/90% DCM, silica gel plate) showed complete consumption of the starting material after this time. The mixture was adjusted to pH=5, extracted with EtOAc (2×50 mL), washed with brine, dried and concentrated in vacuo. The residue was purified via reverse phase column chromatography (MeOH/H₂O=5%-80%) to give the desired compound (107.6 mg) as a yellow solid.

$^1$H NMR (400 MHz, DMSO-d$_6$) δ: 7.97 (s, 1H), 7.84 (d, J=7.7 Hz, 1H), 7.62 (d, J=6.3 Hz, 3H), 7.57-7.50 (m, 3H), 7.46 (t, J=7.7 Hz, 1H), 4.55 (s, 2H). LC-MS (ESI$^+$): m/z 396.9 (M+H)$^+$.

Example 42—Synthesis of 2-(3-(1H-tetrazol-5-yl)benzylthio)-6-oxo-4-(trifluoromethyl)-1,6-dihydropyridine-3-carbonitrile Synthesis scheme

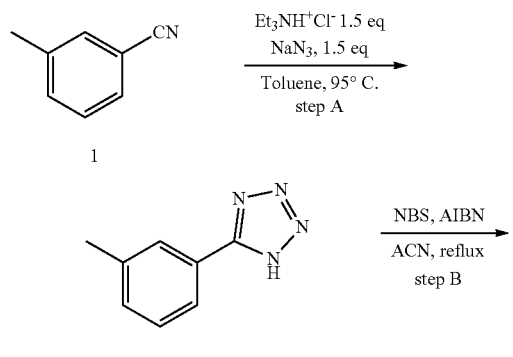

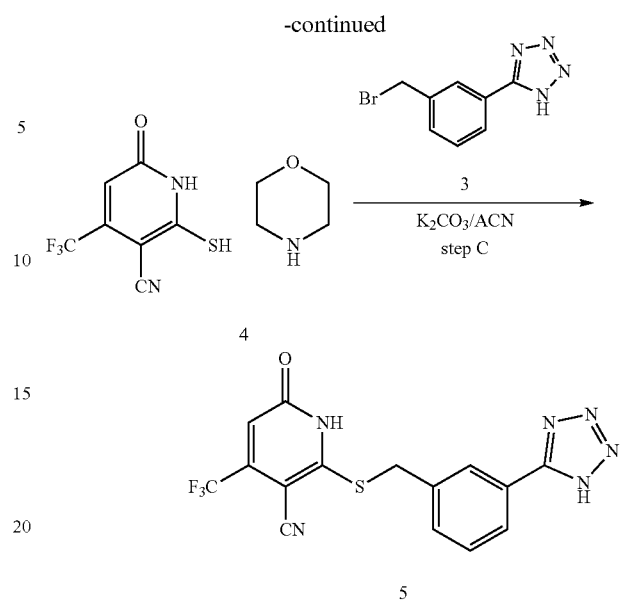

Step A: 5-(m-tolyl)-1H-tetrazole

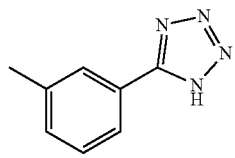

A mixture of 3-methylbenzonitrile (1 g, 8.55 mmol), triethylamine hydrochloride (1.756 g, 12.8 mmol), NaN₃ (832 mg, 12.8 mmol) in toluene (20 mL) was stirred at 95° C. for 24 h under argon. The reaction mixture was cooled to room temperature, and water (40 mL) was added. The mixture was separated. The organic layer was washed with water (20 ml), and the combined aqueous layers were cooled with an ice water bath. Sodium nitrite solution (20 wt % aqueous, 6.57 ml, 19 mmol) was added in one portion, followed by dropwise addition of sulfuric acid (20 wt % aqueous, 6.26 ml, 22.6 mmol) with vigorous stirring. Then the aqueous phase was extracted with EtOAc (2×40 mL). The combined organic layers were concentrated under reduced pressure. The residue was purified by silica gel column chromatography, eluting with MeOH/DCM=5%, to get the title compound (1.1 g) as a white solid.

$^1$H NMR (400 MHz, DMSO-d$_6$) δ: 16.81 (brs, 1H), 7.88 (s, 1H), 7.83 (d, J=7.78 Hz, 1H), 7.50 (t, J=7.67 Hz, 1H), 7.41 (d, J=7.55 Hz, 1H), 2.42 (s, 3H).
LC-MS (ESI+): m/z 161.0 (M+H)$^+$.

Step B: 5-(3-(bromomethyl)phenyl)-1H-tetrazole

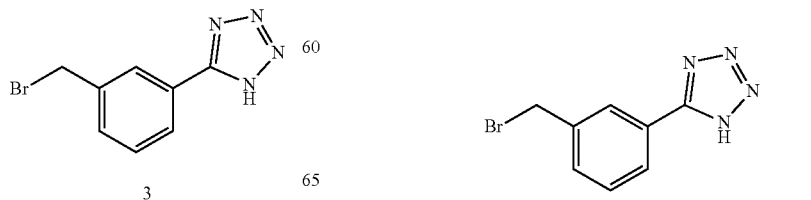

A mixture of 5-(m-tolyl)-1H-tetrazole (724 mg, 4.41 mmol), NBS (1.18 g, 6.62 mmol), AIBN (145 mg, 0.882 mmol) in CH₃CN (30 mL) was stirred at 80° C. for 2 days under argon. The reaction mixture was cooled to room temperature, and then removed the solvent under reduce pressure. The residue was purified by silica gel column chromatography, eluting with PE/EA=30%-50%, to get the title compound (180 mg) as a white solid. LCMS (ESI⁺): m/z 238.9, 240.9 (M+H)⁺.

Step C: 2-(3-(1H-tetrazol-5-yl)benzylthio)-6-oxo-4-(trifluoromethyl)-1,6-dihydropyridine-3-carbonitrile

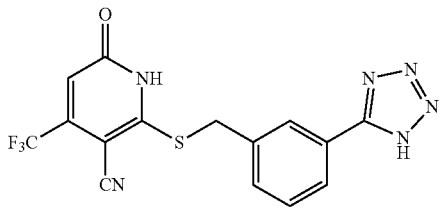 [SMILES: N#Cc1c(C(F)(F)F)cc(=O)[nH]c1SCc1cccc(-c2nnn[nH]2)c1]

A mixture of 2-mercapto-6-oxo-4-(trifluoromethyl)-1,6-dihydropyridine-3-carbonitrile as a 1:1 morpholine salt (129 mg, 0.42 mmol), 5-(3-(bromomethyl)phenyl)-1H-tetrazole (100 mg, 0.42 mmol), K₂CO₃ (116 mg, 0.84 mmol) in CH₃CN (10 ml) was stirred at room temperature for 2 h. The mixture was poured into water (20 mL), acidified by addition of 1 N HCl to pH=3-5, and extracted with EtOAc (3×20 mL). The combined organic layers were washed with brine, dried over Na₂SO₄, filtered, and concentrated under reduced pressure. The residue was purified by prep-HPLC, eluting with MeOH/water=50%-80% (containing 0.1% HCOOH) to get the desired compound (15 mg) as a white solid.
¹H NMR (400 MHz, Methanol-d₄) δ: 8.13 (s, 1H), 7.89 (d, J=7.93 Hz, 1H), 7.66 (d, J=7.63 Hz, 1H), 7.52 (t, J=7.63 Hz, 1H), 6.74 (s, 1H), 4.60 (s, 2H). LC-MS (ESI⁺): 379.1 (M+H)⁺.

Example 43—Synthesis of 2-(((1H-tetrazol-5-yl)methyl)thio)-6-oxo-4-(trifluoromethyl)-1,6-dihydropyridine-3-carbonitrile Synthesis scheme

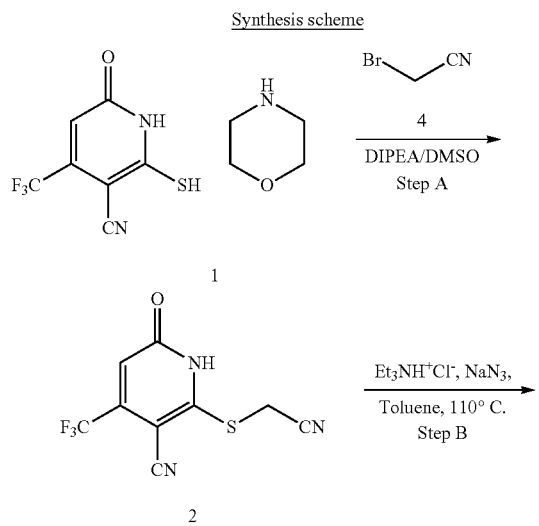

Step A: 2-((cyanomethyl)thio)-6-oxo-4-(trifluoromethyl)-1,6-dihydropyridine-3-carbonitrile

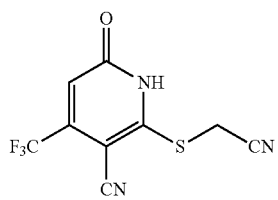 [SMILES: N#CCSc1[nH]c(=O)cc(C(F)(F)F)c1C#N]

To a solution of 2-mercapto-6-oxo-4-(trifluoromethyl)-1,6-dihydropyridine-3-carbonitrile as a 1:1 morpholine salt (307 mg, 1.0 mmol) and 2-bromoacetonitrile (180 mg, 1.5 mmol) in DMSO (8 mL) was added DIPEA (194 mg, 1.5 mmol) at room temperature. The reaction mixture was stirred at room temperature for 1 h. TLC (10% MeOH/90% DCM, silica gel plate) showed complete consumption of the starting material after this time. The mixture was purified via column chromatography (MeOH/DCM=1/10) to give the desired compound (331 mg) as a yellow solid. LC-MS (ESI⁺): m/z 260.0 (M+H)⁺.

Step B: 2-(((1H-tetrazol-5-yl)methyl)thio)-6-oxo-4-(trifluoromethyl)-1,6-dihydropyridine-3-carbonitrile

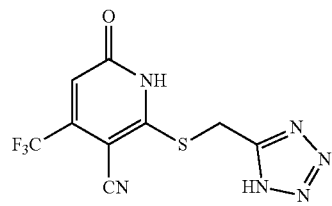 [SMILES: N#Cc1c(C(F)(F)F)cc(=O)[nH]c1SCc1nnn[nH]1]

To a solution of 2-((cyanomethyl)thio)-6-oxo-4-(trifluoromethyl)-1,6-dihydropyridine-3-carbonitrile (300 mg, 1.16 mmol) in toluene (10 mL) was added NaN₃ (113.1 mg, 1.74 mmol) and triethylamine hydrochloride (239.6 mg, 1.74 mmol) at room temperature. The reaction mixture was heated at reflux for 12 h. LCMS showed complete consumption of the starting material after this time. The mixture was extracted with EA (2×50 mL), washed with brine, dried and concentrated in vacuo to give a brown oil, which was purified via reverse phase column chromatography (MeOH/H₂O=5%-80%) to give the desired compound (128 mg) as a white solid.
¹H NMR (400 MHz, DMSO-d₆) δ: 6.94 (s, 1H), 4.86 (s, 2H). LC-MS (ESI⁺): m/z 303.1 (M+H)⁺.

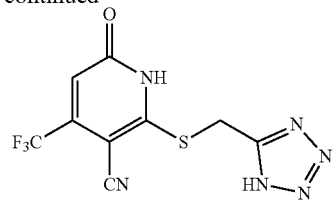

Example 44—Synthesis of 3-((3-cyano-6-oxo-4-(trifluoromethyl)-1,6-dihydropyridin-2-ylthio)methyl)-4-methylbenzoic acid Synthesis scheme

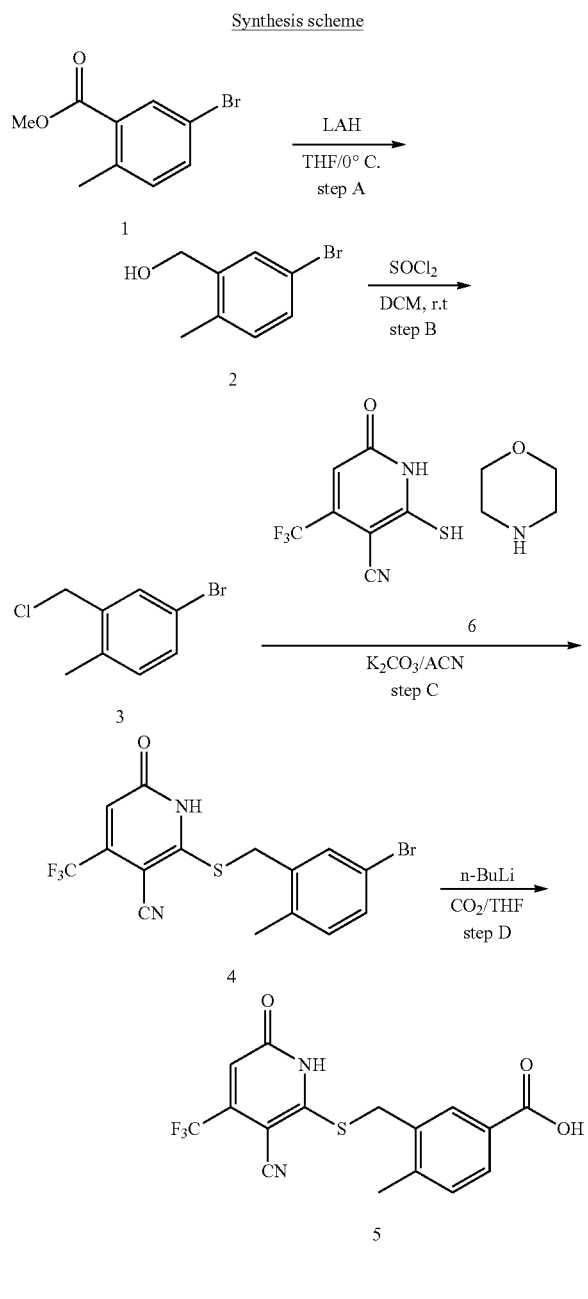

Step A: (5-bromo-2-methylphenyl) methanol

To a solution of methyl 5-bromo-2-methylbenzoate (1.08 g, 4.71 mmol) in dry THF (20 mL) was added carefully LAH (215 mg, 5.66 mmol) in portions at 0° C. After addition, the mixture was stirred at 0° C. for 1 h. Then water (0.75 ml) was added to the reaction mixture, followed by 10 percent NaOH (0.75 mL) and water (2.4 mL). The resultant mixture was filtered and concentrated to afford the title compound (1.6 g) as a colorless oil, which was used in the next reaction without further purification.

Step B: 4-bromo-2-(chloromethyl)-1-methylbenzene

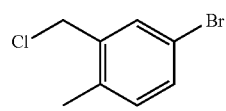

To a mixture of (5-bromo-2-methylphenyl) methanol (1.6 g, 8.0 mmol) in DCM (10 mL) was added dropwise SOCl$_2$ (1.13 g, 9.6 mmol) at room temperature. After addition, the mixture was stirred at room temperature for 18 h and concentrated. The residue was dissolved in DCM (50 mL), washed with saturated NaHCO$_3$ (2×50 mL) and brine (50 mL), dried over Na$_2$SO$_4$, filtered, and concentrated. The residue (1.5 g) was used in the next step without further purification.

Step C: 2-(5-bromo-2-methylbenzylthio)-6-oxo-4-(trifluoromethyl)-1,6-dihydropyridine-3-carbonitrile

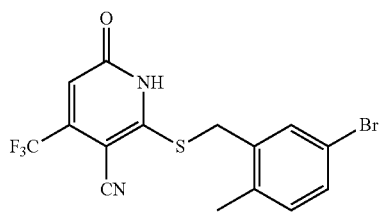 [SMILES: Cc1ccc(Br)cc1CSc1[nH]c(=O)cc(C(F)(F)F)c1C#N]

A mixture of 2-mercapto-6-oxo-4-(trifluoromethyl)-1,6-dihydropyridine-3-carbonitrile as a 1:1 morpholine salt (306 mg, 1 mmol), 4-bromo-2-(chloromethyl)-1-methylbenzene (241.5 mg, 1.1 mmol), K$_2$CO$_3$ (276 mg, 2 mmol) in CH$_3$CN (10 mL) was stirred at room temperature for 2 h. The mixture was poured into water (20 mL), acidified by addition of 1 N HCl to pH=3-5, and extracted with EtOAc (3×20 mL). The combined organic layers were washed with brine, dried over Na$_2$SO$_4$, filtered, and concentrated under reduced pressure. The residue was purified by prep-HPLC, eluting with MeOH/water=40%-60% (containing 0.1% HCOOH), to get the desired compound (300 mg) as a white solid. LC-MS (ESI$^+$): m/z 402.9, 404.9 (M+H)$^+$.

Step D: 3-((3-cyano-6-oxo-4-(trifluoromethyl)-1,6-dihydropyridin-2-ylthio)methyl)-4-methylbenzoic acid

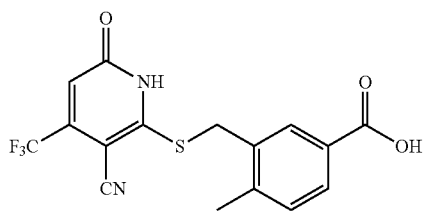 [SMILES: Cc1ccc(C(=O)O)cc1CSc1[nH]c(=O)cc(C(F)(F)F)c1C#N]

To a solution of 2-(5-bromo-2-methylbenzylthio)-6-oxo-4-(trifluoromethyl)-1,6-dihydropyridine-3-carbonitrile (680 mg, 1.683 mmol) in dry THF (10 mL) was added 2.5 M n-BuLi (2 ml, 5.05 mmol) at −78° C. over 30 min. Then $CO_2$ (g) was bubbled into the mixture for 30 min. The reaction was quenched with 10 percent HCl and extracted with EtOAc (3×50 mL). The combined organic layers were washed with brine, dried over $Na_2SO_4$, filtered and concentrated. The residue was purified by silica gel column chromatography, eluting with MeOH/DCM=5%-10%, to get the title compound (11 mg) as a white solid.

$^1$H NMR (400 MHz, Methanol-$d_4$) δ: 8.07 (brs, 1H), 7.86 (d, J=7.79 Hz, 1H), 7.34 (d, J=7.79 Hz, 1H), 6.76 (brs, 1H), 4.65 (brs, 2H), 2.51 (s, 3H). LC-MS (ESI$^-$): m/z 367.0 (M−H)$^-$.

Example 45—Synthesis of 2-(2-chloro-5-(1H-tetrazol-5-yl)benzylthio)-6-oxo-4-(trifluoromethyl)-1,6-dihydropyridine-3-carbonitrile

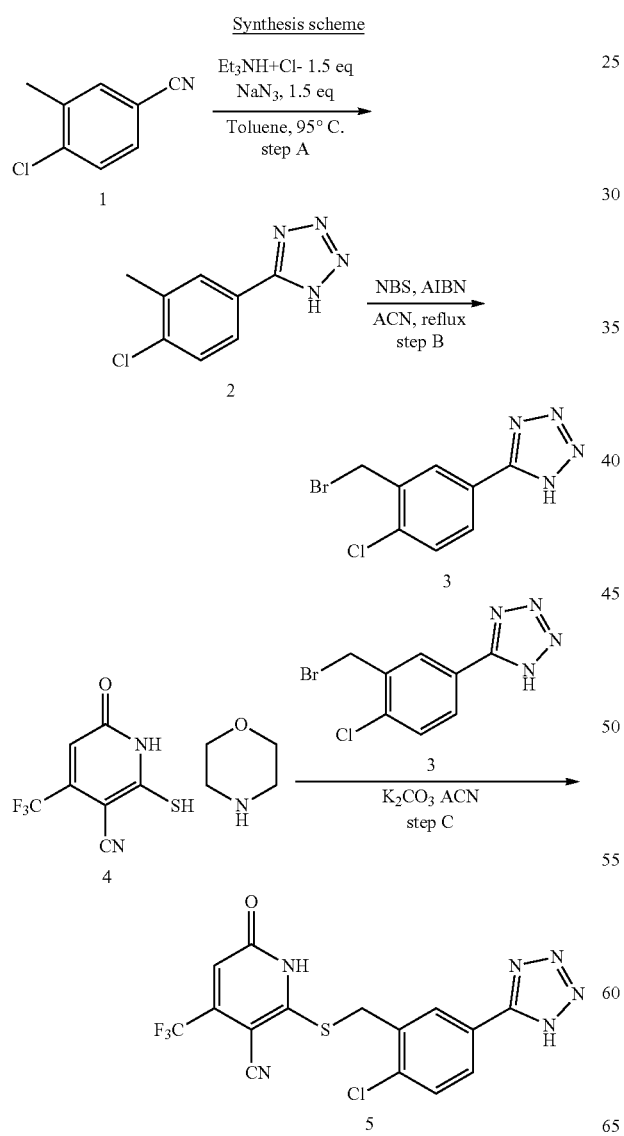

Step A: 5-(4-chloro-3-methylphenyl)-1H-tetrazole

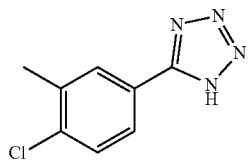

A mixture of 4-chloro-3-methylbenzonitrile (1 g, 6.56 mmol), triethylamine hydrochloride (1.35 g, 9.84 mmol), $NaN_3$ (640 mg, 9.84 mmol) in toluene (20 mL) was stirred at 95° C. for 24 h under argon. The mixture was then cooled to room temperature, and water (40 mL) was added. The resultant mixture was separated, and the organic layer was washed with water (20 ml). The combined aqueous layers were cooled with an ice water bath. Sodium nitrite solution (20 wt % aqueous, 6.57 mL, 19 mmol) was added in one portion, followed by dropwise addition of sulfuric acid (20 wt % aqueous, 6.26 mL, 22.6 mmol) with vigorous stirring. Then the aqueous phase was extracted with EtOAc (2×40 mL). The combined organic layers were concentrated under reduced pressure. The residue was purified by silica gel column chromatography, eluting with MeOH/DCM=5%, to get the title compound (1.5 g) as a white solid. LC-MS (ESI$^+$): m/z 195.0 (M+H)$^+$.

Step B: 5-(3-(bromomethyl)-4-chlorophenyl)-1H-tetrazole

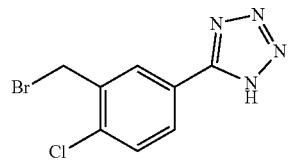 [SMILES: Clc1ccc(-c2nnn[nH]2)cc1CBr]

A mixture of 5-(4-chloro-3-methylphenyl)-1H-tetrazole (500 mg, 2.56 mmol), NBS (546 mg, 3.07 mmol), AIBN (84 mg, 0.512 mmol) in $CH_3CN$ (30 ml) was stirred at 80° C. for 2 days under argon. The mixture was then cooled to room temperature, and removed the solvent under reduce pressure. The residue was purified by silica gel column chromatography, eluting with PE/EA=30%-50%, to get the title compound (180 mg) as a white solid. LC-MS (ESI$^+$): m/z 273.0 (M+H)$^+$.

Step C: 2-(2-chloro-5-(1H-tetrazol-5-yl)benzylthio)-6-oxo-4-(trifluoromethyl)-1,6-dihydropyridine-3-carbonitrile

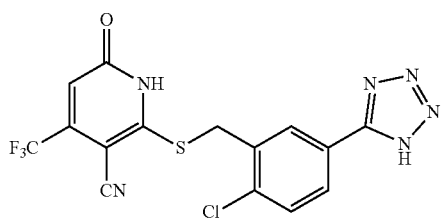 [SMILES: N#Cc1c(C(F)(F)F)cc(=O)[nH]c1SCc1cc(-c2nnn[nH]2)ccc1Cl]

A mixture of 2-mercapto-6-oxo-4-(trifluoromethyl)-1,6-dihydropyridine-3-carbonitrile as a 1:1 morpholine salt (150 mg, 0.49 mmol), 5-(3-(bromomethyl)-4-chlorophenyl)-1H-tetrazole (146 mg, 0.54 mmol), $K_2CO_3$ (135 mg, 0.98 mmol) in $CH_3CN$ (10 mL) was stirred at room temperature for 2 h. The mixture was poured into water (20 mL), acidified by addition of 1 N HCl to pH=3-5, and extracted with EtOAc (3×20 mL). The combined organic layers were washed with brine, dried over $Na_2SO_4$, filtered, and concentrated under reduced pressure. The residue was purified by prep-HPLC, eluting with MeOH/water=50%-80% (containing 0.1% HCOOH) to get the desired compound (20 mg) as a white solid.

$^1$H NMR (400 MHz, Methanol-$d_4$) δ: 8.39 (d, J=1.88 Hz, 1H), 7.95 (dd, J=8.33, 2.15 Hz, 1H), 7.67 (d, J=8.60 Hz, 1H), 6.81 (s, 1H), 4.76 (s, 2H). LC-MS (ESI$^+$): m/z 413.0 (M+H)$^+$.

Example 46—Synthesis of 2-(3-cyano-5-methoxy-6-oxo-4-(trifluoromethyl)-1,6-dihydropyridin-2-ylthio)acetic acid Synthesis scheme

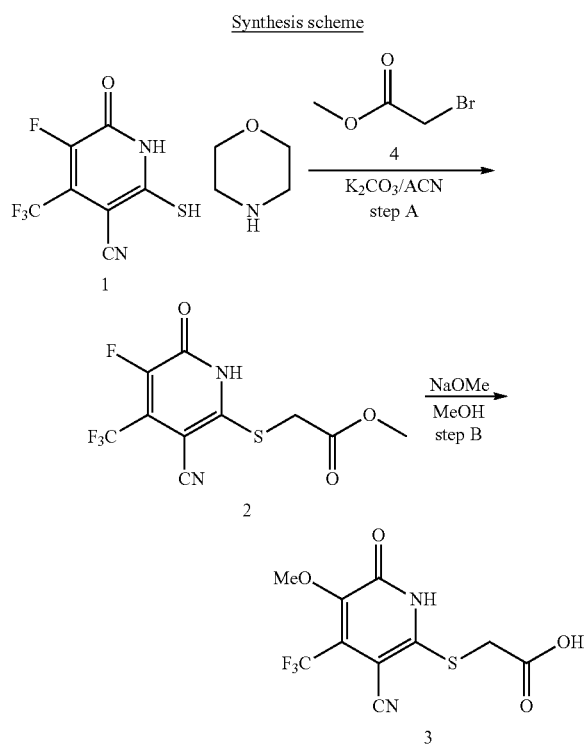

Step A: Methyl 2-(3-cyano-5-fluoro-6-oxo-4-(trifluoromethyl)-1,6-dihydropyridin-2-ylthio)acetate

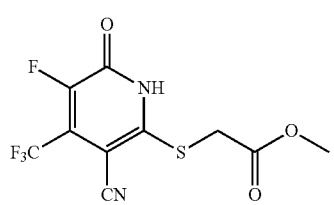 [SMILES: COC(=O)CSc1[nH]c(=O)c(F)c(C(F)(F)F)c1C#N]

A mixture of 5-fluoro-2-mercapto-6-oxo-4-(trifluoromethyl)-1,6-dihydropyridine-3-carbonitrile as a 1:1 morpholine salt (240 mg, 0.74 mmol), methyl 2-bromoacetate (136 mg, 0.886 mmol), $K_2CO_3$ (204 mg, 1.48 mmol) in $CH_3CN$ (10 mL) was stirred at room temperature for 2 h. The mixture was poured into water (20 mL), acidified by addition of 1N HCl to pH=3-5, and extracted with EtOAc (3×20 mL). The combined organic layers were washed with brine, dried over $Na_2SO_4$, filtered, and concentrated under reduced pressure. The residue was purified by silica gel column chromatography, eluting with MeOH/DCM=3%, to get the desired compound (180 mg) as a white solid. LC-MS (ESI$^+$): m/z 311.0 (M+H)$^-$ Step B: 2-(3-cyano-5-methoxy-6-oxo-4-(trifluoromethyl)-1,6-dihydropyridin-2-ylthio)acetic acid

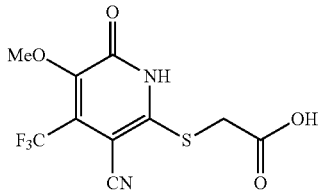 [SMILES: COc1c(C(F)(F)F)c(C#N)c(SCC(=O)O)[nH]c1=O]

To a solution of methyl 2-(3-cyano-5-fluoro-6-oxo-4-(trifluoromethyl)-1,6-dihydropyridin-2-ylthio)acetate (180 mg, 0.58 mmol) in MeOH (5 mL) was added MeONa (2 ml, 33% in MeOH). Then the mixture was stirred at reflux for 2 h. The mixture was concentrated. The residue was dissolved in water, acidified to pH=3-5 by addition of 1 N HCl, and extracted with EtOAc (3×20 mL). The combined organic layers were washed with brine, dried over $Na_2SO_4$, filtered, and concentrated under reduce pressure. The residue was purified by prep-TLC, eluting with MeOH/DCM=10%, to get the title compound (25 mg) as a white solid.

$^1$H NMR (400 MHz, Methanol-$d_4$) δ: 4.03 (brs, 2H), 3.93 (s, 3H). LCMS (ESI$^-$): m/z 307.0 (M–H)$^-$.

Example 47—Synthesis of 2-(((1H-tetrazol-5-yl)methyl)thio)-5-methyl-6-oxo-4-(trifluoromethyl)-1,6-dihydropyridine-3-carbonitrile Synthesis scheme

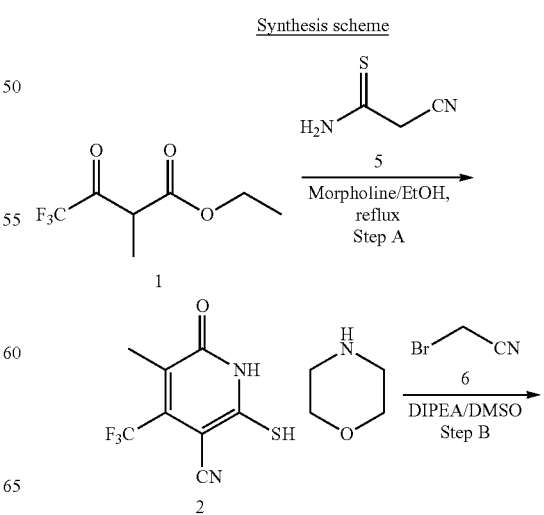

-continued

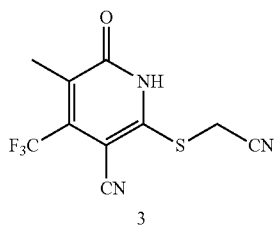

3

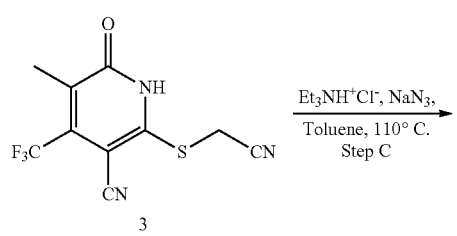

Step A: 2-mercapto-5-methyl-6-oxo-4-(trifluoromethyl)-1,6-dihydropyridine-3-carbonitrile as a 1:1 morpholine salt

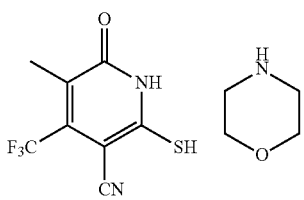

To a solution of ethyl 4,4,4-trifluoro-2-methyl-3-oxobutanoate (2 g, 10.1 mmol) and 2-cyanoethanethioamide (1.01 g, 10.1 mmol) in EtOH (45 mL) was added morpholine (1.14 g, 13.1 mmol) at room temperature. The reaction mixture was stirred at reflux for 3 h. TLC (EtOAc/PE=1:1, silica gel plate) showed complete consumption of the starting material after this time. The mixture was concentrated in vacuo. The residue was purified via reverse phase column chromatography (MeOH/H$_2$O=5%-80%) to give the desired compound as a 1:1 morpholine salt (235.1 mg) as a brown solid. LC-MS (ESI$^-$): m/z 233.1 (M−H)$^-$.

Step B: 2-((cyanomethyl)thio)-5-methyl-6-oxo-4-(trifluoromethyl)-1,6-dihydropyridine-3-carbonitrile

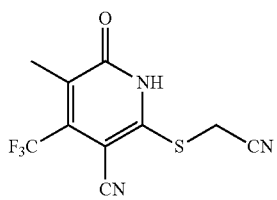 [SMILES: Cc1c(C(F)(F)F)c(C#N)c(SCC#N)[nH]c1=O]

To a solution of 2-mercapto-5-methyl-6-oxo-4-(trifluoromethyl)-1,6-dihydropyridine-3-carbonitrile as a 1:1 morpholine salt (523 mg, 1.63 mmol) and 2-bromoacetonitrile (254 mg, 2.12 mmol) in DMSO (10 mL) was added DIPEA (315 mg, 2.44 mmol) at room temperature. The reaction was stirred at room temperature for 1 h. TLC (10% MeOH/90% DCM, silica gel plate) showed complete consumption of the starting material after this time. The residue was purified via column chromatography (DCM/MeOH, 10:1) to give the desired compound (180 mg) as a yellow solid. LC-MS (ESI$^+$): m/z 274.1 (M+H)$^+$.

Step C: 2-(((1H-tetrazol-5-yl)methyl)thio)-5-methyl-6-oxo-4-(trifluoromethyl)-1,6-dihydropyridine-3-carbonitrile

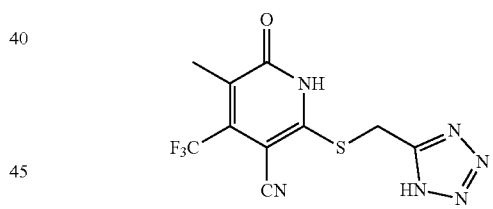

To a solution of 2-((cyanomethyl)thio)-5-methyl-6-oxo-4-(trifluoromethyl)-1,6-dihydropyridine-3-carbonitrile (180 mg, 0.659 mmol) in toluene (10 mL) was added NaN$_3$ (64 mg, 0.981 mmol) and triethylamine hydrochloride (135 mg, 0.989 mmol) at room temperature. The reaction mixture was heated at reflux for 12 h. LC-MS showed complete consumption of the starting material after this time. The mixture was extracted with EtOAc (2×50 mL), washed with brine, dried and concentrated in vacuo to give a brown oil, which was purified via reverse phase column chromatography (MeOH/H$_2$O=5%-80%) to give the desired compound (106.0 mg) as a yellow solid.

$^1$H NMR (400 MHz, DMSO-d$_6$) δ: 4.84 (s, 2H), 2.21 (s, 3H). LC-MS (ESI$^+$): m/z 317.1 (M+H)$^+$.

Example 48—Synthesis of 2-((1H-tetrazol-5-yl)methylthio)-5-fluoro-6-oxo-4-(trifluoromethyl)-1,6-dihydropyridine-3-carbonitrile Synthesis scheme

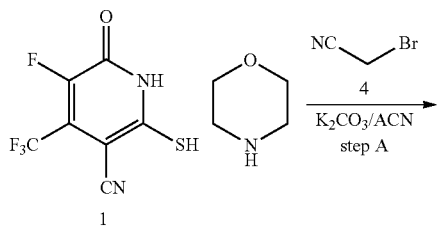

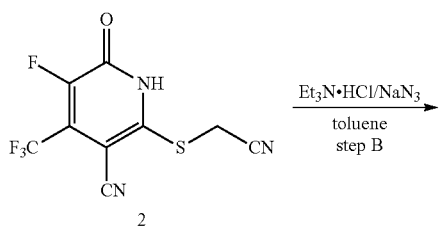

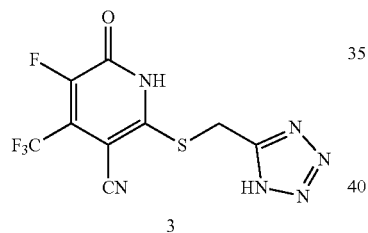

Step A: 2-(cyanomethylthio)-5-fluoro-6-oxo-4-(trifluoromethyl)-1,6-dihydropyridine-3-carbonitrile

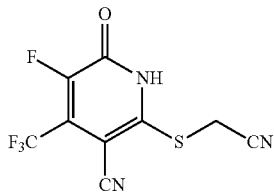 [SMILES: N#CCSc1[nH]c(=O)c(F)c(C(F)(F)F)c1C#N]

To a mixture of 5-fluoro-2-mercapto-6-oxo-4-(trifluoromethyl)-1,6-dihydropyridine-3-carbonitrile as a 1:1 morpholine salt (500 mg, 1.5 mmol), 2-bromoacetonitrile (202 mg, 1.7 mmol) in CH$_3$CN (10 mL) was added K$_2$CO$_3$ (423 mg, 3.1 mmol), and stirred at room temperature for 2 h. The mixture was concentrated in vacuo. The residue (510 mg) was used in the next step without further purification. LC-MS (ESI$^-$): m/z 276.0 (M−H)$^-$.

Step B: 2-((1H-tetrazol-5-yl)methylthio)-5-fluoro-6-oxo-4-(trifluoromethyl)-1,6-dihydropyridine-3-carbonitrile

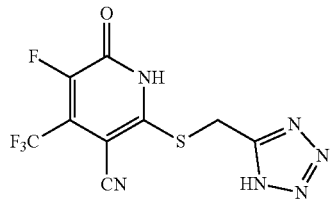 [SMILES: N#Cc1c(SCc2nnn[nH]2)[nH]c(=O)c(F)c1C(F)(F)F]

A mixture of 2-(cyanomethylthio)-5-fluoro-6-oxo-4-(trifluoromethyl)-1,6-dihydropyridine-3-carbonitrile (510 mg, 1.83 mmol), triethylamine hydrochloride (327 mg, 2.385 mmol), NaN$_3$ (155 mg, 2.385 mmol) in toluene (10 ml) was stirred at 90° C. overnight. The reaction mixture was cooled to room temperature, and water (20 ml) was added. The resultant mixture was extracted with EtOAc (3×50 mL). The combined organic layers were concentrated under reduced pressure. The residue was purified by prep-HPLC, eluting with MeOH/Water=40% (containing 0.1% HCOOH), to get the desired compound (90 mg) as a white solid.

$^1$H NMR (400 MHz, DMSO-d$_6$) δ: 4.79 (s, 2H). LC-MS (ESI$^-$): m/z 318.9 (M−H)$^-$.

Example 49—Synthesis of 2-((3-(1H-tetrazol-5-yl)benzyl)thio)-6-oxo-4-(thiophen-2-yl)-1,6-dihydropyridine-3-carbonitrile Synthesis scheme

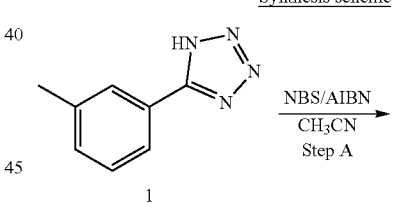

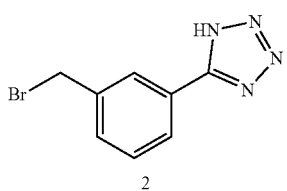

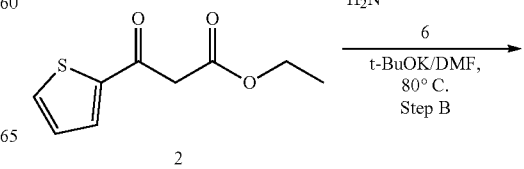

-continued

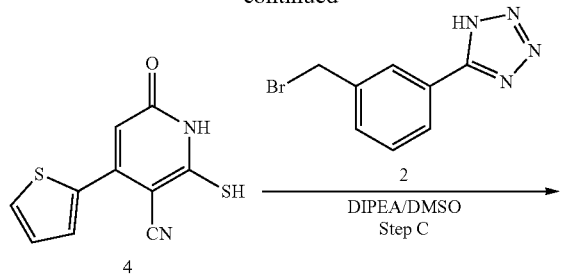

Step A: 5-(3-(bromomethyl)phenyl)-1H-tetrazole

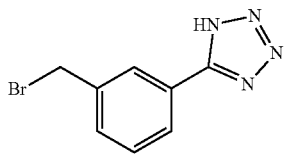 [SMILES: BrCc1cccc(-c2nnn[nH]2)c1]

To a solution of 5-(m-tolyl)-1H-tetrazole (1.86 g, 11.6 mmol) and NBS (2.28 g, 12.8 mmol) in CH$_3$CN (50 mL) was added AIBN (381.3 mg, 2.22 mmol) at room temperature. The reaction mixture was stirred at reflux for 12 h. TLC (EtOAc/PE=1:1, silica gel plate) showed complete consumption of the starting material after this time. The mixture was concentrated in vacuo. The residue was purified via column chromatography (MeOH/DCM=1%-10%) to give the desired compound (981.1 mg) as a yellow solid. LC-MS (ESI$^+$): m/z 239.0 (M+H)$^+$.

Step B: 2-mercapto-6-oxo-4-(thiophen-2-yl)-1,6-dihydropyridine-3-carbonitrile

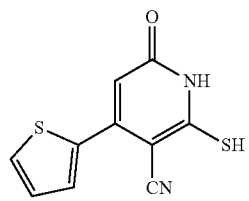 [SMILES: N#Cc1c(-c2cccs2)cc(=O)[nH]c1S]

To a solution of ethyl 3-oxo-3-(thiophen-2-yl)propanoate (1.2 g, 6.05 mmol) and 2-cyanoethanethioamide (666 mg, 6.66 mmol) in DMF (50 mL) was added t-BuOK (3.4 g, 30.3 mmol) at room temperature. The reaction mixture was heated at 80° C. for 4 h under N$_2$. TLC (50% PE/50% EtOAc, silica gel plate) showed complete consumption of the starting material after this time. The mixture was cooled to room temperature, adjusted to pH=5, and extracted with EtOAc (2×50 mL). The combined organic layers were washed with brine, dried, and concentrated in vacuo. The residue was purified via column chromatography (DCM/MeOH=10:1) to give the desired compound (348.1 mg) as a yellow solid. LC-MS (ESI$^+$): m/z 235.0 (M+H)$^+$.

Step C: 2-((3-(1H-tetrazol-5-yl)benzyl)thio)-6-oxo-4-(thiophen-2-yl)-1,6-dihydropyridine-3-carbonitrile

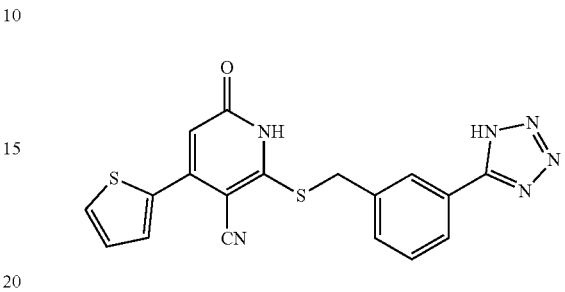

To a solution of 2-mercapto-6-oxo-4-(thiophen-2-yl)-1,6-dihydropyridine-3-carbonitrile (200 mg, 0.855 mmol) and 5-(3-(bromomethyl)phenyl)-1H-tetrazole (203.4 mg, 0.855 mmol) in DMSO (10 mL) was added DIPEA (165.4 mg, 1.283 mmol) at room temperature. The reaction was stirred at r.t. for 1 h. TLC (10% MeOH/90% DCM, silica gel plate) showed complete consumption of the starting material after this time. The mixture was purified via reverse phase column chromatography (MeOH/H$_2$O=5%-80%) to give the desired compound (51.1 mg) as a yellow solid.

$^1$H NMR (400 MHz, DMSO-d$_6$) δ: 8.19 (s, 1H), 7.90 (d, J=7.9 Hz, 1H), 7.81-7.74 (m, 2H), 7.71 (d, J=8.0 Hz, 1H), 7.54 (t, J=7.8 Hz, 1H), 7.21 (dd, J=5.0, 3.8 Hz, 1H), 7.09 (s, 1H), 4.69 (s, 2H). LC-MS (ESI$^+$): m/z 393.0 (M+H)$^+$.

Example 50—Synthesis of 2-((3-(1H-tetrazol-5-yl)benzyl)thio)-6-oxo-4-phenyl-1,6-dihydropyridine-3-carbonitrile Synthesis scheme

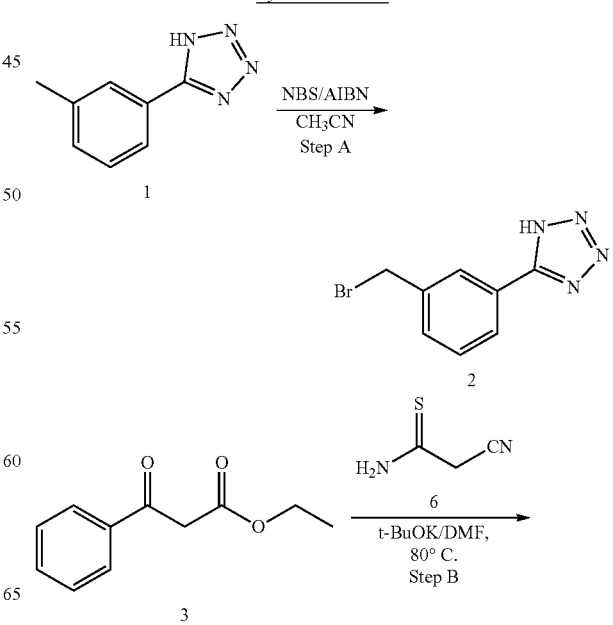

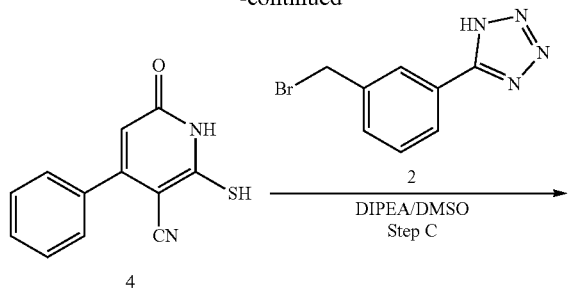

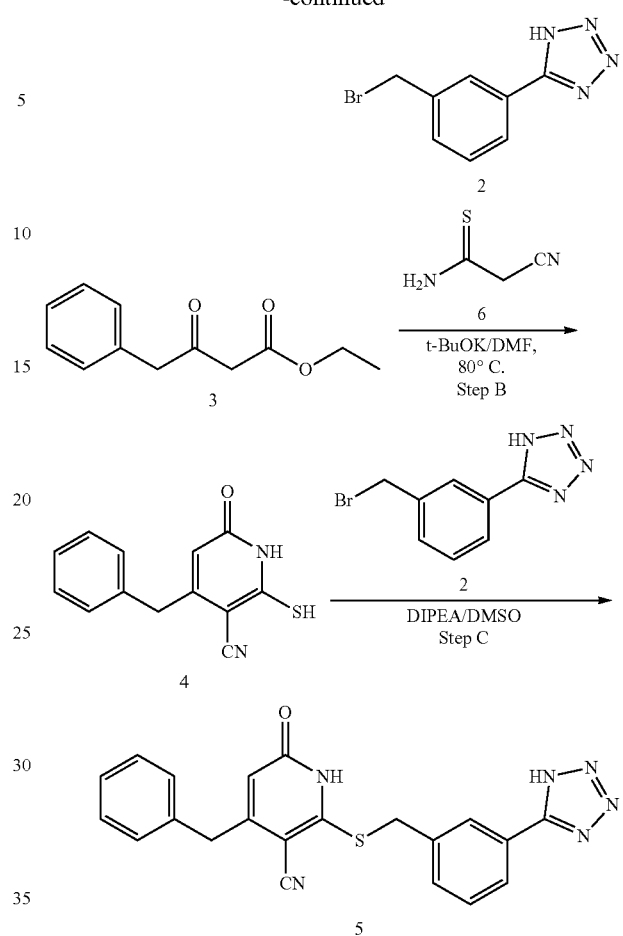

Step C: 2-((3-(1H-tetrazol-5-yl)benzyl)thio)-6-oxo-4-phenyl-1,6-dihydropyridine-3-carbonitrile To a solution of 2-mercapto-6-oxo-4-phenyl-1,6-dihydropyridine-3-carbonitrile (see Example 12, 100 mg, 0.439 mmol) and 5-(3-(bromomethyl)phenyl)-1H-tetrazole (see Example 49, 104.5 mg, 0.439 mmol) in DMSO (5 mL) was added DIPEA (84.9 mg, 0.658 mmol) at room temperature. The reaction mixture was stirred at room temperature for 1 h. TLC (10% MeOH/90% DCM, silica gel plate) showed complete consumption of the starting material after this time. The mixture was purified via reverse phase column chromatography (MeOH/H$_2$O=5%-80%) to give the desired compound (19.1 mg) as a yellow solid.

$^1$H NMR (400 MHz, DMSO-d$_6$) δ: 8.19 (s, 1H), 8.03-7.96 (m, 2H), 7.90 (d, J=7.8 Hz, 1H), 7.67 (d, J=7.6 Hz, 1H), 7.59-7.43 (m, 4H), 7.15 (s, 1H), 4.73 (s, 2H). LC-MS (ESI$^+$): m/z 387.1 (M+H)$^+$.

Example 51—Synthesis of 2-((3-(1H-tetrazol-5-yl)benzyl)thio)-4-benzyl-6-oxo-1,6-dihydropyridine-3-carbonitrile Synthesis scheme

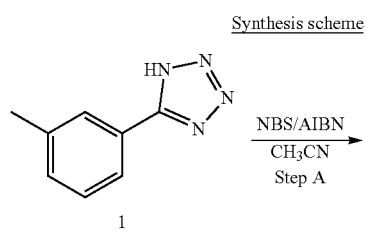

Step B: 4-benzyl-2-mercapto-6-oxo-1,6-dihydropyridine-3-carbonitrile

To a solution of ethyl 3-oxo-4-phenylbutanoate (900 mg, 4.68 mmol) and 2-cyanoethanethioamide (515 mg, 5.15 mmol) in DMF (50 mL) was added t-BuOK (576.9 mg, 5.15 mmol) at r.t. The reaction was heated at 88° C. for 5 h under N$_2$. TLC (50% PE/50% EtOAc, silica gel plate) showed complete consumption of the starting material after this time. The mixture was cooled to room temperature, adjusted to pH=5, and extracted with EtOAc (2×50 mL). The combined organic layer was washed with brine, dried and concentrated in vacuo. The residue was purified via column chromatography (DCM/MeOH=10:1) to give the desired compound (468.1 mg) as a yellow solid. LC-MS (ESI$^+$): m/z 243.0 (M+H)$^+$.

Step C: 2-((3-(1H-tetrazol-5-yl)benzyl)thio)-4-benzyl-6-oxo-1,6-dihydropyridine-3-carbonitrile

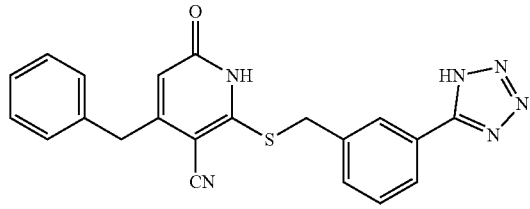 [SMILES: N#Cc1c(Cc2ccccc2)cc(=O)[nH]c1SCc1cccc(-c2nnn[nH]2)c1]

To a solution of 4-benzyl-2-mercapto-6-oxo-1,6-dihydropyridine-3-carbonitrile (150 mg, 0.620 mmol) and 5-(3-(bromomethyl)phenyl)-1H-tetrazole (see Example 49, 177 mg, 0.744 mmol) in DMSO (5 mL) was added DIPEA (120 mg, 0.929 mmol) at room temperature. The reaction mixture was stirred at room temperature for 1 h. TLC (10% MeOH/90% DCM, silica gel plate) showed complete consumption of the starting material after this time. The mixture was purified via reverse phase column chromatography (MeOH/H$_2$O=5%-80%) to give the desired compound (121.1 mg) as a white solid.

$^1$H NMR (400 MHz, DMSO-d$_6$) δ: 8.12 (s, 1H), 7.90 (d, J=7.7 Hz, 1H), 7.66 (d, J=7.7 Hz, 1H), 7.53 (t, J=7.7 Hz, 1H), 7.38-7.29 (m, 2H), 7.26-7.23 (m, 3H), 6.35 (s, 1H), 4.59 (s, 2H), 3.99 (s, 2H). LC-MS (ESI$^+$): m/z 401.1 (M+H)$^+$.

Example 52—Synthesis of 6-((1H-tetrazol-5-yl)methylthio)-4-(trifluoromethyl)pyridin-2(1H)-one Synthesis scheme

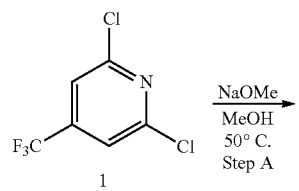

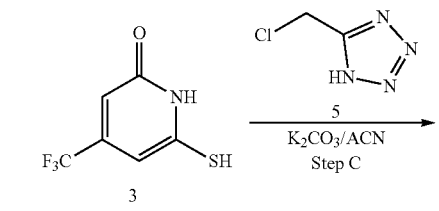

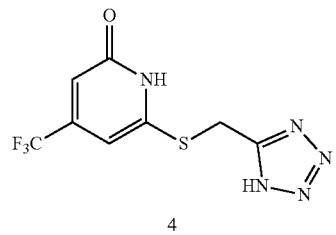

Step A: 2-chloro-6-methoxy-4-(trifluoromethyl)pyridine

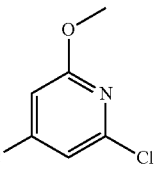

To a solution of 2,6-dichloro-4-(trifluoromethyl)pyridine (2 g, 9.26 mmol) in MeOH (15 mL) was added NaOMe (7 mL, 13.89 mmol, 2 M in MeOH). The resultant mixture was stirred at 50° C. for 2 h. The reaction mixture was extracted with pentane, and the extract was concentrated in vacuo to give desired compound (1.3 g) as a colorless oil which was directly used in the next step. LC-MS (ESI$^+$): m/z 212.0 (M+H)$^+$.

Step B: 6-mercapto-4-(trifluoromethyl)pyridin-2(1H)-one

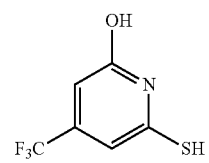 [SMILES: Oc1cc(C(F)(F)F)cc(S)n1]

A mixture of 2-chloro-6-methoxy-4-(trifluoromethyl)pyridine (1.3 g, 6.16 mmol), NaHS (518 mg, 9.24 mmol) in DMF was stirred in a seal tube at 120° C. for 2 h. The reaction mixture was cooled to room temperature, poured into water (10 mL), and acidified to pH=3-5 by addition of 1 N HCl. The resultant mixture was evaporated in vacuo. The residue was purified by silica gel column chromatography, eluting with MeOH/DCM=1/10, to get the desired compound (400 mg, 80% purity) as a yellow solid which was directly used in the next step. LC-MS (ESI$^+$): m/z 196.0 (M+H)$^+$.

Step C: 6-((1H-tetrazol-5-yl)methylthio)-4-(trifluoromethyl)pyridin-2(1H)-one

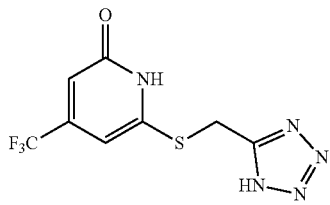 [SMILES: O=c1cc(C(F)(F)F)cc(SCc2nnn[nH]2)[nH]1]

A mixture of 6-mercapto-4-(trifluoromethyl)pyridin-2(1H)-one (80 mg, 0.41 mmol), 5-(chloromethyl)-1H-tetrazole (53 mg, 0.451 mmol), and $K_2CO_3$ (170 mg, 1.23 mmol) in acetonitrile (5 mL) was stirred at room temperature for 2 h. The solvent was removed under reduced pressure. The residue was poured into water (20 mL) and extracted with EtOAc (3×20 mL). The combined organic layers were washed with brine, dried over $Na_2SO_4$, filtered, and concentrated under reduced pressure. The residue was purified by silica gel column chromatography, eluting with MeOH/DCM=1/10, to get the desired compound (50 mg) as a white solid.

$^1$H NMR (400 MHz, DMSO-$d_6$) δ: 7.10 (s, 1H), 6.65 (s, 1H), 4.72 (s, 2H). LC-MS (ESI$^+$): m/z 278.1 (M+H)$^+$

Example 53—Synthesis of 2-(((2H-tetrazol-5-yl)methyl)thio)-4-benzyl-6-oxo-1,6-dihydropyridine-3-carbonitrile Synthesis scheme

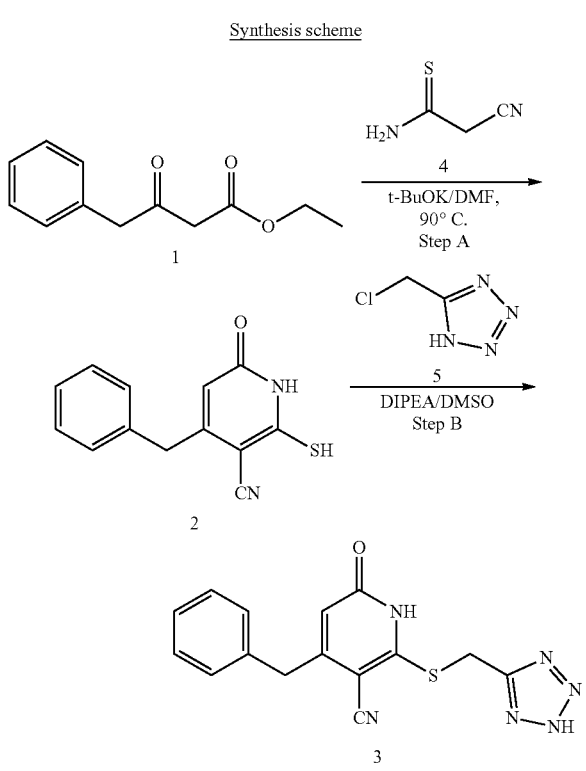

Step A: 4-benzyl-2-mercapto-6-oxo-1,6-dihydropyridine-3-carbonitrile

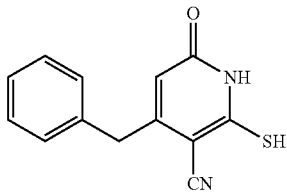 [SMILES: N#Cc1c(Cc2ccccc2)cc(=O)[nH]c1S]

To a solution of ethyl 3-oxo-4-phenylbutanoate (2 g, 10.4 mmol) and 2-cyanoethanethioamide (1.56 g, 15.6 mmol) in DMF (60 mL) was added t-BuOK (5.8 g, 52 mmol) at room temperature. The reaction was heated at 90° C. for 4 h under $N_2$. TLC (50% PE/50% EtOAc, silica gel plate) showed complete consumption of the starting material after this time. The mixture was concentrated in vacuo. The residue was purified via reverse phase column chromatography (MeOH/$H_2O$=5%-80%) to give the desired compound (891 mg) as a brown solid. LC-MS (ESI$^+$): m/z 243.0 (M+H)$^+$.

Step B: 3-(((4-benzyl-3-cyano-6-oxo-1,6-dihydropyridin-2-yl)thio)methyl)benzoic acid

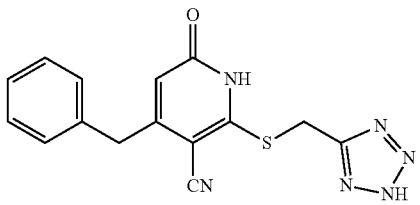 [SMILES: N#Cc1c(Cc2ccccc2)cc(=O)[nH]c1SCc1nn[nH]n1]

To a solution of 4-benzyl-2-mercapto-6-oxo-1,6-dihydropyridine-3-carbonitrile (242 mg, 1.0 mmol) and 5-(chloromethyl)-1H-tetrazole (177.8 mg, 1.5 mmol) in DMSO (16 mL) was added DIPEA (194 mg, 1.5 mmol) at room temperature. The reaction mixture was stirred at room temperature for 1 h. TLC (10% MeOH/90% DCM, silica gel plate) showed complete consumption of the starting material after this time. The mixture was cooled to room temperature, adjusted to pH=5, and extracted with EtOAc (2×50 mL). The combined organic layers were washed with brine, dried and concentrated in vacuo. The mixture was purified via reverse phase column chromatography (MeOH/$H_2O$=5%-80%) to give the desired compound (58.9 mg) as a yellow solid.

$^1$H NMR (400 MHz, DMSO-$d_6$) δ: 7.35 (dd, J=10.3, 4.4 Hz, 2H), 7.30-7.23 (m, 3H), 6.42 (s, 1H), 4.80 (s, 2H), 4.03 (s, 2H). LC-MS (ESI$^+$): m/z 325.1 (M+H)$^+$.

Example 54—Synthesis of 2-(3-(1H-tetrazol-5-yl) benzylthio)-6-oxo-4-(thiophen-3-yl)-1,6-dihydro-pyridine-3-carbonitrile Example 55—Synthesis of 2-((3-(1H-tetrazol-5-yl) benzyl)thio)-6-oxo-4-(m-tolyl)-1,6-dihydropyridine-3-carbonitrile Synthesis scheme

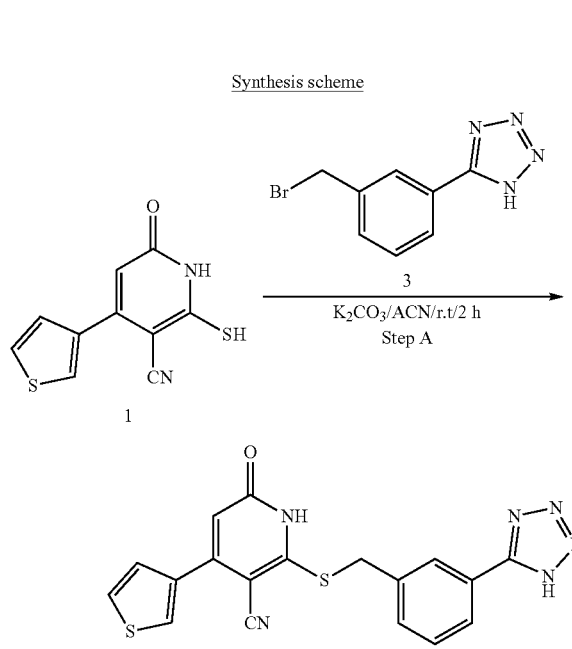

Step A: 2-(3-(1H-tetrazol-5-yl)benzylthio)-6-oxo-4-(thiophen-3-yl)-1,6-dihydropyridine-3-carbonitrile A mixture of 2-mercapto-6-oxo-4-(thiophen-3-yl)-1,6-dihydropyridine-3-carbonitrile (220 mg, 0.94 mmol), 5-(3-(bromomethyl)phenyl)-1H-tetrazole (224 mg, 0.94 mmol), and K$_2$CO$_3$ (260 mg, 1.88 mmol) in acetonitrile (10 mL) was stirred at room temperature for 2 h. The solvent was removed under reduced pressure. The residue was poured into water (20 mL), acidified to pH=3-5 by addition of 1 N HCl, and extracted with EtOAc (3×20 mL). The combined organic layers were washed with brine, dried over Na$_2$SO$_4$, filtered, and concentrated under reduced pressure. The residue was purified by pre-HPLC, eluting with MeOH/water=60% (containing 0.1% HCOOH), to get the desired compound (85 mg) as a yellow solid.

$^1$H NMR (400 MHz, DMSO-d$_6$) δ: 8.16 (s, 1H), 8.09 (br. s., 1H), 7.91 (d, J=7.76 Hz, 1H), 7.74 (dd, J=5.04, 2.89 Hz, 1H), 7.72 (d, J=7.76 Hz, 1H), 7.56 (t, J=7.68 Hz, 1H), 7.50 (d, J=4.95 Hz, 1H), 6.64 (s, 1H), 4.65 (s, 2H). LC-MS (ESI$^+$): m/z 392.9 (M+H)$^+$.

Synthesis scheme

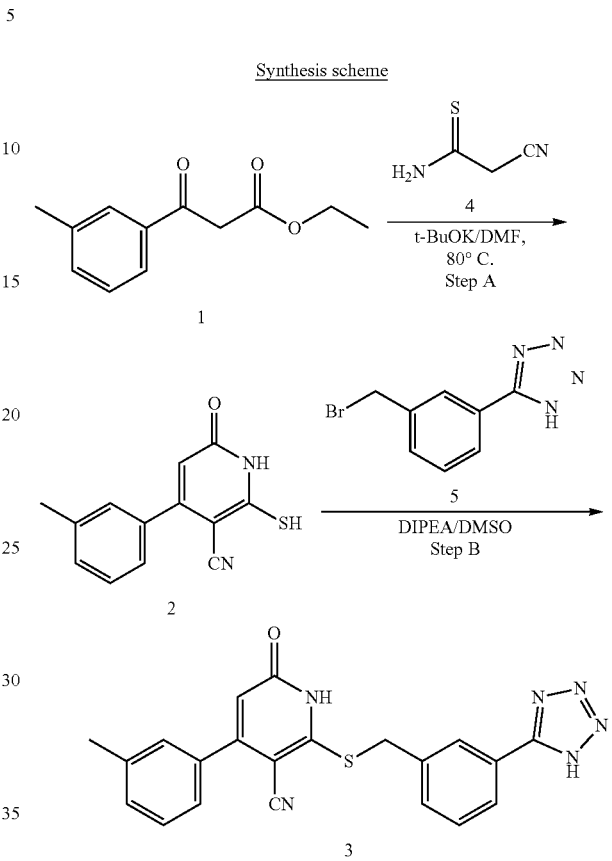

Step A: 2-mercapto-6-oxo-4-(m-tolyl)-1,6-dihydro-pyridine-3-carbonitrile

To a solution of ethyl 3-oxo-3-(m-tolyl)propanoate (2 g, 10.4 mmol) and 2-cyanoethanethioamide (1.56 g, 15.6 mmol) in DMF (50 mL) was added t-BuOK (5.8 g, 52 mmol) at r.t. The reaction was heated at 90° C. for 12 h under N$_2$. TLC (50% PE/50% EtOAc, silica gel plate) showed complete consumption of the starting material after this time. The mixture was cooled to room temperature, adjusted to pH=5.0, and extracted with EtOAc (2×50 mL). The combined organic layer was washed with brine, dried and concentrated in vacuo. The residue was purified via column chromatography (DCM/MeOH=10:1) to give the desired compound (717.1 mg) as a yellow solid. LC-MS (ESI$^+$): m/z 243.0 (M+H)$^+$.

Step B: 2-((3-(1H-tetrazol-5-yl)benzyl)thio)-6-oxo-4-(m-tolyl)-1,6-dihydropyridine-3-carbonitrile

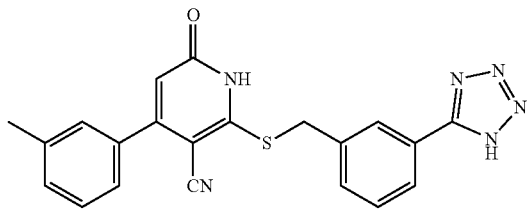 [SMILES: Cc1cccc(-c2cc(=O)[nH]c(SCc3cccc(-c4nnn[nH]4)c3)c2C#N)c1]

To a solution of 2-mercapto-6-oxo-4-(m-tolyl)-1,6-dihydropyridine-3-carbonitrile (242 mg, 1.0 mmol) and 5-(3-(bromomethyl)phenyl)-1H-tetrazole (357 mg, 1.5 mmol) in DMF (10 mL) was added DIPEA (194 mg, 1.5 mmol) at room temperature. The reaction was stirred at room temperature for 1 h. TLC (10% MeOH/90% DCM, silica gel plate) showed complete consumption of the starting material after this time. The mixture was cooled to room temperature, adjusted to pH=5.0, and extracted with EtOAc (2×50 mL). The combined organic layer was washed with brine, dried and concentrated in vacuo. The mixture was purified via reverse phase column chromatography (MeOH/H$_2$O=5%-80%) to give the desired compound (201 mg) as a white solid.

$^1$H NMR (400 MHz, DMSO-d$_6$) δ: 8.19 (s, 1H), 7.91 (d, J=7.7 Hz, 1H), 7.76 (d, J=8.1 Hz, 2H), 7.69 (d, J=7.7 Hz, 1H), 7.55 (t, J=7.7 Hz, 1H), 7.37 (t, J=7.5 Hz, 1H), 7.30 (d, J=7.5 Hz, 1H), 7.15 (s, 1H), 4.73 (s, 2H), 2.34 (s, 3H). LC-MS (ESI$^+$): m/z 400.9 (M+H)$^+$.

Example 56—Synthesis of 3-(((3-cyano-4-methyl-6-oxo-1,6-dihydropyridin-2-yl)thio)methyl)benzoic acid

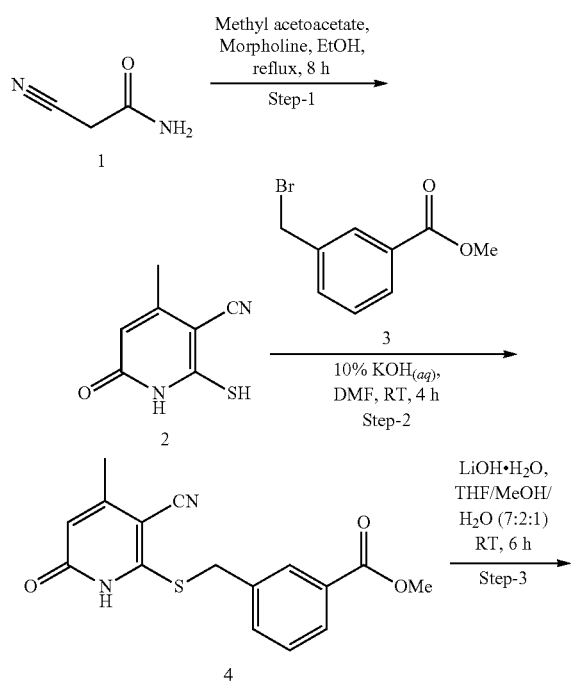

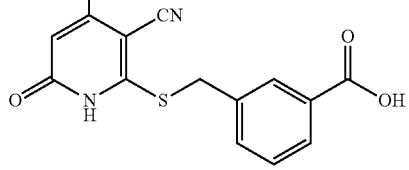

Step-1

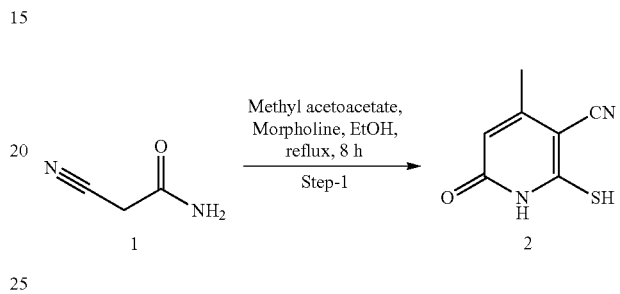

To a stirred suspension of 2-cyano acetamide (500 mg, 5.0 mmol) in EtOH (5 mL), Morpholine (435 mg, 5.0 mmol) was added at RT and heated to 50° C. till it was completely dissolved. Then Methyl acetoacetate (0.54 mL, 5.0 mmol) was added at 50° C.; after the addition the reaction mixture was refluxed for 8 h (TLC indicated complete consumption of starting material), brought to RT and the precipitate formed was filtered. The solid obtained was dissolved in water (10 mL) and acidified with 1N HCl till pH=2. The resulting mixture was stored in refrigerator (0° C.) for 5 h during which solid was formed which was filtered; the solid was washed with Hexane (20 mL) and dried under vacuum to afford 1,6-dihydro-2-mercapto-4-methyl-6-oxopyridine-3-carbonitrile (290 mg, 35%) as an off-white solid.

$^1$H NMR (400 MHz, DMSO-d$_6$) δ: 13.32 (s, 1H), 5.98 (s, 1H), 2.24 (s, 3H). LCMS (ESI$^+$): m/z: 167.36 (M+H)$^+$.

Step-2

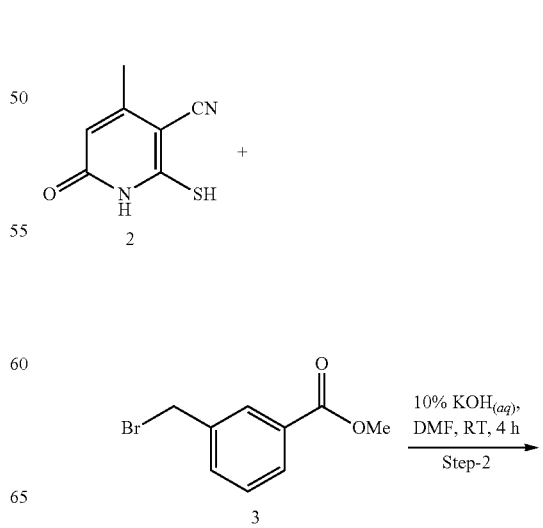

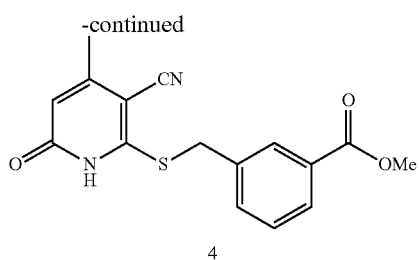

4

To a stirred suspension of 1,6-dihydro-2-mercapto-4-methyl-6-oxopyridine-3-carbonitrile (150 mg, 0.903 mmol) in DMF (2 mL), aqueous 10% KOH (0.24 mL, 0.903 mmol) was added at RT. The resulting mixture was stirred at RT till it was completely dissolved. Then Methyl 3-(bromomethyl) benzoate (206 mg, 0.903 mmol) was added in one portion at RT and stirred for 4 h (TLC indicated complete consumption of starting material). The reaction mixture was diluted with water (15 mL), the solid formed was filtered off and dried under vacuum to give Methyl 3-((3-cyano-1,6-dihydro-4-methyl-6-oxopyridin-2-ylthio)methyl)benzoate (150 mg, 53%) as a white solid.

$^1$H NMR (400 MHz, DMSO-d$_6$) δ: 12.05 (s, 1H), 8.04 (br s, 1H), 7.83 (d, J=8.0 Hz, 1H), 7.74 (d, J=7.2 Hz, 1H), 7.46 (t, J=7.6 Hz, 1H), 6.42 (s, 1H), 4.56 (s, 2H), 3.84 (s, 3H), 2.30 (s, 3H). LCMS (ESI+): m/z: 315.57 (M+H)$^+$.

Step-3

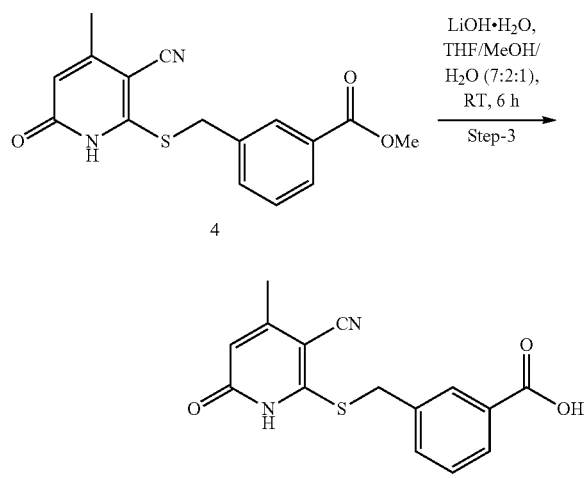

To a stirred solution of Methyl 3-((3-cyano-1,6-dihydro-4-methyl-6-oxopyridin-2-ylthio) methyl)benzoate (150 mg, 0.477 mmol) in THF/MeOH/H$_2$O (5 mL; 7:2:1), LiOH·H$_2$O (60 mg, 1.43 mmol) was added at RT and stirred for 6 h (TLC indicated complete consumption of starting material). The volatiles were removed under reduced pressure, the resultant residue was dissolved in water (10 mL) and acidified with 1N HCl till pH=2. The solid precipitated was filtered off, washed with EtOAc (10 mL) and dried under vacuum to afford 3-(((3-cyano-4-methyl-6-oxo-1,6-dihydropyridin-2-yl)thio)methyl)benzoic acid (110 mg, 77%) as a white solid.

$^1$H NMR (400 MHz, DMSO-d$_6$) δ: 12.92 (s, 1H), 12.14 (s, 1H), 8.00-7.99 (m, 1H), 7.83-7.80 (m, 1H), 7.70 (d, J=7.6 Hz, 1H), 7.43 (t, J=7.6 Hz, 1H), 6.43 (s, 1H), 4.56 (s, 2H), 2.31 (s, 3H). LCMS (ESI$^+$): m/z: 301.52 (M+H)$^+$.

Example 57 Human ACMSD-1 Inhibitor Assay

A solution of 7.8 µg/ml 3-hydroxyanthranilate 3,4-dioxygenase (3-HAO) with protein dilution buffer (50 mM 4-Morpholineethanesulfonic acid "MES" pH 6.0) and a solution of 6 µg/ml Human 2-amino-3-carboxymuconate-6-semialdehyde decarboxylase (human ACMSD) with protein dilution buffer (50 mM MES pH 6.0) were prepared separately. A serial 2-fold dilution of test compounds, from 512 nM until 0.5 nM were prepared.

To a 96-well plate was added 50 µl of 7.8 µg/ml 3-HAO and 50 µl of 2× working solution (50 µM 3-hydroxyanthranilic acid (Sigma 148776), 2 mM ammonium iron(II) sulfate hexahydrate (Sigma V900031), in 50 mM MES pH 6.0) to start the reaction. The plate was placed into a SpectraMax Plus 384 Microplate Reader, Molecular Devices with the temperature set to 28° C. The absorbance at 360 nm for 10 min with 10 seconds interval was monitored and recorded.

To a 96-well plate was added 50 µl of 6 µg/ml human ACMSD with series concentrations of the test compound. The absorbance was recorded at 360 nm for 10 min with 10 seconds interval. The data was analyzed in GraphPad Prism 6. A four-parameter dose-response curve was fitted. "Hill Slope" was constrained between −0.5 and −3, and such constrains was indicated when applied.

The Table below lists inhibitory effects of representative compounds of the present invention against human ACMSD activities.

| Example No. | Structure | hACMSD IC50 (nM) |
|---|---|---|
| | 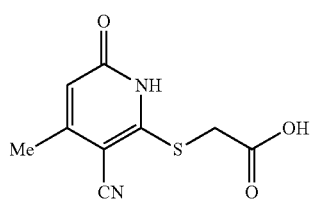 [SMILES: Cc1cc(=O)[nH]c(SCC(=O)O)c1C#N] | 2990 |

-continued

| Example No. | Structure | hACMSD IC50 (nM) |
|---|---|---|
| Ex. 1 | 3-cyano-4-(trifluoromethyl)-6-oxo-1,6-dihydropyridin-2-yl thio-acetic acid | 6 |
| Ex. 2 | 3-{[3-cyano-4-(trifluoromethyl)-6-oxo-1,6-dihydropyridin-2-yl]thio}propanoic acid | 752 |
| Ex. 3 | 3-({[3-cyano-4-(trifluoromethyl)-6-oxo-1,6-dihydropyridin-2-yl]thio}methyl)-4-chlorobenzoic acid | 158 |
| Ex. 4 | 2-{[3-cyano-4-(difluoromethyl)-6-oxo-1,6-dihydropyridin-2-yl]thio}acetic acid | 118 |
| Ex. 5 | 2-{[3-cyano-5-methyl-4-(trifluoromethyl)-6-oxo-1,6-dihydropyridin-2-yl]thio}acetic acid | 26 |
| Ex. 6 | 2-{[3-cyano-4-propyl-6-oxo-1,6-dihydropyridin-2-yl]thio}acetic acid | 3052 |
| Ex. 7 | 2-{[3-cyano-4-(trifluoromethyl)-6-oxo-1,6-dihydropyridin-2-yl]thio}propanoic acid | 271 |

-continued

| Example No. | Structure | hACMSD IC50 (nM) |
|---|---|---|
| Ex. 8 | (3-{[(5-cyano-4-(trifluoromethyl)-6-oxo-1,6-dihydropyridin-2-yl)thio]methyl}benzoic acid) | 1609 |
| Ex. 9 | (4-ethyl-3-cyano-6-oxo-1,6-dihydropyridin-2-yl)thio]acetic acid | 3400 |
| Ex. 10 | (4-tert-butyl-3-cyano-6-oxo-1,6-dihydropyridin-2-yl)thio]acetic acid | 4600 |
| Ex. 11 | (4-(methoxymethyl)-3-cyano-6-oxo-1,6-dihydropyridin-2-yl)thio]acetic acid | 9000 |
| Ex. 12 | (4-phenyl-3-cyano-6-oxo-1,6-dihydropyridin-2-yl)thio]acetic acid | 7000 |
| Ex. 13 | (4-isopropyl-3-cyano-6-oxo-1,6-dihydropyridin-2-yl)thio]acetic acid | 2600 |
| Ex. 14 | (4-cyclopropyl-3-cyano-6-oxo-1,6-dihydropyridin-2-yl)thio]acetic acid | 7300 |

-continued

| Example No. | Structure | hACMSD IC50 (nM) |
|---|---|---|
| Ex. 15 | 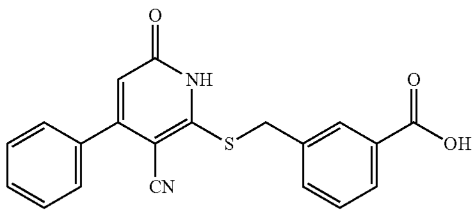 [SMILES: N#Cc1c(-c2ccccc2)cc(=O)[nH]c1SCc1cccc(C(=O)O)c1] | 56 |
| Ex. 16 | 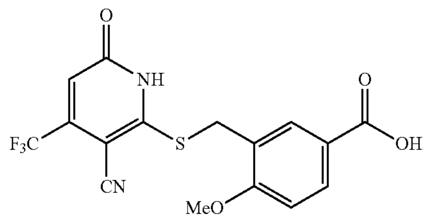 [SMILES: COc1ccc(C(=O)O)cc1CSc1[nH]c(=O)cc(C(F)(F)F)c1C#N] | 530 |
| Ex. 17 | 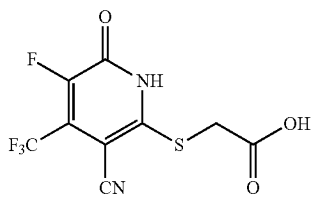 | 9 |
| Ex. 18 | 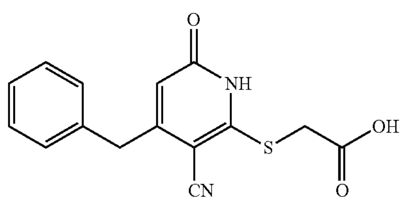 [SMILES: N#Cc1c(Cc2ccccc2)cc(=O)[nH]c1SCC(=O)O] | 36 |
| Ex. 19 | 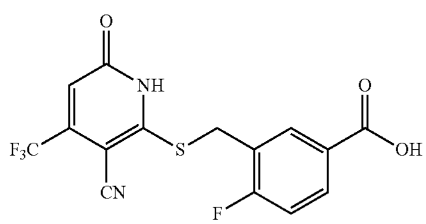 [SMILES: N#Cc1c(C(F)(F)F)cc(=O)[nH]c1SCc1cc(C(=O)O)ccc1F] | 230 |
| Ex. 20 | 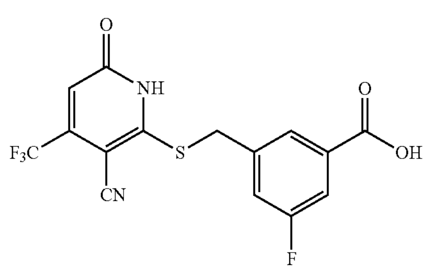 [SMILES: N#Cc1c(C(F)(F)F)cc(=O)[nH]c1SCc1cc(F)cc(C(=O)O)c1] | 350 |
| Ex. 21 | 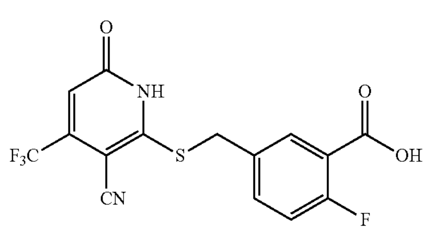 [SMILES: N#Cc1c(C(F)(F)F)cc(=O)[nH]c1SCc1ccc(F)c(C(=O)O)c1] | 780 |

-continued

| Example No. | Structure | hACMSD IC50 (nM) |
|---|---|---|
| Ex. 22 | 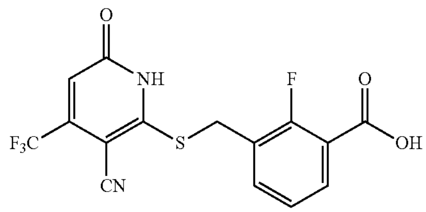 [SMILES: N#Cc1c(C(F)(F)F)cc(=O)[nH]c1SCc1cccc(C(=O)O)c1F] | 830 |
| Ex. 23 | 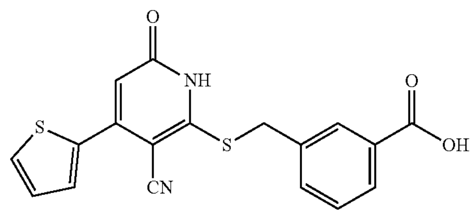 [SMILES: N#Cc1c(-c2cccs2)cc(=O)[nH]c1SCc1cccc(C(=O)O)c1] | 7 |
| Ex. 24 | 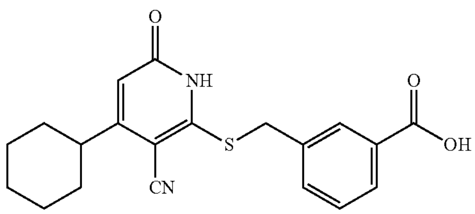 [SMILES: N#Cc1c(C2CCCCC2)cc(=O)[nH]c1SCc1cccc(C(=O)O)c1] | 470 |
| Ex. 25 | 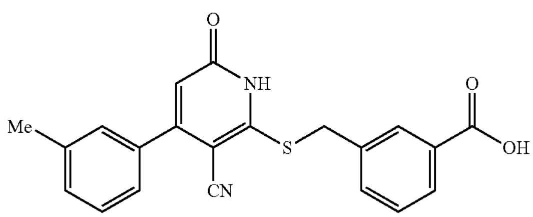 [SMILES: Cc1cccc(-c2cc(=O)[nH]c(SCc3cccc(C(=O)O)c3)c2C#N)c1] | 6 |
| Ex. 26 | 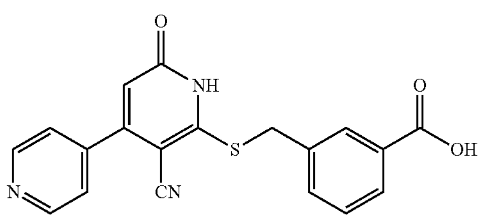 [SMILES: N#Cc1c(-c2ccncc2)cc(=O)[nH]c1SCc1cccc(C(=O)O)c1] | 29 |
| Ex. 27 | 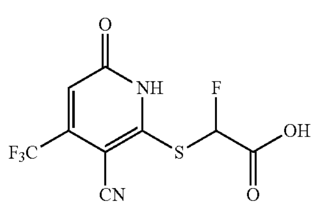 [SMILES: N#Cc1c(C(F)(F)F)cc(=O)[nH]c1SC(F)C(=O)O] | 9 |
| Ex. 28 | 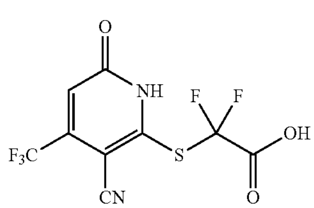 [SMILES: N#Cc1c(C(F)(F)F)cc(=O)[nH]c1SC(F)(F)C(=O)O] | 20 |

-continued

| Example No. | Structure | hACMSD IC50 (nM) |
|---|---|---|
| Ex. 29 | [4-methylphenyl-pyridinone-CN-S-CH2-benzoic acid] | 4 |
| Ex. 30 | [5-fluoro-4-phenyl-pyridinone-CN-S-CH2-benzoic acid] | 70 |
| Ex. 31 | [5-methyl-4-phenyl-pyridinone-CN-S-CH2-benzoic acid] | >10000 |
| Ex. 32 | [4-(pyridin-2-yl)-pyridinone-CN-S-CH2-benzoic acid] | 170 |
| Ex. 33 | [4-phenyl-pyridinone-CN-S-CH2-pyridine-2-carboxylic acid] | 190 |
| Ex. 34 | [4-phenyl-pyridinone-CN-S-CH2-pyridine-3-carboxylic acid] | 3 |
| Ex. 35 | [4-(cyclohexylmethyl)-pyridinone-CN-S-CH2-benzoic acid] | 200 |

-continued

| Example No. | Structure | hACMSD IC50 (nM) |
|---|---|---|
| Ex. 36 | 4-(thiophen-3-yl)-pyridinone with S-CH2-benzoic acid, CN | 160 |
| Ex. 37 | 4-(pyridin-3-yl)-pyridinone with S-CH2-benzoic acid, CN | 50 |
| Ex. 38 | 5-Cl, 4-CF3, 3-CN pyridinone with S-CH2-COOH | 11 |
| Ex. 39 | 5-CN, 4-CF3, 3-CN pyridinone with S-CH2-COOH | >10000 |
| Ex. 40 | 5-Cl, 4-CF3, 3-CN pyridinone with S-CH2-tetrazole | 4 |
| Ex. 41 | 5-Cl, 4-phenyl, 3-CN pyridinone with S-CH2-benzoic acid | 3 |
| Ex. 42 | 4-CF3, 3-CN pyridinone with S-CH2-(3-tetrazolyl-phenyl) | 32 |

-continued
| Example No. | Structure | hACMSD IC50 (nM) |
|---|---|---|
| Ex. 43 | 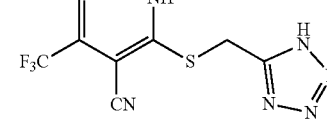 | 4 |
| Ex. 44 | 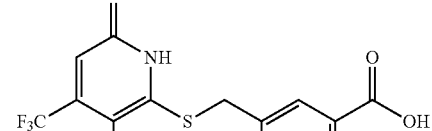 | 510 |
| Ex. 45 | 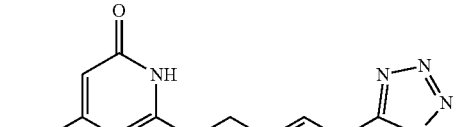 | 4 |
| Ex. 46 | 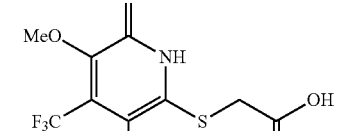 | 8 |
| Ex. 47 | 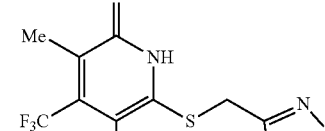 | 7 |
| Ex. 48 | 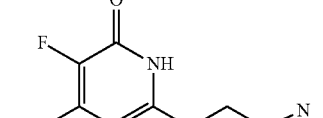 | 2 |
| Ex. 49 | 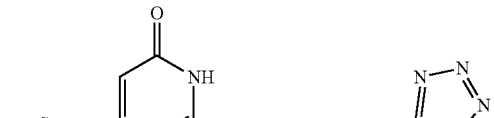 | 6 |

-continued

| Example No. | Structure | hACMSD IC50 (nM) |
|---|---|---|
| Ex. 50 | 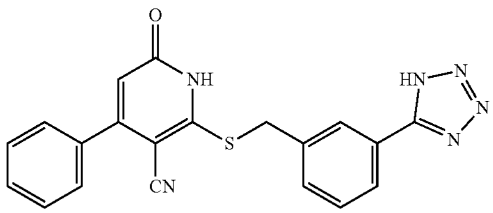 [SMILES: N#Cc1c(-c2ccccc2)cc(=O)[nH]c1SCc1cccc(-c2nnn[nH]2)c1] | 3 |
| Ex. 51 | 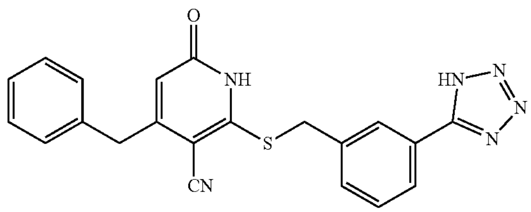 [SMILES: N#Cc1c(Cc2ccccc2)cc(=O)[nH]c1SCc1cccc(-c2nnn[nH]2)c1] | 46 |
| Ex. 52 | 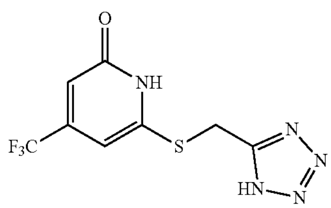 [SMILES: O=c1cc(C(F)(F)F)cc(SCc2nnn[nH]2)[nH]1] | 130 |
| Ex. 53 | 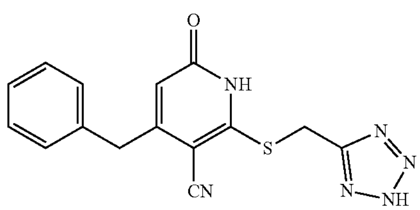 [SMILES: N#Cc1c(Cc2ccccc2)cc(=O)[nH]c1SCc1nn[nH]n1] | 2 |
| Ex. 54 | 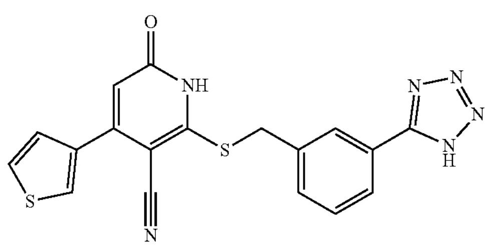 [SMILES: N#Cc1c(-c2ccsc2)cc(=O)[nH]c1SCc1cccc(-c2nnn[nH]2)c1] | 9 |
| Ex. 55 | 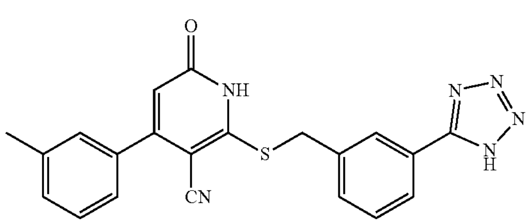 [SMILES: Cc1cccc(-c2cc(=O)[nH]c(SCc3cccc(-c4nnn[nH]4)c3)c2C#N)c1] | 3 |
| Ex. 56 | 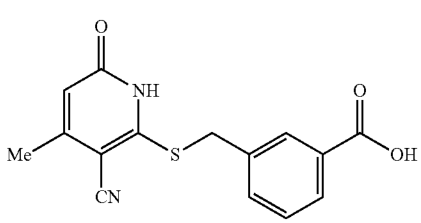 [SMILES: Cc1cc(=O)[nH]c(SCc2cccc(C(=O)O)c2)c1C#N] | 6750 |

What is claimed is:

1. A compound represented by the following structural formula:

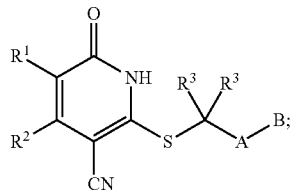

or a pharmaceutically acceptable salt thereof, wherein:
- $R^1$ is —H, —CH$_3$, —OCH$_3$, halomethyl, halomethoxy, halo, or —CN;
- $R^2$ is -halo, (C$_2$-C$_5$)alkyl, halo(C$_1$-C$_5$)alkyl, (C$_3$-C$_6$)cycloalkyl, phenyl, monocyclic heteroaryl, —CN, —NO$_2$, —OR$^c$, —NR$^a$R$^b$, S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, O(C=S)R$^a$, —C(=O)NR$^a$R$^b$, —NR$^a$C(=O)R$^b$, —C(=S)NR$^a$R$^b$, —NR$^a$(C=O)NR$^a$R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, NR$^a$(C=S)NR$^a$R$^b$, —C(=S)R$^a$, or —C(=O)R$^b$, wherein:
  - the (C$_2$-C$_5$)alkyl group represented by $R^2$ is optionally substituted with —CN, —NO$_2$, —OR$^c$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^a$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, —C(=O)R$^a$, (C$_3$-C$_6$)cycloalkyl, monocyclic heteroaryl, or phenyl, wherein the (C$_3$-C$_6$)cycloalkyl, monocyclic heteroaryl and phenyl substituents on the (C$_2$-C$_5$)alkyl group represented by $R^2$ are optionally and independently substituted with —CH$_3$, halomethyl, halo, methoxy or halomethoxy;
  - the (C$_3$-C$_6$)cycloalkyl, phenyl and monocyclic heteroaryl groups represented by $R^2$ are optionally and independently substituted with (C$_1$-C$_5$)alkyl, halo (C$_1$-C$_5$)alkyl, halo, —CN, —NO$_2$, —OR$^c$, —NR$^a$R$^b$, —S(O)$_i$R$^a$, —NR$^a$S(O)$_i$R$^b$, —S(O)$_i$NR$^a$R$^b$, —C(=O)OR$^a$, —OC(=O)OR$^a$, —C(=S)OR$^a$, —O(C=S)R$^a$, —C(=O)NR$^a$R$^b$, —NR$^a$C(=O)R$^b$, —C(=S)NR$^a$R$^b$, —NR$^a$C(=S)R$^b$, —NR$^a$(C=O)OR$^b$, —O(C=O)NR$^a$R$^b$, —NR$^a$(C=S)OR$^b$, —O(C=S)NR$^a$R$^b$, —NR$^a$(C=O)NR$^a$R$^b$, —NR$^a$(C=S)NR$^a$R$^b$, —C(=S)R$^a$, or —C(=O)R$^a$;
- each $R^a$ and each $R^b$ are independently selected from —H and (C$_1$-C$_5$)alkyl, wherein the (C$_1$-C$_5$)alkyl group represented by $R^a$ or $R^b$ is optionally substituted with hydroxyl or (C$_1$-C$_3$)alkoxy;
- $R^c$ is —H, halo(C$_1$-C$_5$)alkyl, or (C$_1$-C$_5$)alkyl, wherein the (C$_1$-C$_5$)alkyl group represented by $R^c$ is optionally substituted with hydroxyl or (C$_1$-C$_3$)alkoxy;
- each i is independently 0, 1, or 2;
- each $R^3$ is independently —H, —CH$_3$, or —F;
- A is absent, —CH$_2$—, a phenylene group or a pyridylene group, wherein the phenylene group and the pyridylene group represented by A are optionally and independently substituted with 1 or 2 groups represented by $R^4$;
- each $R^4$ is independently —CH$_3$, —OCH$_3$, halomethyl, halomethoxy, halo, or —CN; and
- B is —COOH or tetrazolyl;
- provided that the compound is other than

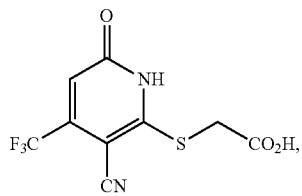

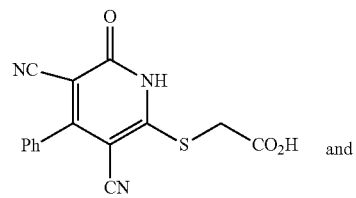

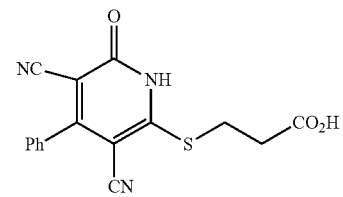

or a pharmaceutically acceptable salt of any of the foregoing.

2. The compound of claim 1, wherein the compound is represented by the following structural formula:

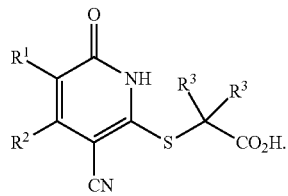

3. The compound of claim 1, wherein the compound is represented by the following structural formula:

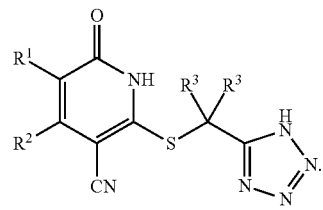

4. The compound of claim 1, wherein the compound is represented by the following structural formula:

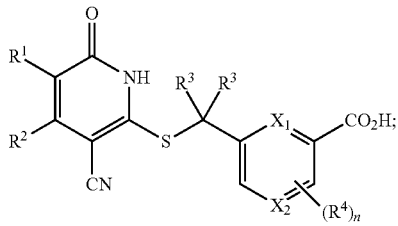

wherein n is 0 or 1, $X_1$ and $X_2$ are each independently CH or N, and at least one of $X_1$ and $X_2$ is CH.

5. The compound of claim 1, wherein the compound is represented by the following structural formula:

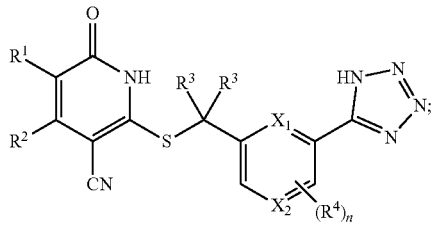

wherein n is 0 or 1, $X_1$ and $X_2$ are each independently CH or N, and at least one of $X_1$ and $X_2$ is CH.

6. The compound of claim 1, wherein the compound is represented by the following structural formula:

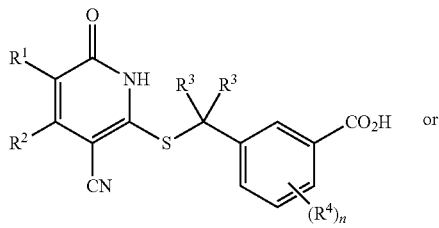

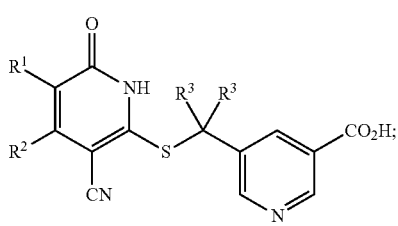

wherein n is 0 or 1.

7. The compound of claim 1, wherein the compound is represented by the following structural formula:

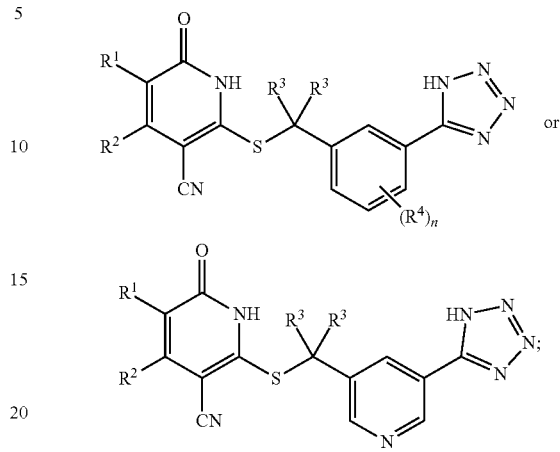

wherein n is 0 or 1.

8. The compound of claim 1, wherein $R^2$ is $(C_2-C_5)$alkyl, $(C_3-C_6)$cycloalkyl, phenyl, thienyl, furanyl, pyrimidyl, pyridyl, benzyl, thienyl-$CH_2$—, furanyl-$CH_2$—, pyridyl-$CH_2$—, or pyrimidyl-$CH_2$—, wherein i) the $(C_2-C_5)$alkyl represented by $R_2$ is optionally substituted with halo, $(C_1-C_5)$alkoxy, or $(C_3-C_6)$cycloalkyl; ii) the phenyl or benzyl group represented by $R_2$ is optionally and independently substituted with —$CH_3$, halomethyl, —$OCH_3$, halomethoxy, or —CN; and iii) the thienyl, furanyl, pyridyl, pyrimidyl, thienyl-$CH_2$—, furanyl-$CH_2$—, pyridyl-$CH_2$—, or pyrimidyl-$CH_2$— group represented by $R_2$ is optionally and independently substituted with —$CH_3$.

9. The compound of claim 1, wherein:

$R^1$ is —H, —$CH_3$, —$OCH_3$, —F, —Cl, or —CN;

$R^2$ is $(C_2-C_5)$alkyl, $(C_3-C_6)$cycloalkyl, phenyl, thienyl, pyridyl, or benzyl, wherein the $(C_2-C_5)$alkyl represented by $R_2$ is optionally substituted with halo, $(C_1-C_5)$alkoxy, or $(C_3-C_6)$cycloalkyl; the phenyl or benzyl group represented by $R_2$ is optionally and independently substituted with —$CH_3$;

$R^3$ is —H, —F, or —$CH_3$; and $R^4$ is —F, —$CH_3$, or methoxy.

10. A pharmaceutical composition comprising a pharmaceutically acceptable carrier or diluent and the compound of claim 1.

11. The pharmaceutical composition of claim 10, wherein the compound is represented by the following structural formula:

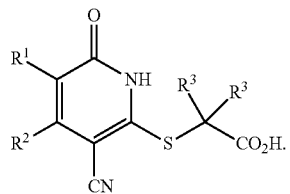

12. The pharmaceutical composition of claim 10, wherein the compound is represented by the following structural formula:

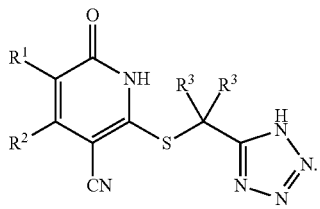

13. The pharmaceutical composition of claim 10, wherein the compound is represented by the following structural formula:

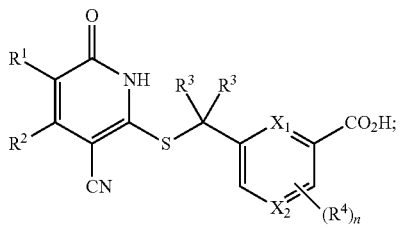

wherein n is 0 or 1, $X_1$ and $X_2$ are each independently CH or N, and at least one of $X_1$ and $X_2$ is CH.

14. The pharmaceutical composition of claim 10, wherein the compound is represented by the following structural formula:

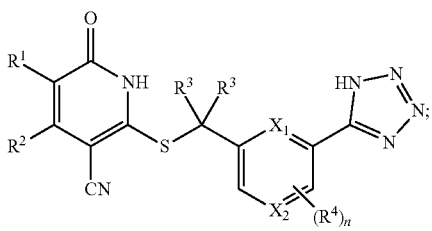

wherein n is 0 or 1, $X_1$ and $X_2$ are each independently CH or N, and at least one of $X_1$ and $X_2$ is CH.

15. The pharmaceutical composition of claim 10, wherein the compound is represented by the following structural formula:

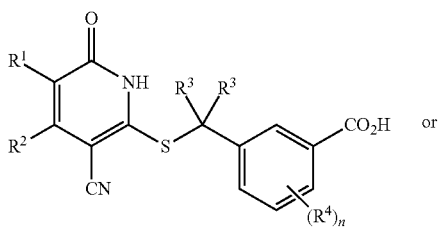

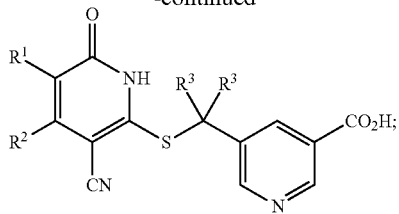

wherein n is 0 or 1.

16. The pharmaceutical composition of claim 10, wherein the compound is represented by the following structural formula:

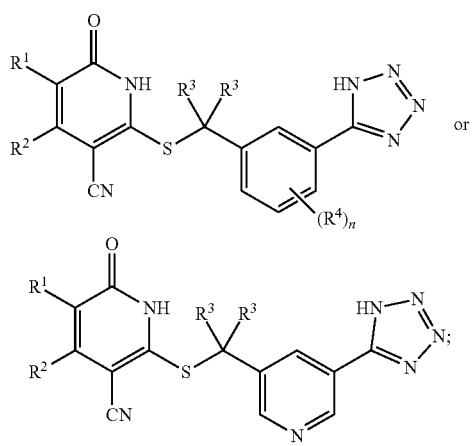

wherein n is 0 or 1.

17. The pharmaceutical composition of claim 10, wherein $R_2$ is $(C_2-C_5)$alkyl, $(C_3-C_6)$cycloalkyl, phenyl, thienyl, furanyl, pyrimidyl, pyridyl, benzyl, thienyl-$CH_2$—, furanyl-$CH_2$—, pyridyl-$CH_2$—, or pyrimidyl-$CH_2$—, wherein i) the $(C_2-C_5)$alkyl represented by $R_2$ is optionally substituted with halo, $(C_1-C_5)$alkoxy, or $(C_3-C_6)$cycloalkyl; ii) the phenyl or benzyl group represented by $R_2$ is optionally and independently substituted with —$CH_3$, halomethyl, —$OCH_3$, halomethoxy, or —CN; and iii) the thienyl, furanyl, pyridyl, pyrimidyl, thienyl-$CH_2$—, furanyl-$CH_2$—, pyridyl-$CH_2$—, or pyrimidyl-$CH_2$— group represented by $R_2$ is optionally and independently substituted with —$CH_3$.

18. The pharmaceutical composition of claim 10, wherein:

$R^1$ is —H, —$CH_3$, —$OCH_3$, —F, —Cl, or —CN;

$R^2$ is $(C_2-C_5)$alkyl, $(C_3-C_6)$cycloalkyl, phenyl, thienyl, pyridyl, or benzyl, wherein the $(C_2-C_5)$alkyl represented by $R_2$ is optionally substituted with halo, $(C_1-C_5)$alkoxy, or $(C_3-C_6)$cycloalkyl; the phenyl or benzyl group represented by $R_2$ is optionally and independently substituted with —$CH_3$;

$R^3$ is —H, —F, or —$CH_3$; and $R^4$ is —F, —Cl, —$CH_3$, or methoxy.

* * * * *